US009184395B2

(12) United States Patent
Kato et al.

(10) Patent No.: US 9,184,395 B2
(45) Date of Patent: Nov. 10, 2015

(54) AROMATIC AMINE DERIVATIVE AND ORGANIC ELECTROLUMINESCENT ELEMENT USING SAME

(75) Inventors: Tomoki Kato, Chiba (JP); Nobuhiro Yabunouchi, Chiba (JP); Takahiro Fujiyama, Chiba (JP)

(73) Assignees: IDEMITSU KOSAN CO., LTD., Tokyo (JP); MITSUI CHEMICALS, INC., Tokyo (JP)

( * ) Notice: Subject to any disclaimer, the term of this patent is extended or adjusted under 35 U.S.C. 154(b) by 121 days.

(21) Appl. No.: 13/979,075

(22) PCT Filed: Jan. 13, 2012

(86) PCT No.: PCT/JP2012/050625
§ 371 (c)(1),
(2), (4) Date: Jul. 17, 2013

(87) PCT Pub. No.: WO2012/096382
PCT Pub. Date: Jul. 19, 2012

(65) Prior Publication Data
US 2013/0299806 A1 Nov. 14, 2013

(30) Foreign Application Priority Data
Jan. 14, 2011 (JP) ................................ 2011-006453

(51) Int. Cl.
*H01L 51/50* (2006.01)
*H01L 51/00* (2006.01)
*C07C 211/61* (2006.01)
*C09K 11/06* (2006.01)
*G03G 5/06* (2006.01)
*H05B 33/10* (2006.01)
*C09B 57/00* (2006.01)

(52) U.S. Cl.
CPC ............ *H01L 51/006* (2013.01); *C07C 211/61* (2013.01); *C09B 57/00* (2013.01); *C09B 57/008* (2013.01); *C09K 11/06* (2013.01); *G03G 5/0614* (2013.01); *H05B 33/10* (2013.01); *C07C 2103/18* (2013.01); *C07C 2103/26* (2013.01); *C07C 2103/94* (2013.01); *C09K 2211/1007* (2013.01); *C09K 2211/1011* (2013.01); *C09K 2211/1014* (2013.01); *H01L 51/5012* (2013.01); *H01L 51/5056* (2013.01)

(58) Field of Classification Search
None
See application file for complete search history.

(56) References Cited

U.S. PATENT DOCUMENTS

| 2011/0017983 A1 | 1/2011 | Mizuki et al. |
| 2011/0297924 A1 | 12/2011 | Yabunouchi et al. |
| 2012/0012832 A1 | 1/2012 | Yabunouchi et al. |
| 2012/0146014 A1 | 6/2012 | Kato |
| 2012/0248426 A1 | 10/2012 | Kato |
| 2012/0292606 A1 | 11/2012 | Kato |
| 2013/0221331 A1 | 8/2013 | Mizuki et al. |

FOREIGN PATENT DOCUMENTS

| JP | 2008 537948 | 10/2008 |
| JP | 2010-150425 A | 7/2010 |
| JP | 2010-222268 A | 10/2010 |
| KR | 10-2010-0006072 A | 1/2010 |
| KR | 10-2011-0134581 A | 12/2011 |
| WO | WO 2004/020387 A1 | 3/2004 |
| WO | 2008 006449 | 1/2008 |
| WO | 2010 103765 | 9/2010 |
| WO | 2010 106806 | 9/2010 |
| WO | WO 2012/015265 A1 | 2/2012 |

OTHER PUBLICATIONS

U.S. Appl. No. 14/091,044, filed Nov. 26, 2013, Yabunouchi, et al.
Tang, C.W. et al., "Organic electroluminescent diodes," Appl. Phys. Lett., American Institute of Physics, vol. 51, No. 12, pp. 913 to 915, (Sep. 21, 1987).
International Search Report Issued Apr. 10, 2012 in PCT/JP12/50625 Filed Jan. 13, 2012.
Combined Chinese Office Action and Search Report issued Jun. 17, 2014 in Patent Application No. 201280005266.4 with English Translation of Category of Cited Documents.

*Primary Examiner* — Gregory Clark
(74) *Attorney, Agent, or Firm* — Oblon, McClelland, Maier & Neustadt, L.L.P.

(57) ABSTRACT

To provide an organic EL element material that is capable of enhancing the light emission efficiency and the lifetime of the element as compared to an ordinary organic EL element material, and an organic EL element using the same. Specifically, to provide an aromatic amine derivative represented by Ar¹Ar²Ar³N, and an organic EL element using the same. Representative compounds include the following.

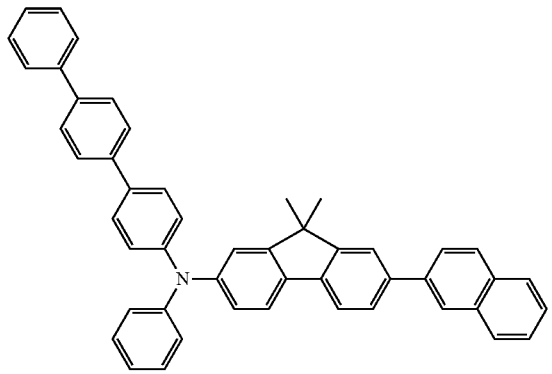

HT1

-continued
HT2
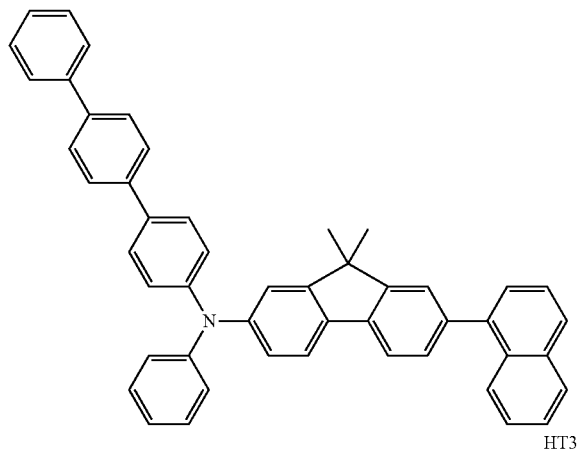
HT5
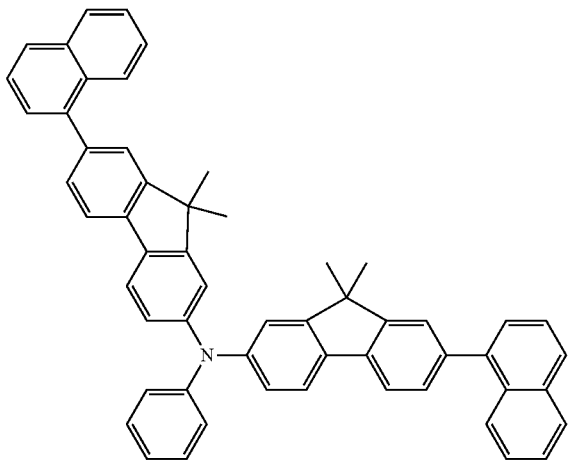
HT3
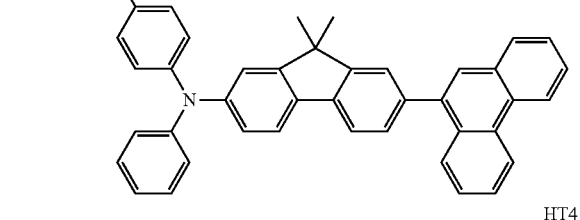
HT6
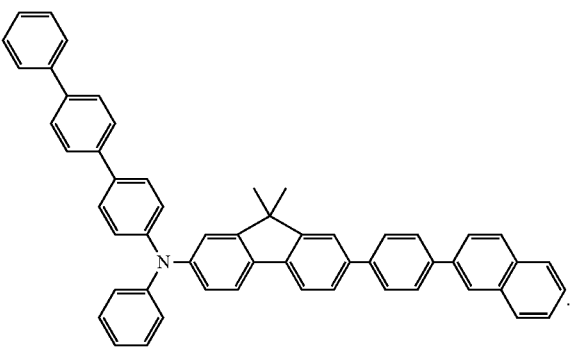
HT4
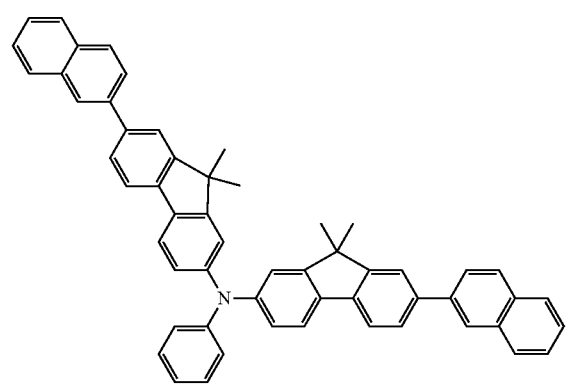
12 Claims, No Drawings

AROMATIC AMINE DERIVATIVE AND ORGANIC ELECTROLUMINESCENT ELEMENT USING SAME

TECHNICAL FIELD

The present invention relates to an aromatic amine derivative and an organic electroluminescent element using the same.

BACKGROUND ART

An organic electroluminescent (EL) element is a self-luminescent element utilizing such a principle that a fluorescent substance emits light with recombination energy of holes injected from an anode and electrons injected from a cathode on application of an electric field. An organic EL element containing an organic material as a constitutional material has been actively investigated since the report by C. W. Tang, et al., Eastman Kodak Corporation, for a low voltage driving organic EL element with a stacked device (see Non-patent Document 1).

Tang, et al. discloses an organic EL element having a laminated structure using tris(8-quinolinolato)aluminum in a light emitting layer and triphenyldiamine in a hole transporting layer. The advantages of the use of the laminated structure in the organic EL element include the following: (i) the injection efficiency of holes into the light emitting layer is enhanced; (ii) electrons injected from the cathode to the light emitting layer are blocked by the hole transporting (injection) layer, and thereby the formation efficiency of excitons formed through recombination in the light emitting layer is enhanced; and (iii) the confinement of the excitons formed in the light emitting layer inside the light emitting layer is facilitated. For enhancing the recombination efficiency of holes and electrons thus injected in the organic EL element having the laminated structure, researches have been made for the structure and the formation method of the element, and the materials of the layers.

In general, the storage or operation of an organic EL element under a high temperature environment may cause adverse affects, such as change of the light emission color, decrease of the light emission efficiency, increase of the operation voltage, and reduction of the lifetime of the element.

For preventing the adverse affects, there have been proposals of aromatic amine derivatives having a carbazole skeleton, a fluorene skeleton, a dibenzofuran skeleton or a dibenzothiophene skeleton, as an organic EL element material (see Patent Documents 1 to 3).

RELATED ART DOCUMENTS

Patent Documents

Patent Document 1: JP-A-2008-537948
Patent Document 2: WO 08/006,449
Patent Document 3: WO 10/106,806

Non-Patent Document

Non-patent Document 1: C. W. Tang and S. A. Vanslyke, Applied Physics Letters, vol. 51, p. 913 (1987)

SUMMARY OF THE INVENTION

Problems to be Solved by the Invention

However, the amine derivatives disclosed in Patent Documents 1 to 3 are still insufficient in the light emission efficiency of the organic EL element and in the lifetime of the element, there is room for further improvement. In particular, while Patent Document 3 succeeds at operation of an organic EL element at a low voltage, the aromatic amine derivative having a fluorene skeleton has a smaller ionization potential than the ionization potential of the host material used in the light emitting layer, and the use of the aromatic amine derivative as the hole transporting material of the organic EL element brings about a problem that the large energy barrier between the hole transporting layer and the light emitting layer suppresses injection of holes to the light emitting layer, which makes the light emission efficiency insufficient.

An object of the present invention is to provide an organic EL element material that is capable of enhancing the light emission efficiency and the lifetime of the element as compared to an ordinary organic EL element material, and to provide an organic EL element using the same.

Means for Solving the Problems

As a result of earnest investigations made by the present inventors for solving the problems, it has been found that the use of an aromatic amine derivative having an aromatic hydrocarbon group with a particular structure and a substituted or unsubstituted phenyl group as an organic EL element material, particularly a hole transporting material, enhances the light emission efficiency and the lifetime of the organic EL element.

Accordingly, the present invention relates to the following items (1) and (2).

(1) An aromatic amine derivative represented by the following general formula (1):

wherein $Ar^1$ represents an organic group A represented by the following general formula (A-1) or (A-2); $Ar^2$ represents the organic group A or an organic group B represented by the following general formula (B-1); and $Ar^3$ represents an organic group C represented by the following general formula (C-1), provided that when both $Ar^1$ and $Ar^2$ represent the organic groups A, the organic groups A may be the same as or different from each other,

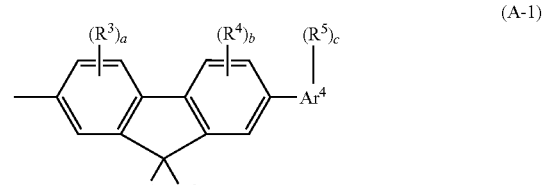

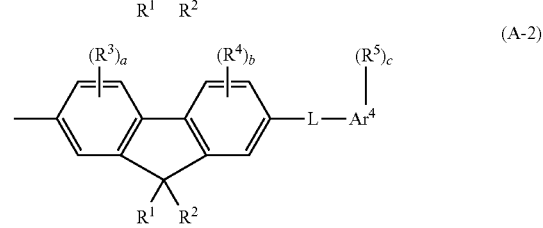

wherein $Ar^4$ represents a substituted or unsubstituted condensed ring group having from 10 to 14 ring-forming carbon atoms; $R^1$ and $R^2$ each independently represent a hydrogen atom, an alkyl group having from 1 to 10 carbon atoms, a cycloalkyl group having from 3 to 10 ring-forming carbon atoms or an aryl group having from 6 to 12 ring-forming carbon atoms, provided that $R^1$ and $R^2$ may be bonded to each other to form a hydrocarbon ring; $R^3$ to $R^5$ each independently represent an alkyl group having from 1 to 10 carbon atoms, a cycloalkyl group having from 3 to 10 ring-forming carbon atoms or an aryl group having from 6 to 12 ring-forming carbon atoms, or $R^3$ to $R^5$ are bonded to each other to form a hydrocarbon ring; L represents a substituted or unsubstituted arylene group having from 6 to 10 ring-forming carbon atoms; and a, b and c each independently represent an integer of from 0 to 2, provided that when a, b or c is 2, the hydrocarbon ring includes a ring formed by bonding plural groups of $R^3$, plural groups of $R^4$ or plural groups of $R^5$,

wherein $Ar^5$ and $Ar^6$ each independently represent a substituted or unsubstituted arylene group having from 6 to 14 ring-forming carbon atoms; $Ar^7$ represents a substituted or unsubstituted aryl group having from 6 to 14 ring-forming carbon atoms; $R^6$ to $R^8$ each independently represent an alkyl group having from 1 to 10 carbon atoms, a cycloalkyl group having from 3 to 10 carbon atoms or an aryl group having from 6 to 12 ring-forming carbon atoms, or $R^6$ to $R^8$ are bonded to each other to form a hydrocarbon ring; and d, e and f each independently represent an integer of from 0 to 2; and g represents 0 or 1, provided that when d, e or f is 2, the hydrocarbon ring includes a ring formed by bonding plural groups of $R^6$, plural groups of $R^7$ or plural groups of $R^8$,

wherein $R^{11}$ represents an alkyl group having from 1 to 10 carbon atoms or a cycloalkyl group having from 3 to 10 carbon atoms; and h represents an integer of from 0 to 2, provided that when h is 2, plural groups of $R^{11}$ are not bonded to each other to form a ring.

(2) An organic electroluminescent element containing an anode and a cathode, having intervening therebetween a light emitting layer, the organic electroluminescent element having at least one organic thin film layer containing the aromatic amine derivative according to the item (1).

Advantages of the Invention

The use of the aromatic amine derivative of the present invention as a material for an organic EL element enables an operation at a low voltage and enhances the light emission efficiency and the lifetime of the organic EL element, as compared to the use of an ordinary organic EL element material.

EMBODIMENTS FOR CARRYING OUT THE INVENTION

The aromatic amine derivative of the present invention is represented by the following formula (1).

In the formula (1), $Ar^1$ represents an organic group A represented by the following general formula (A-1) or (A-2); $Ar^2$ represents the organic group A or an organic group B represented by the following general formula (B-1); and $Ar^3$ represents an organic group C represented by the following general formula (C-1). When both $Ar^1$ and $Ar^2$ represent the organic groups A, the organic groups A may be the same as or different from each other.

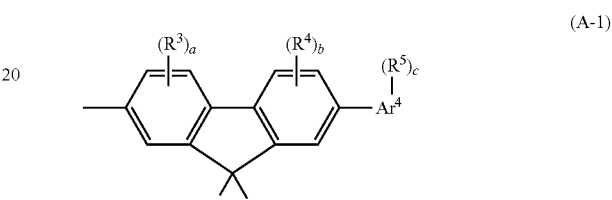

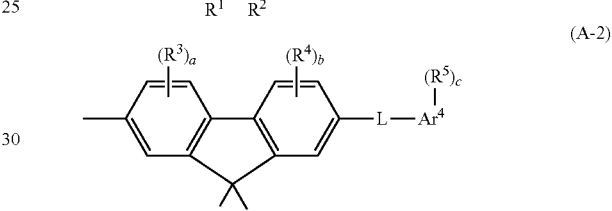

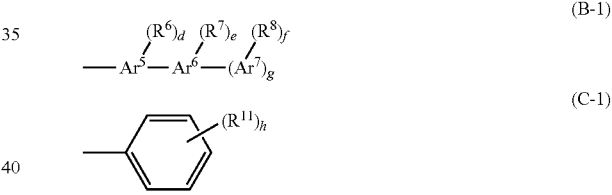

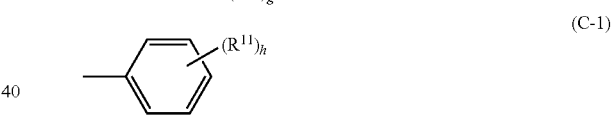

In the formulae (A-1) and (A-2), $Ar^4$ represents a substituted or unsubstituted condensed ring group having from 10 to 14 ring-forming carbon atoms; $R^1$ and $R^2$ each independently represent a hydrogen atom, an alkyl group having from 1 to 10 carbon atoms, a cycloalkyl group having from 3 to 10 ring-forming carbon atoms or an aryl group having from 6 to 12 ring-forming carbon atoms, provided that $R^1$ and $R^2$ may be bonded to each other to form a hydrocarbon ring; $R^3$ to $R^5$ each independently represent an alkyl group having from 1 to 10 carbon atoms, a cycloalkyl group having from 3 to 10 ring-forming carbon atoms or an aryl group having from 6 to 12 ring-forming carbon atoms, or $R^3$ to $R^5$ are bonded to each other to form a hydrocarbon ring; and L represents a substituted or unsubstituted arylene group having from 6 to 10 ring-forming carbon atoms.

a, b and c each independently represent an integer of from 0 to 2, provided that when a, b or c is 2, the hydrocarbon ring includes a ring formed by bonding plural groups of $R^3$, plural groups of $R^4$ or plural groups of $R^5$.

Examples of the condensed ring group having from 10 to 14 ring-forming carbon atoms represented by $Ar^4$ include a 1-naphthyl group, a 2-naphthyl group, a 1-phenanthryl group, a 2-phenanthryl group, a 3-phenanthryl group and a 9-phenanthryl group, and 1-naphthyl group, a 2-naphthyl group and 9-phenanthryl group are preferred from the standpoint of the light emission efficiency and the lifetime of the organic EL element. The condensed ring group may have a substituent, and examples of the substituent include an alkyl group having from 1 to 10 carbon atoms, such as a methyl group, an ethyl group, a n-propyl group, an isopropyl group, a n-butyl group, a s-butyl group, a t-butyl group, various hexyl groups (the term "various" means inclusion of a linear group and all branched groups, hereinafter the same), various octyl groups and various decyl groups, and an alkyl group having from 1 to 5 carbon atoms is preferred from the standpoint of the light emission efficiency and the lifetime of the organic EL element. The substituent is hereinafter referred to as a substituent (I).

Examples of the alkyl group having from 1 to 10 carbon atoms represented by $R^1$ to $R^5$ include an alkyl group having from 1 to 10 carbon atoms, such as a methyl group, an ethyl group, a n-propyl group, an isopropyl group, a n-butyl group, a s-butyl group, a t-butyl group, various hexyl groups, various octyl groups and various decyl groups, and an alkyl group having from 1 to 5 carbon atoms is preferred, an alkyl group having from 1 to 3 carbon atoms is more preferred, a methyl group and an ethyl group are further preferred, and a methyl group is particularly preferred, from the standpoint of the light emission efficiency and the lifetime of the organic EL element.

Examples of the cycloalkyl group having from 3 to 10 ring-forming carbon atoms represented by $R^1$ to $R^5$ include a cyclopropyl group, a cyclobutyl group, a cyclopentyl group, a cyclohexyl group and a cyclooctyl group.

Examples of the aryl group having from 6 to 12 ring-forming carbon atoms represented by $R^1$ to $R^5$ include a phenyl group, a naphthyl group and a biphenyl group, and a phenyl group is preferred from the standpoint of the light emission efficiency and the lifetime of the organic EL element.

Among these, preferred examples of $R^1$ and $R^2$ include an alkyl group having from 1 to 10 carbon atoms and an aryl group having from 6 to 12 ring-forming carbon atoms, and more preferred examples thereof are as described above, from the standpoint of the light emission efficiency and the lifetime of the organic EL element.

Examples of the arylene group having from 6 to 10 ring-forming carbon atoms represented by L include a phenylene group and a naphthalenediyl group, and a phenylene group is preferred, and a 1,4-phenylene group is more preferred, from the standpoint of the light emission efficiency and the lifetime of the organic EL element.

a, b and c each independently preferably represent 0 or 1, and more preferably 0, from the standpoint of the light emission efficiency and the lifetime of the organic EL element.

$R^3$ to $R^5$ may be bonded to each other to form a hydrocarbon ring, and examples of the hydrocarbon ring that is formed by $R^3$ and $R^4$ include hydrocarbon rings shown in the following formulae.

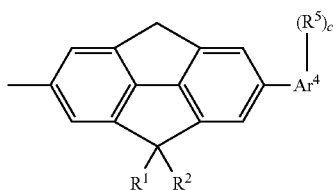

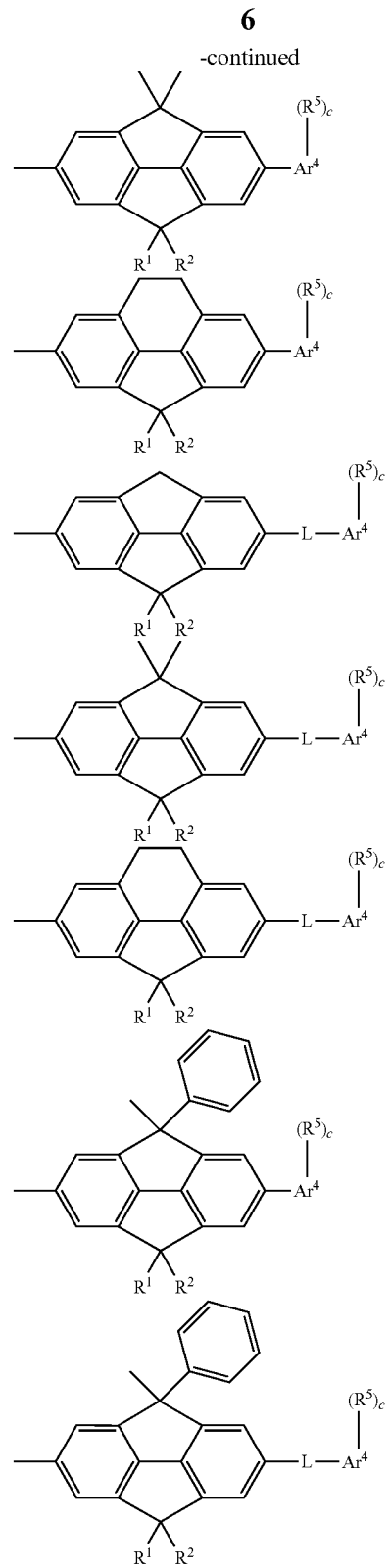

When a, b or c is 2, plural groups of $R^3$, plural groups of $R^4$ or plural groups of $R^5$ may be bonded to each other to form a hydrocarbon ring together with the benzene ring, on which the groups are substituted. Examples of the hydrocarbon ring formed by bonding plural groups of $R^3$ or plural groups of $R^4$ include structures represented by the following general formulae.

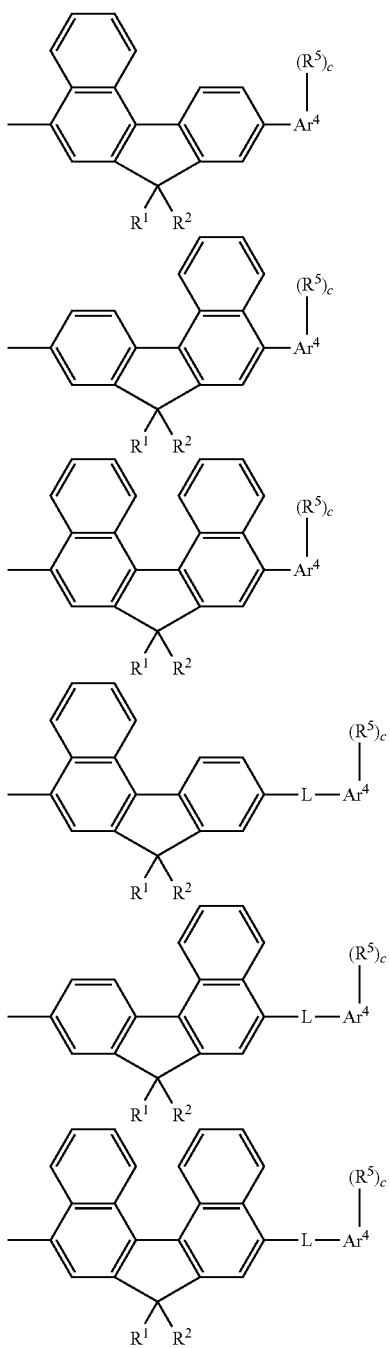

In the formula (B-1), $Ar^5$ and $Ar^6$ each independently represent a substituted or unsubstituted arylene group having from 6 to 14 ring-forming carbon atoms; $Ar^7$ represents a substituted or unsubstituted aryl group having from 6 to 14 ring-forming carbon atoms; $R^6$ to $R^8$ each independently represent an alkyl group having from 1 to 10 carbon atoms, a cycloalkyl group having from 3 to 10 carbon atoms or an aryl group having from 6 to 12 ring-forming carbon atoms, or $R^6$ to $R^8$ are bonded to each other to form a hydrocarbon ring.

d, e and f each independently represent an integer of from 0 to 2; and g represents 0 or 1, provided that when d, e or f is 2, the hydrocarbon ring formed by bonding $R^6$ to $R^8$ includes a ring formed by bonding plural groups of $R^6$, plural groups of $R^7$ or plural groups of $R^8$.

Examples of the arylene group having from 6 to 14 ring-forming carbon atoms represented by $Ar^5$ and $Ar^6$ include a phenylene group, a naphthalenediyl group, a biphenylene group and a phenanthrylenediyl group, and a phenylene group is preferred, and a 1,4-phenylene group is more preferred, from the standpoint of the light emission efficiency and the lifetime of the organic EL element. The arylene group may have a substituent, and examples of the substituent include the same groups as the substituent (I), and preferred examples thereof are the same.

Examples of the aryl group having from 6 to 14 ring-forming carbon atoms represented by $Ar^7$ include a phenyl group, a naphthyl group, an anthryl group and a phenanthryl group, and a phenyl group and a naphthyl group are preferred, and a phenyl group is more preferred, from the standpoint of the light emission efficiency and the lifetime of the organic EL element. The aryl group may have a substituent, and examples of the substituent include the same groups as the substituent (I), and preferred examples thereof are the same.

Examples of the alkyl group having from 1 to 10 carbon atoms, the cycloalkyl group having from 3 to 10 carbon atoms and the aryl group having from 6 to 12 ring-forming carbon atoms represented by $R^6$ to $R^8$ include the same groups as in $R^3$ to $R^5$, and preferred examples thereof are the same.

d, e and f each independently preferably represent 0 or 1, and more preferably 0, from the standpoint of the light emission efficiency and the lifetime of the organic EL element.

g preferably represents 1 from the standpoint of the light emission efficiency and the lifetime of the organic EL element.

When g is 0, $R^8$ represents a substituent that is bonded directly to $Ar^6$.

The hydrocarbon ring formed by bonding $R^6$ to $R^8$ may be considered as similar to $R^3$ to $R^5$, and examples thereof include 5-membered rings and 6-membered rings.

When d, e or f is 2, plural groups of $R^6$, plural groups of $R^7$ or plural groups of $R^8$ may be bonded to each other to form a hydrocarbon ring together with the benzene ring, on which the groups are substituted. The ring may be considered as similar to $R^3$ to $R^5$, and examples thereof include 5-membered rings and 6-membered rings. Taking the case where $Ar^6$ and $Ar^7$ each represent a phenylene group as an example, examples of the hydrocarbon group formed by bonding $R^6$ and $R^7$ include 5-membered rings and a 6-membered ring shown in the following formulae.

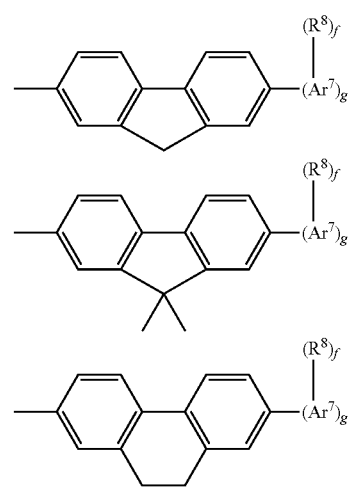

The organic group B is preferably represented by the following general formula (B-2) from the standpoint of the light emission efficiency and the lifetime of the organic EL element.

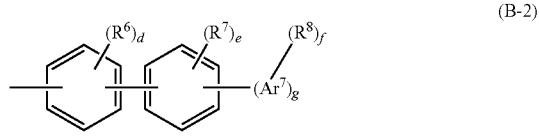

In the formula (B-2), $Ar^7$, $R^6$ to $R^8$, d, e, f and g have the same meanings as above, and preferred examples thereof are the same.

The organic group B is more preferably represented by one of the following general formulae (B-3) to (B-5) from the standpoint of the light emission efficiency and the lifetime of the organic EL element.

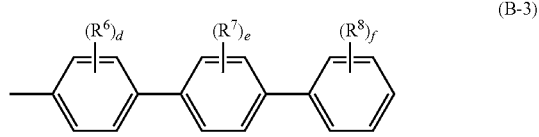

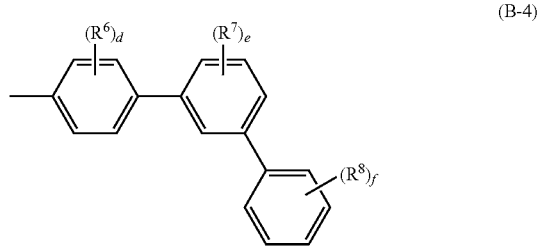

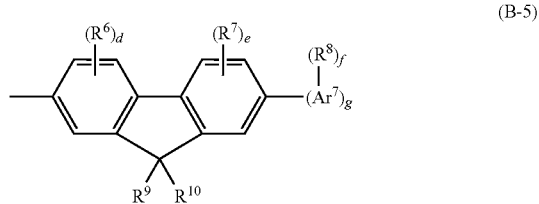

In the formulae (B-3) to (B-5), $Ar^7$, $R^6$ to $R^8$, d, e, f and g have the same meanings as above, and preferred examples thereof are the same.

$R^9$ and $R^{10}$ each independently represent a hydrogen atom, an alkyl group having from 1 to 10 carbon atoms, a cycloalkyl group having from 3 to 10 ring-forming carbon atoms or an aryl group having from 6 to 12 ring-forming carbon atoms. Examples of the alkyl group, the cycloalkyl group and the aryl group represented by $R^9$ and $R^{10}$ include the same groups as in $R^1$ and $R^2$, and preferred examples thereof are the same.

In the formula (C-1), $R^{11}$ represents an alkyl group having from 1 to 10 carbon atoms or a cycloalkyl group having from 3 to 10 carbon atoms; and h represents an integer of from 0 to 2. When h is 2, plural groups of $R^{11}$ are not bonded to each other to form a ring, and therefore the organic group C is a substituted or unsubstituted phenyl group in any case.

Examples of the alkyl group having from 1 to 10 carbon atoms and the cycloalkyl group having from 3 to 10 carbon atoms represented by $R^{11}$ include the same groups as in $R^3$ to $R^5$, and preferred examples thereof are the same.

h preferably represents 0 or 1, and more preferably 0, from the standpoint of the light emission efficiency and the lifetime of the organic EL element.

The aromatic amine derivative represented by the general formula (1) of the present invention is preferably (i) a derivative wherein $Ar^1$ is the organic group A represented by the general formula (A-1) from the standpoint of the light emission efficiency and the lifetime of the organic EL element. The aromatic amine derivative is also preferably (ii) a derivative wherein $Ar^2$ is the organic group B, more preferably (iii) a derivative wherein $Ar^2$ is the organic group B represented by the general formula (B-2), and further preferably (iv) a derivative wherein $Ar^2$ is the organic group B represented by one of the general formulae (B-3) to (B-5).

In addition, (v) a derivative wherein $Ar^1$ and $Ar^2$ are each the organic group A (provided that $Ar^1$ and $Ar^2$ may be the same as or different from each other) is also preferred from the standpoint of the light emission efficiency and the lifetime of the organic EL element.

As for more preferred examples of the aromatic amine derivative, reference may be made to the descriptions for the groups shown above.

Specific examples of the aromatic amine derivative represented by the general formula (1) of the present invention are shown below, but the aromatic amine derivative is not limited thereto.

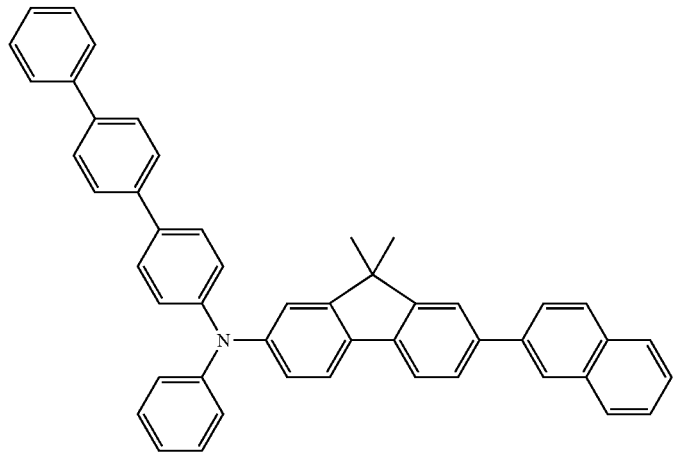

-continued
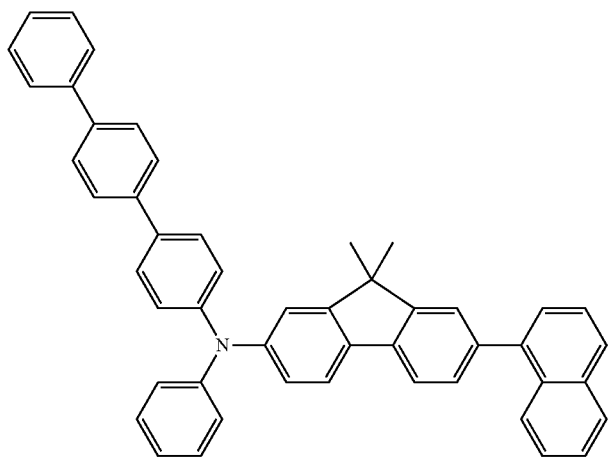
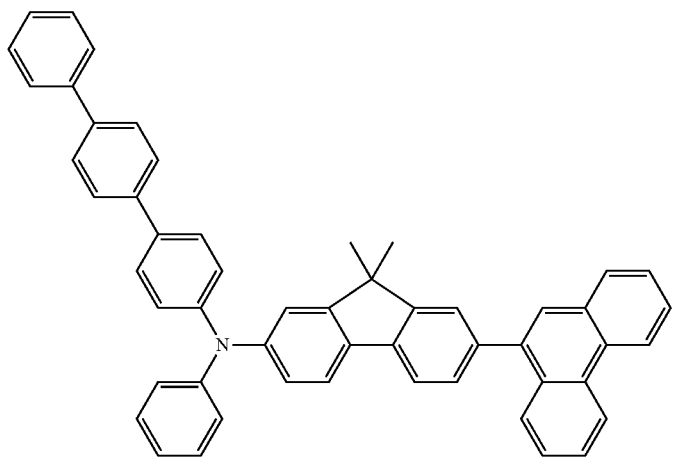
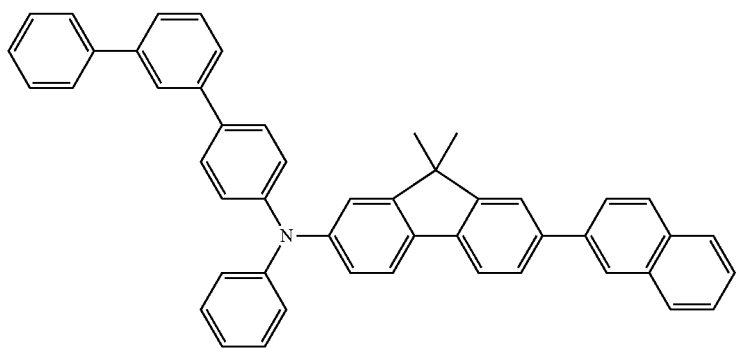
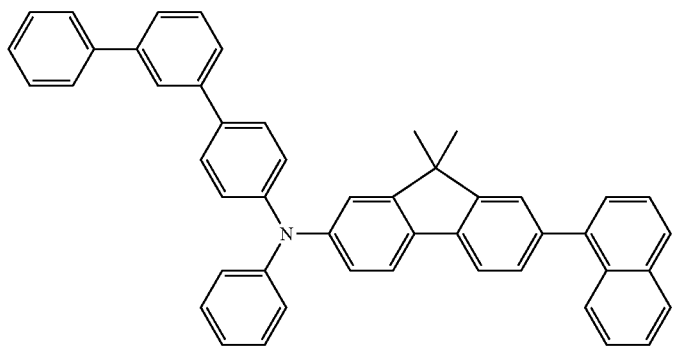

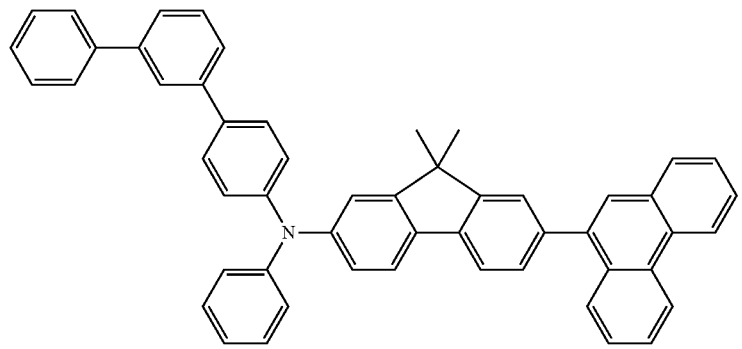
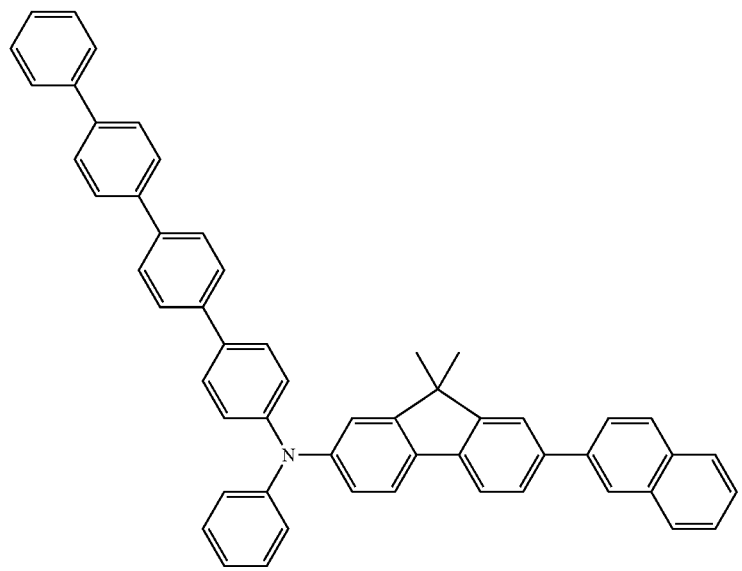
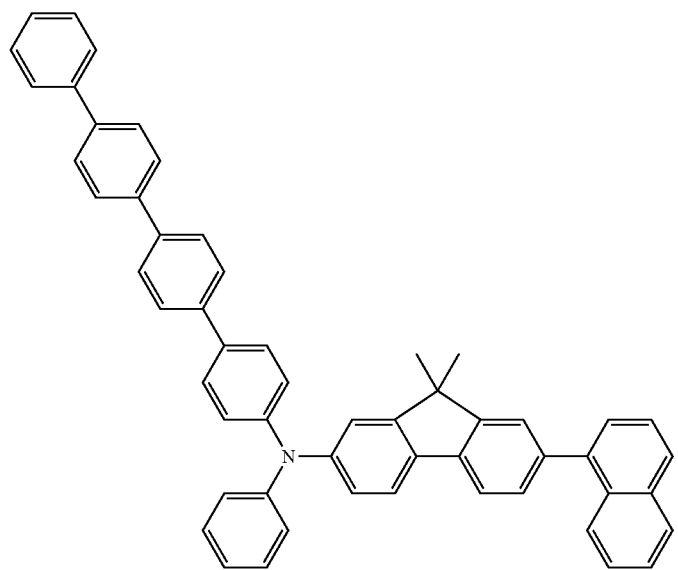

-continued
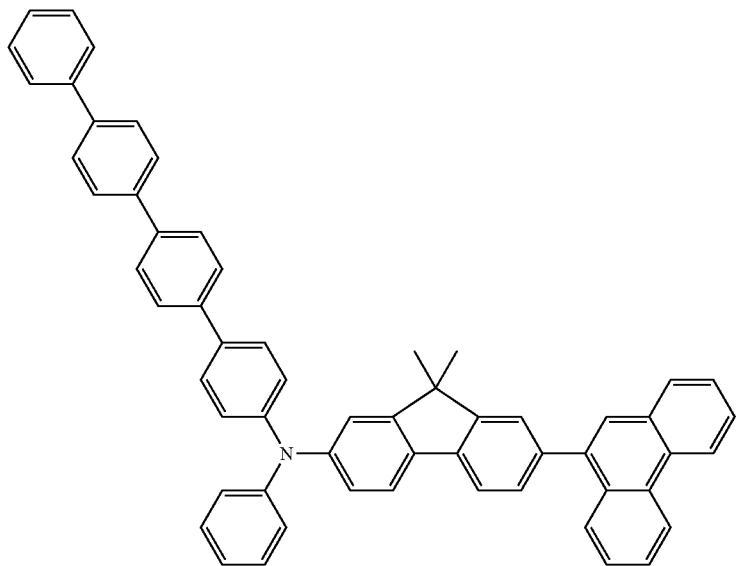
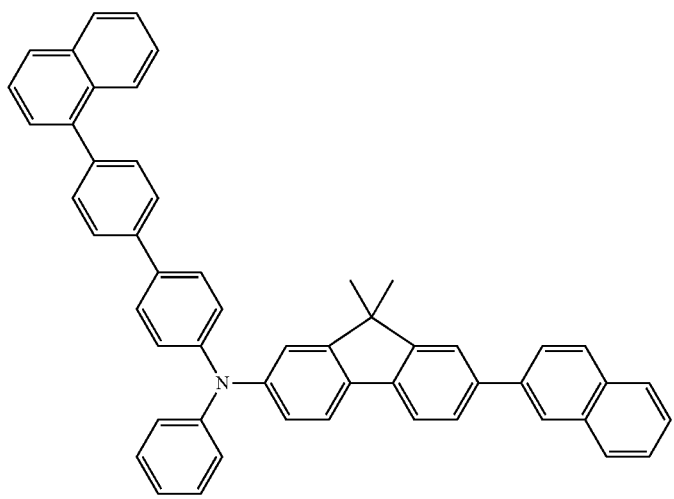
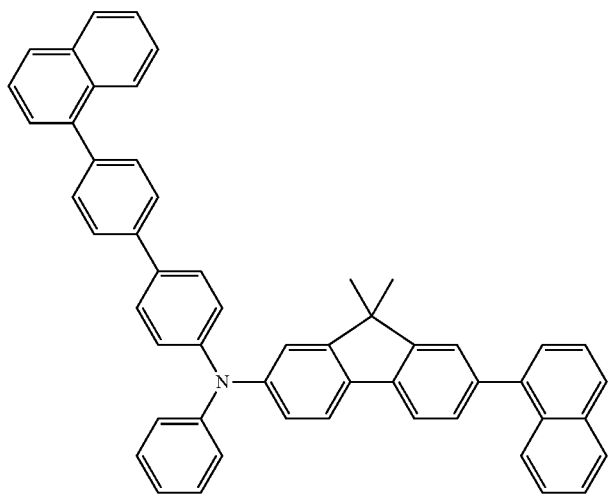

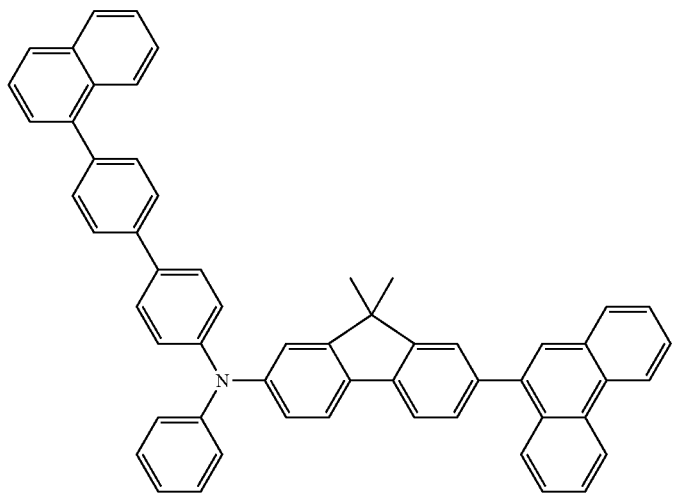
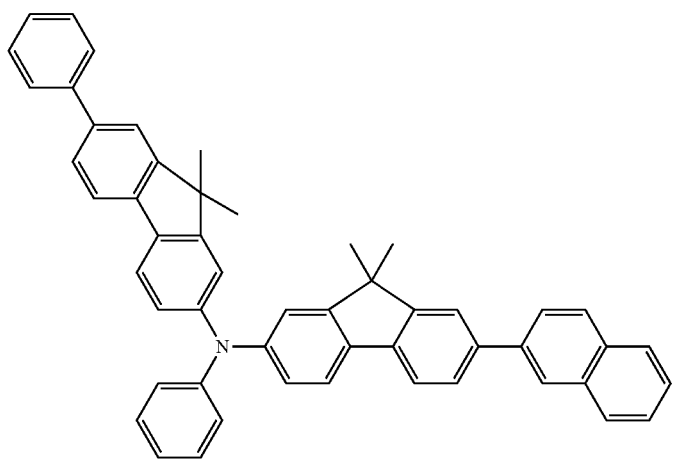
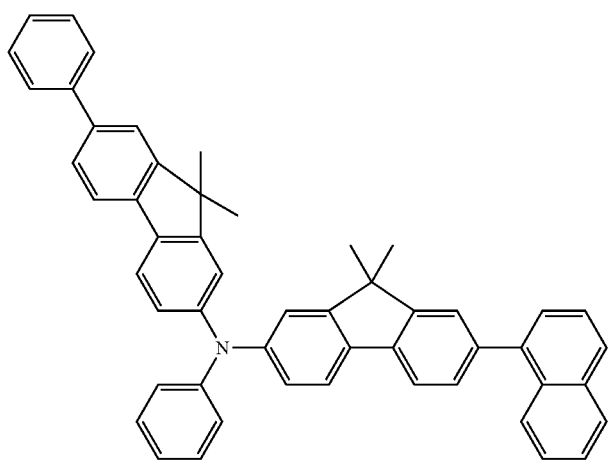

-continued
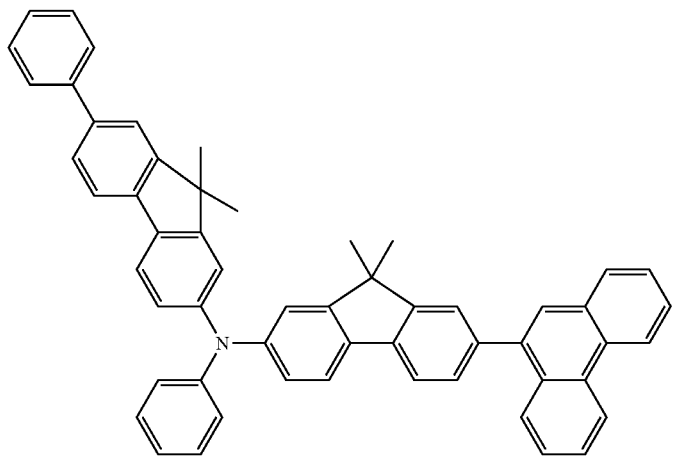
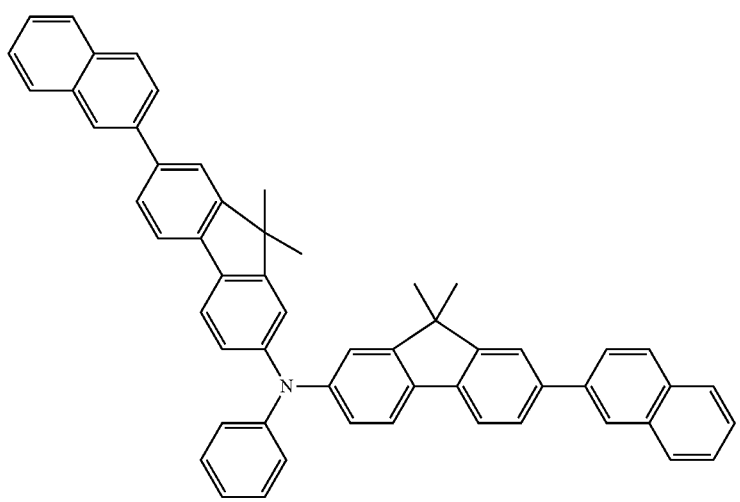
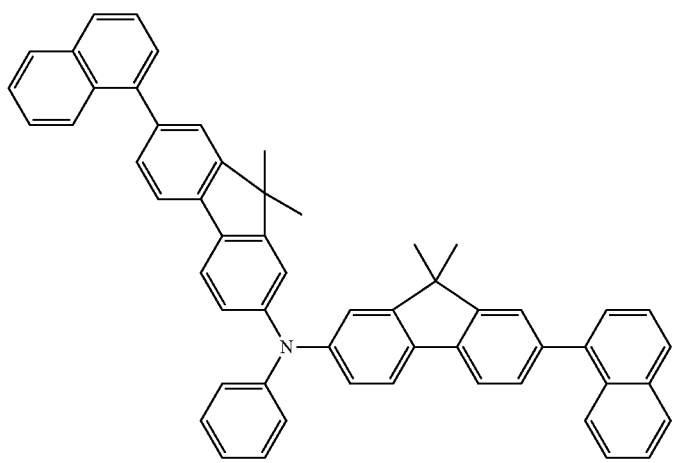

-continued
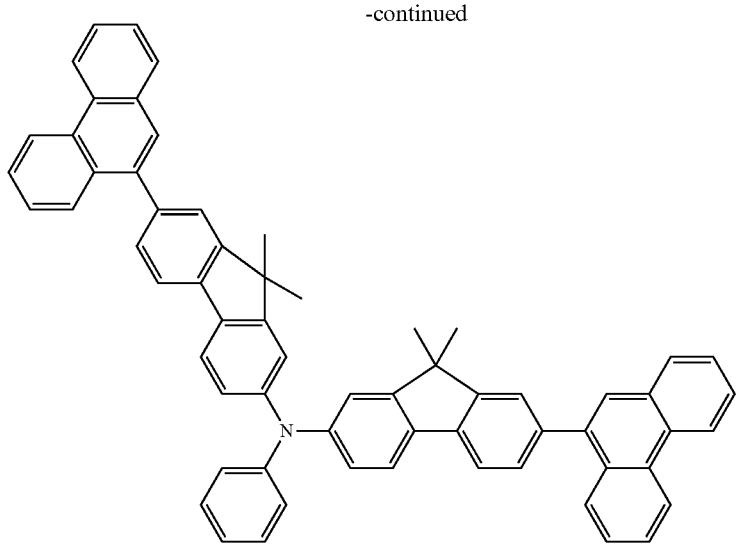
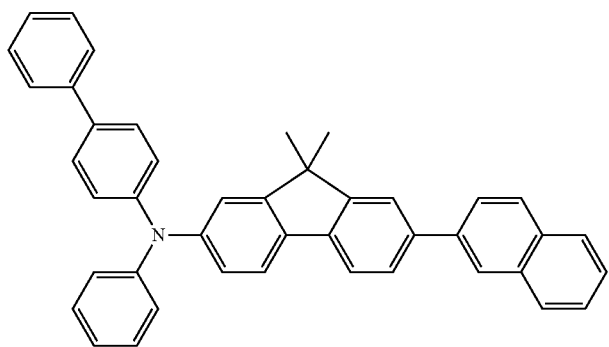
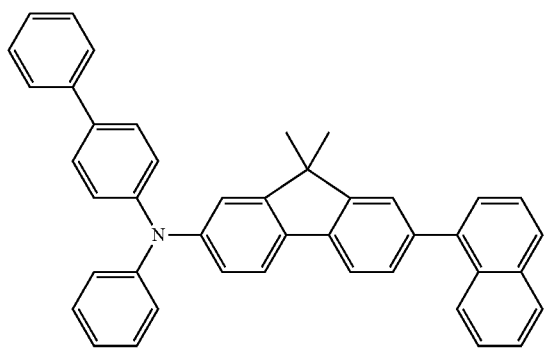
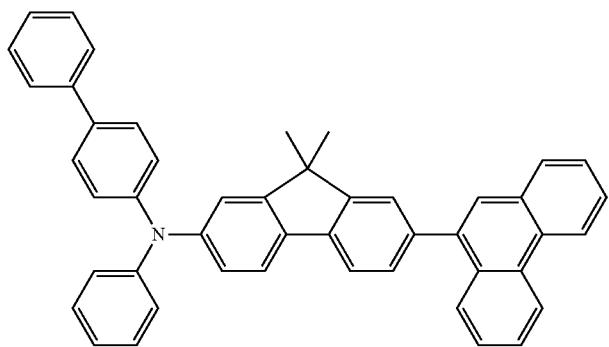

-continued
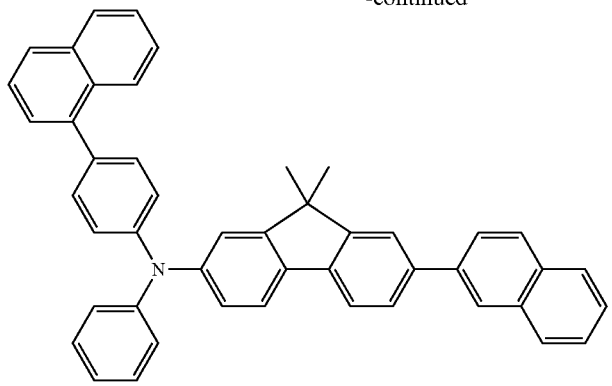
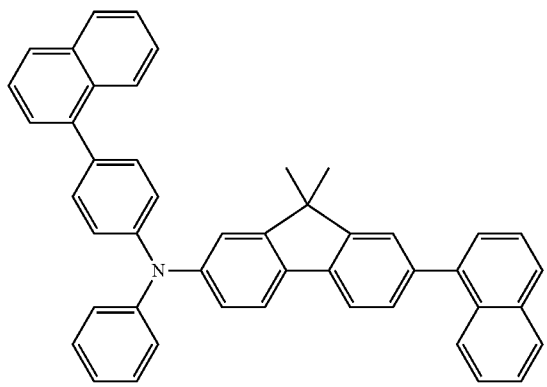
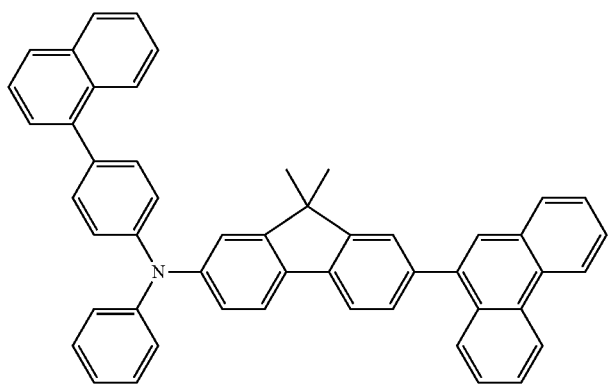
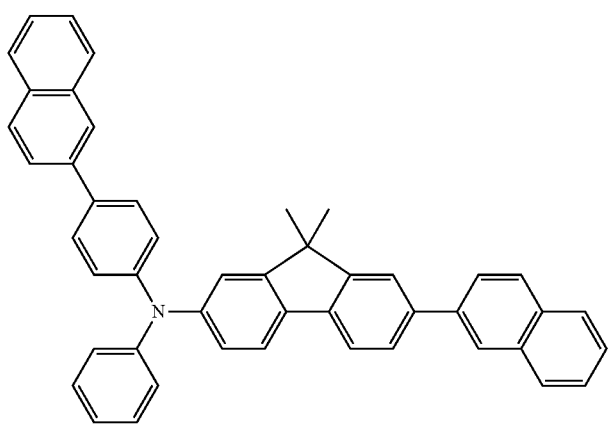

-continued
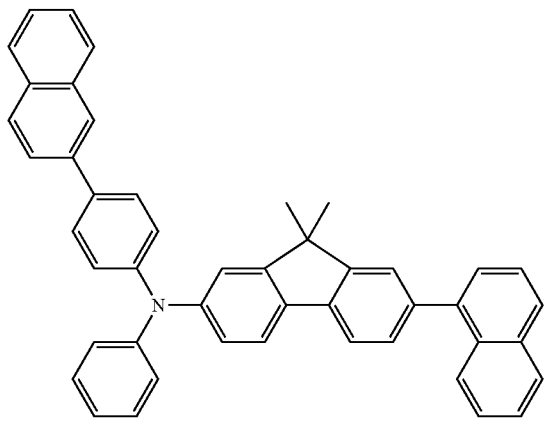
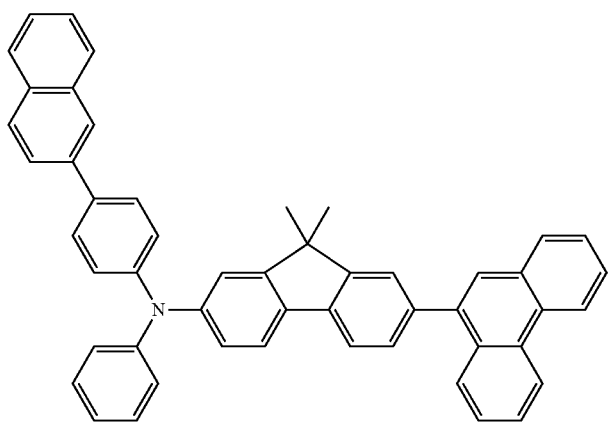
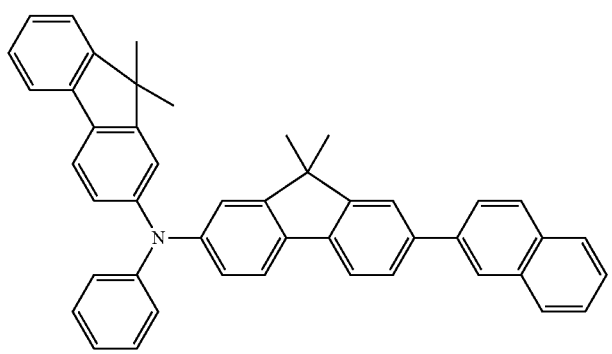
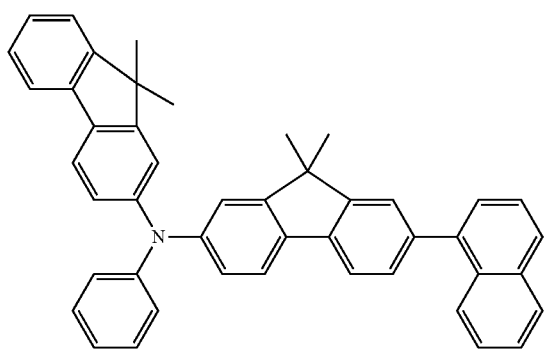

-continued
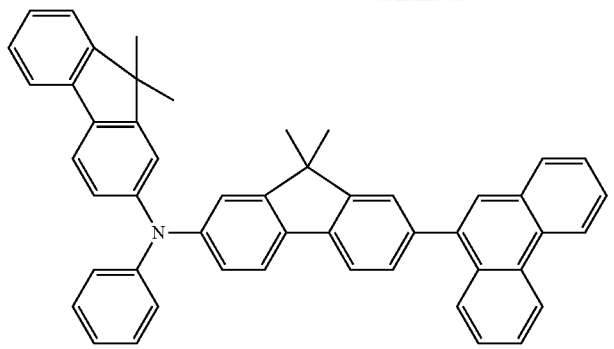
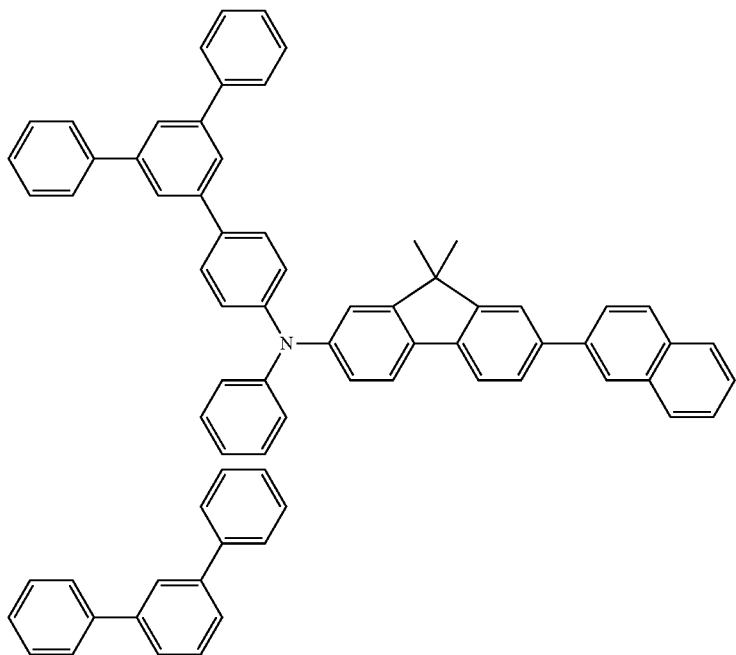
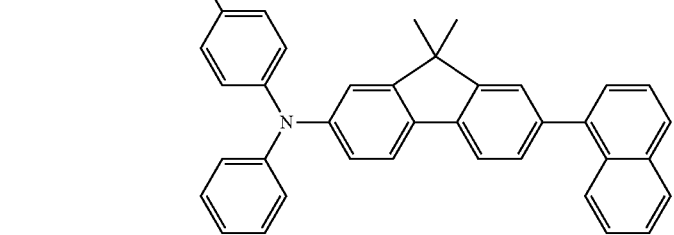
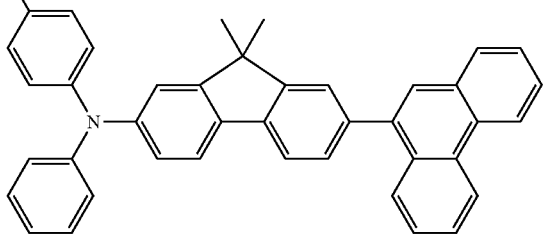

-continued
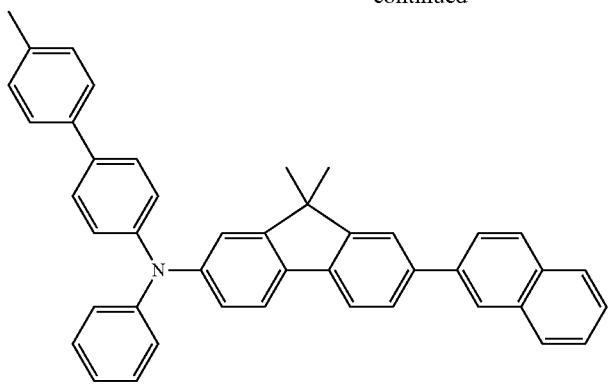
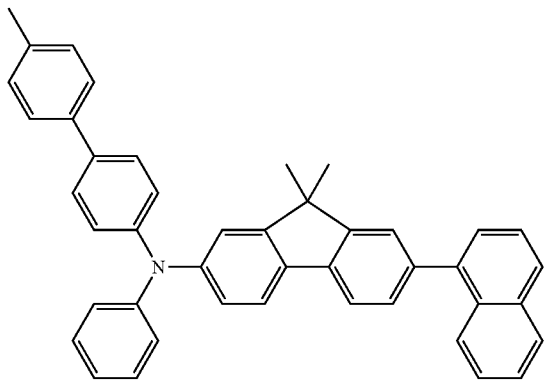
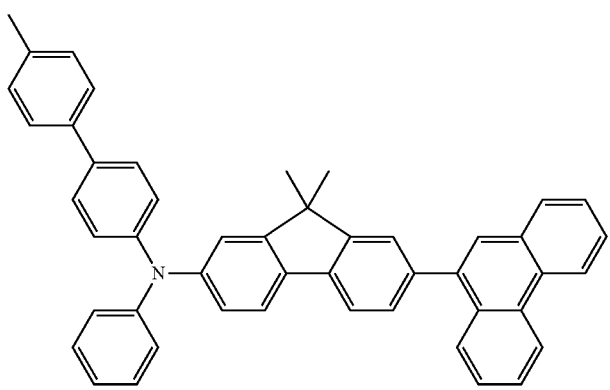
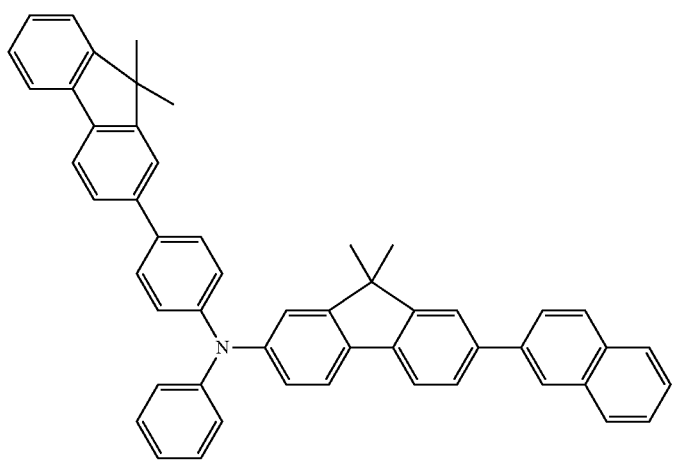

-continued
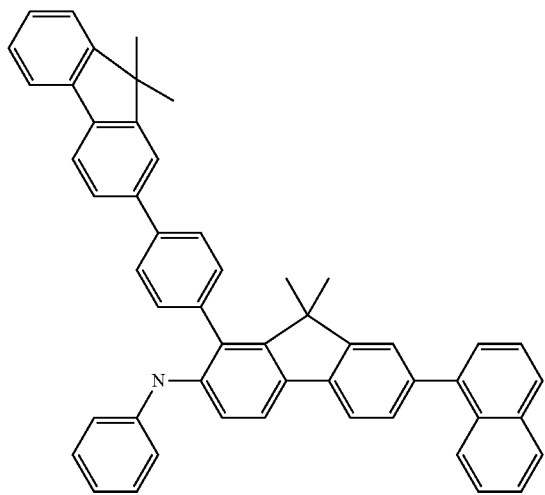
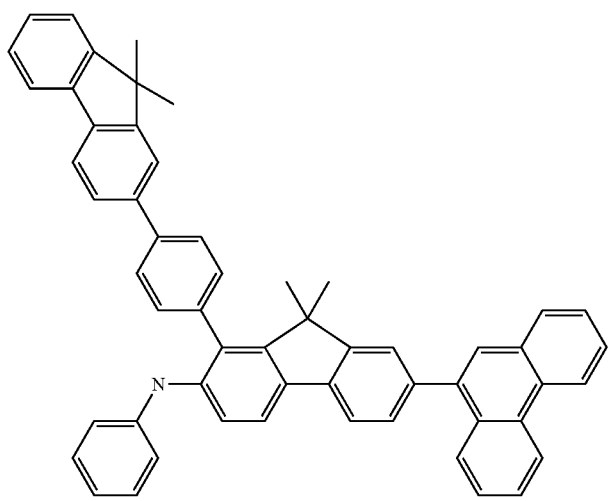
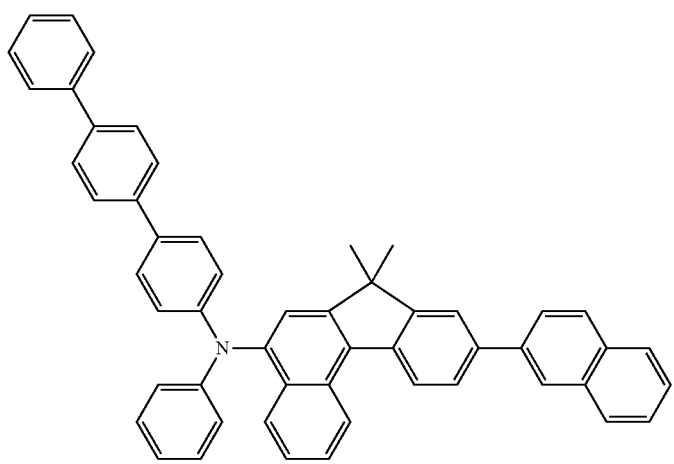

-continued
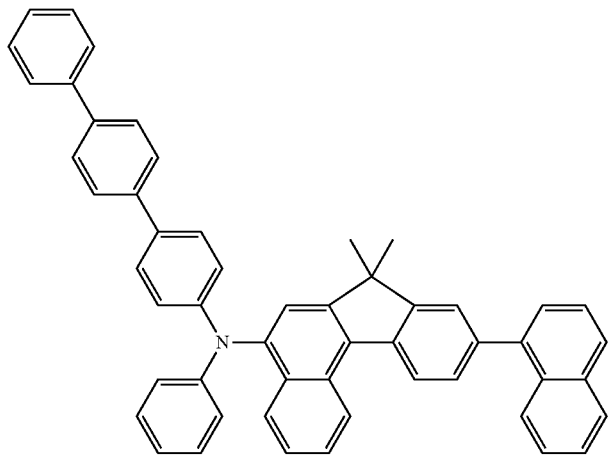
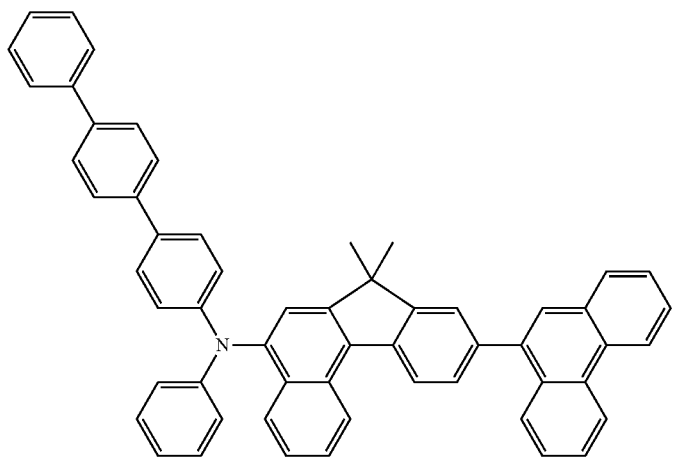
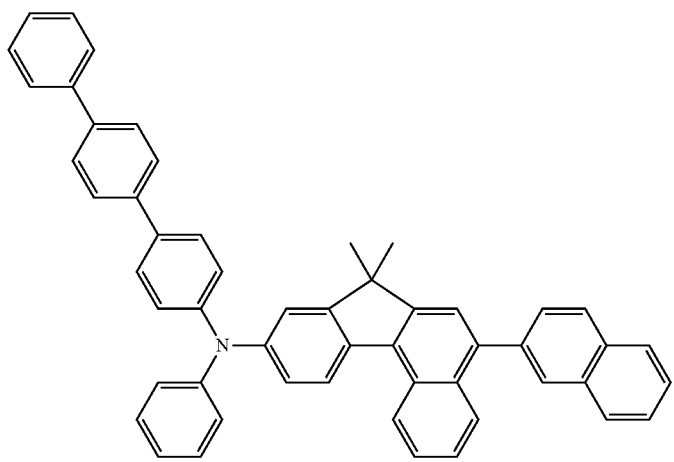

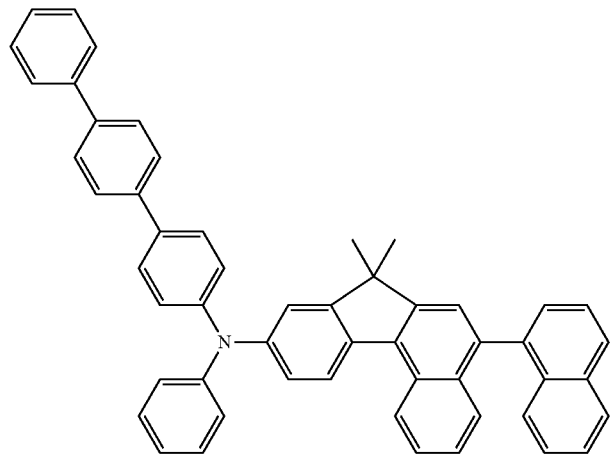
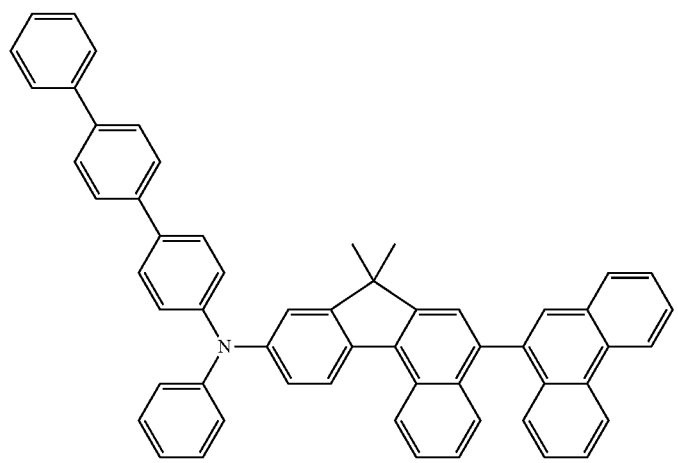
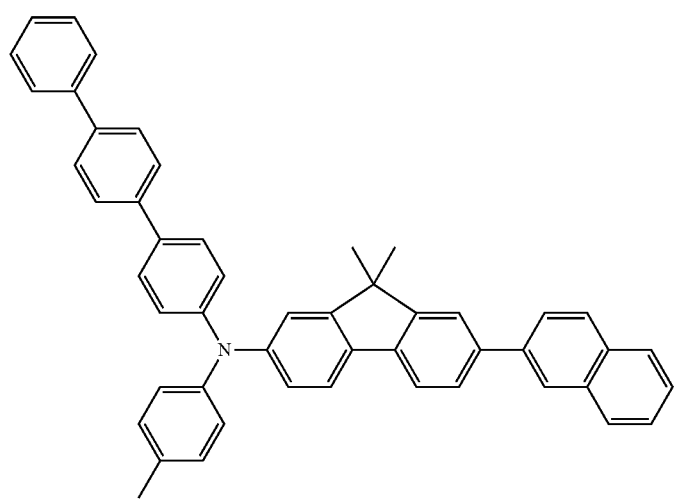

-continued
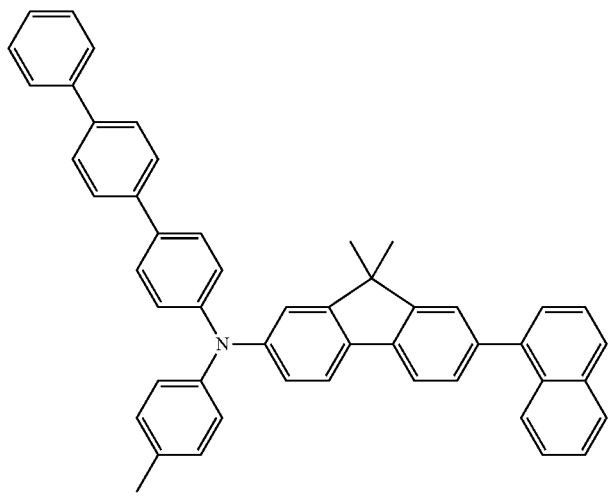
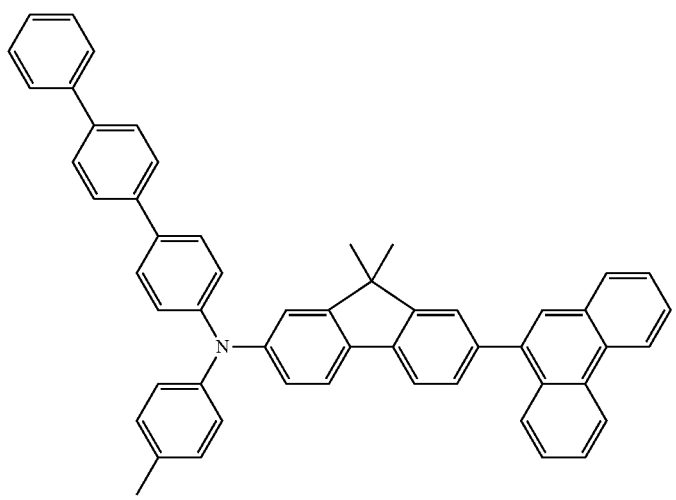
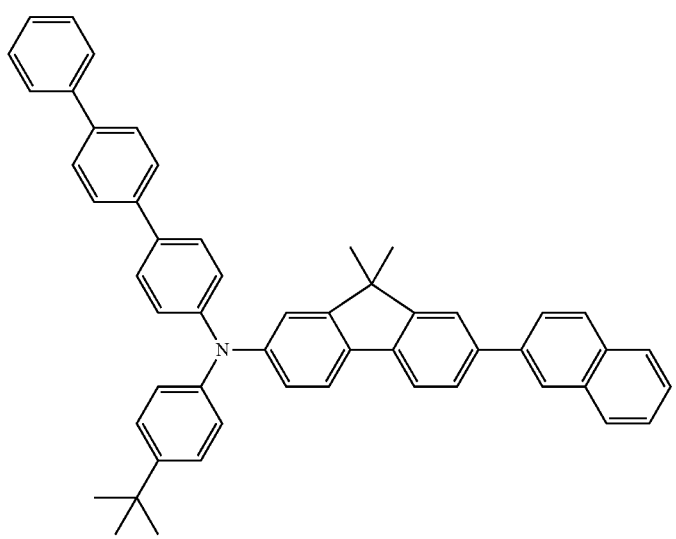

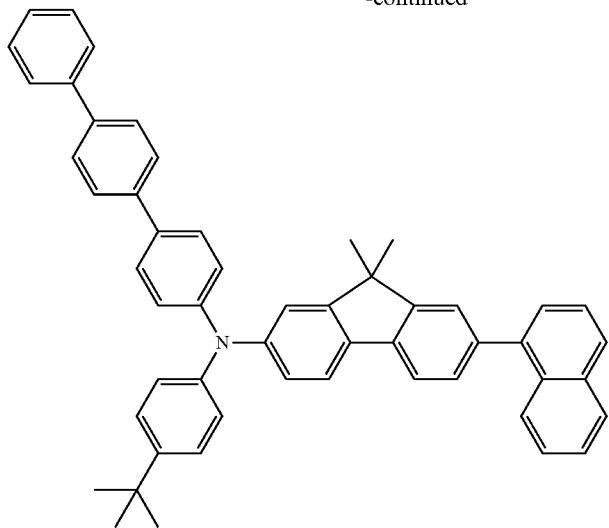
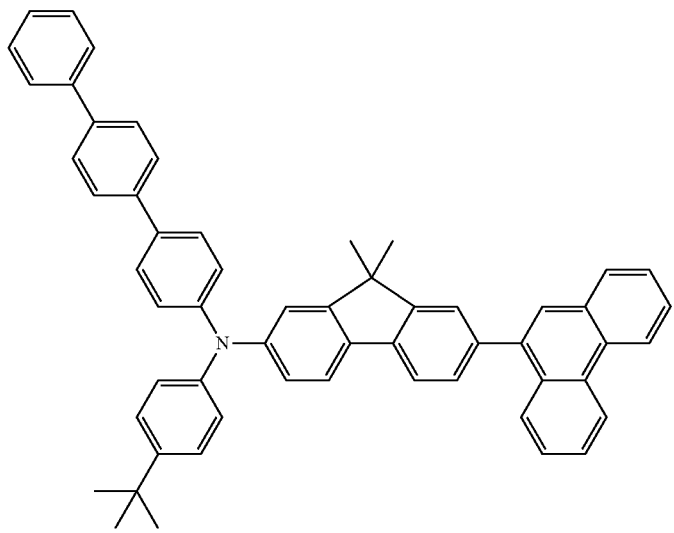
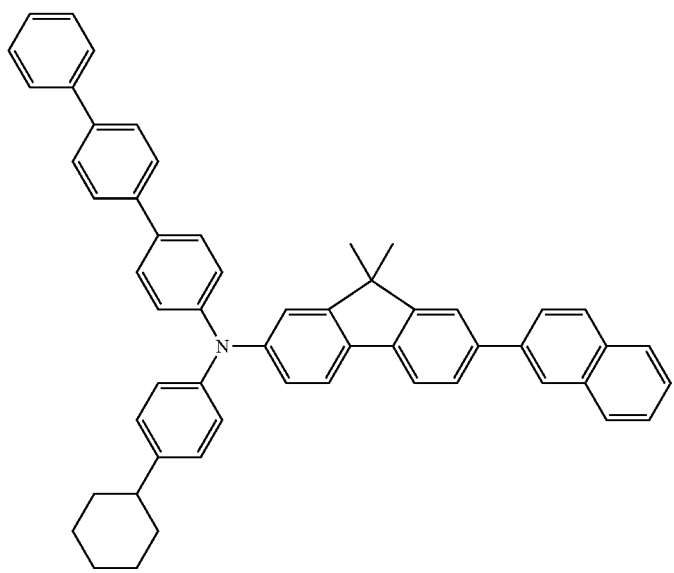

-continued
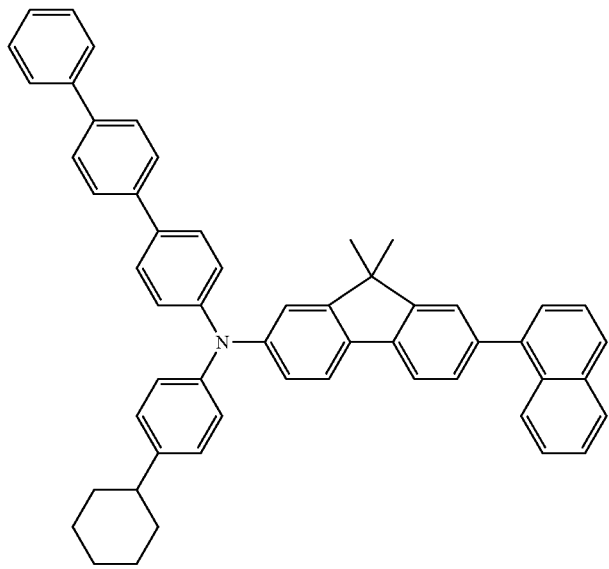
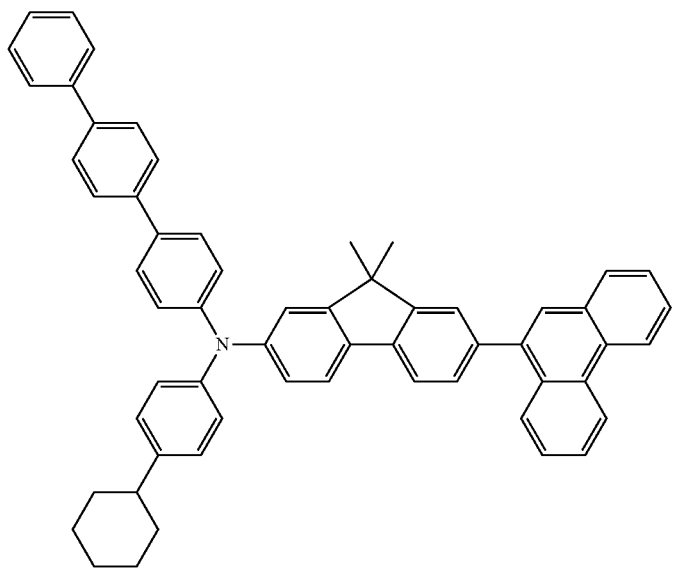
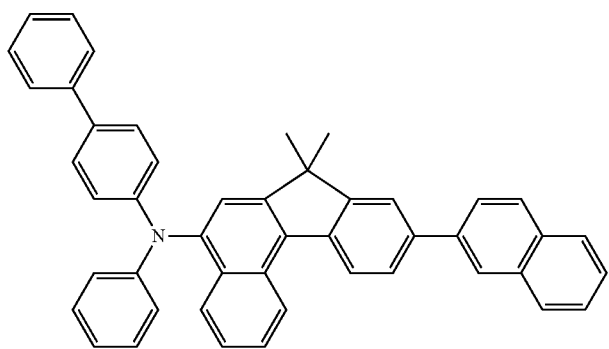

-continued
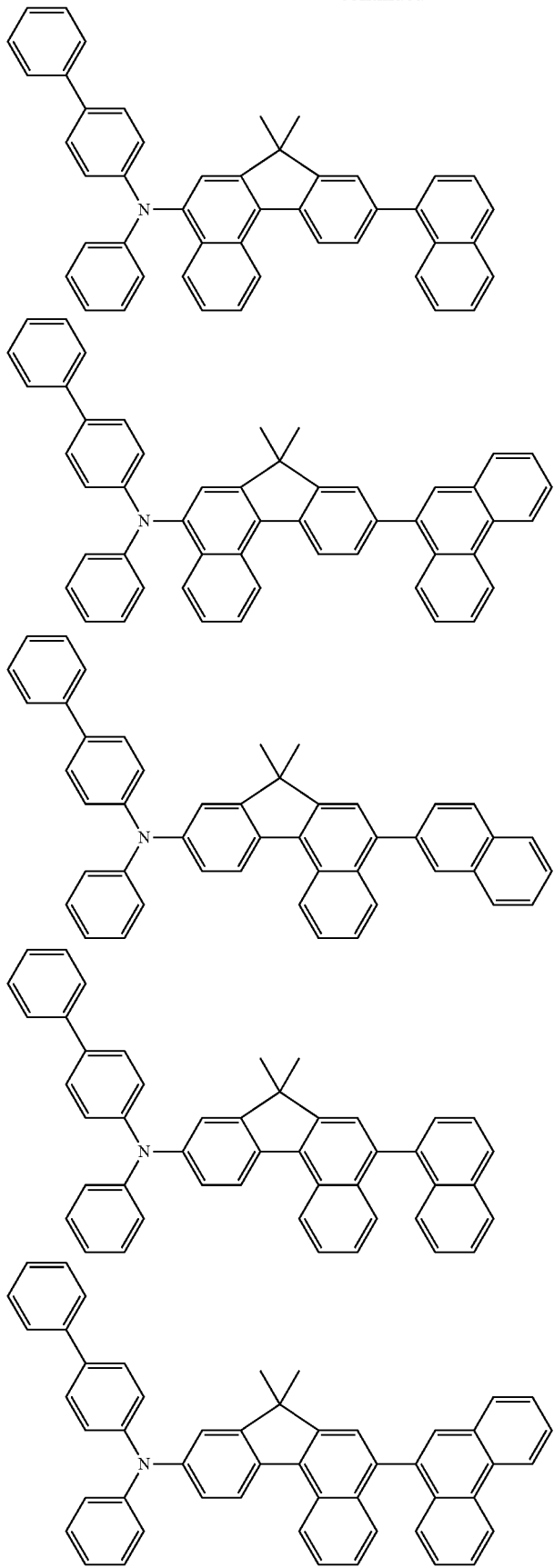

-continued
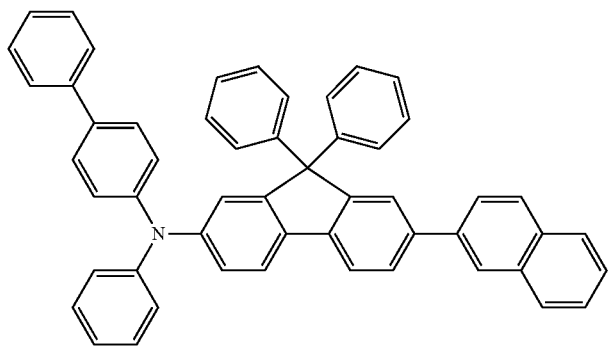
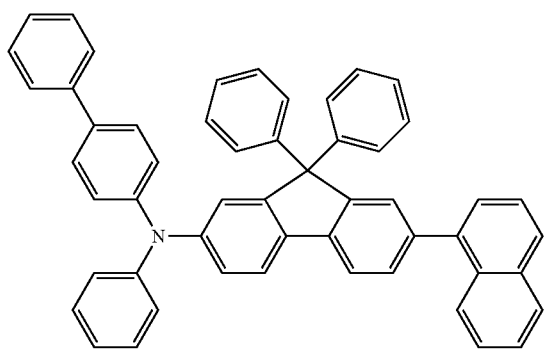
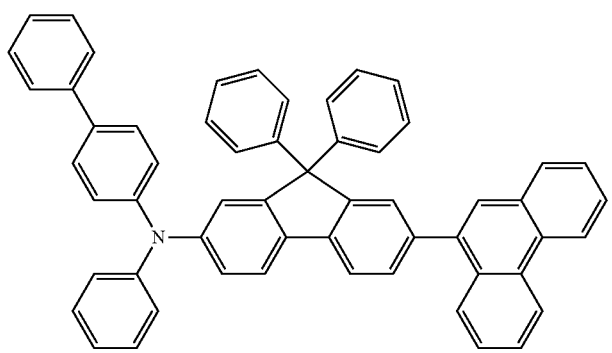
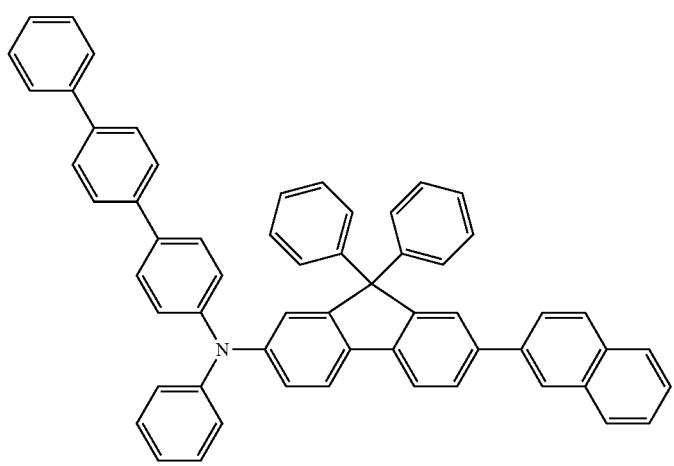

-continued
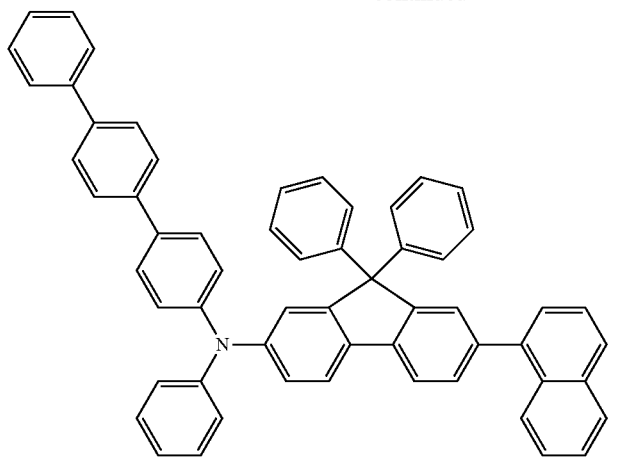
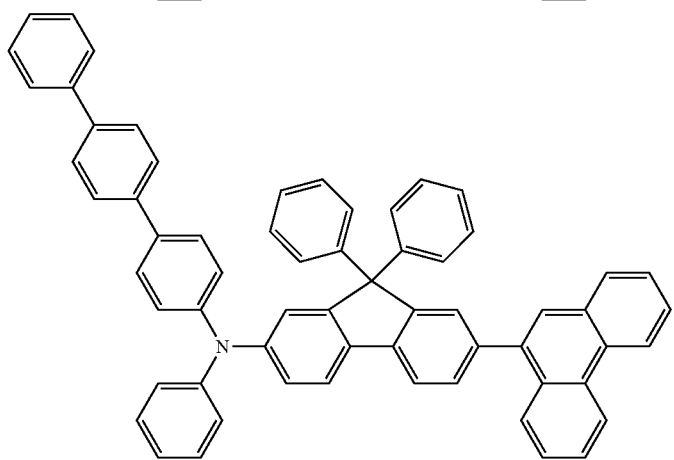
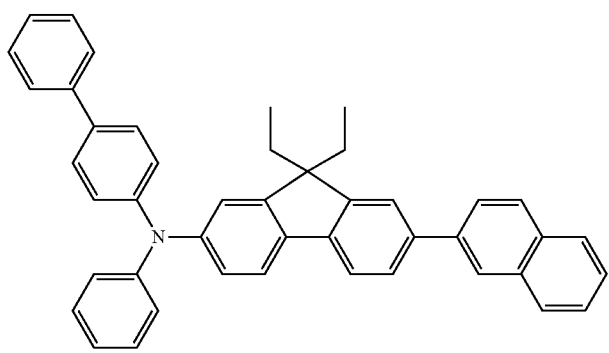
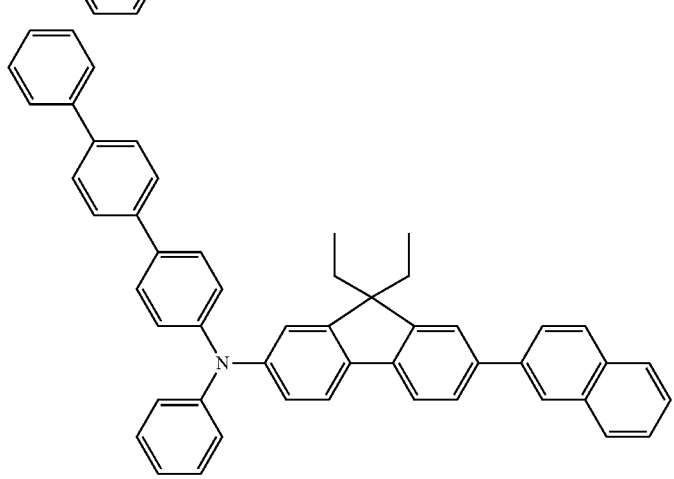

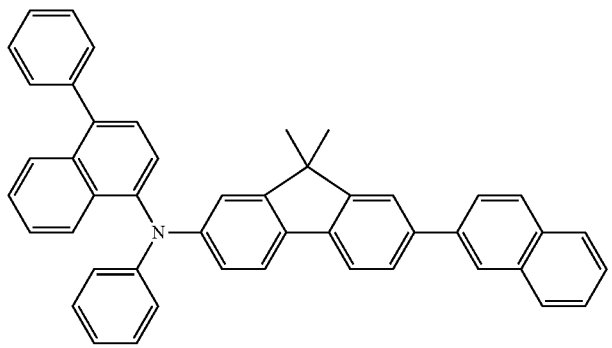
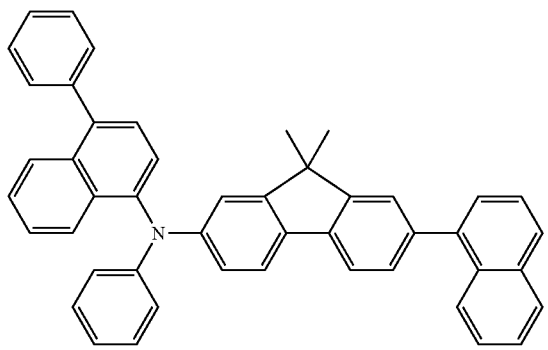
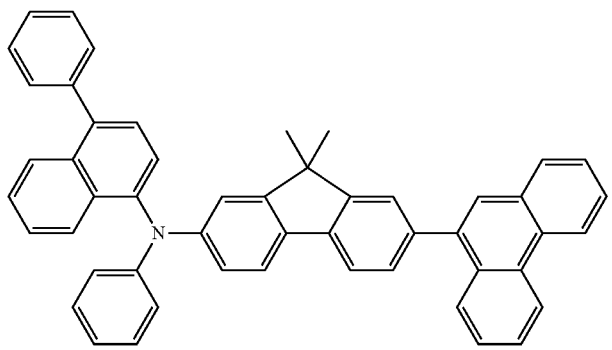
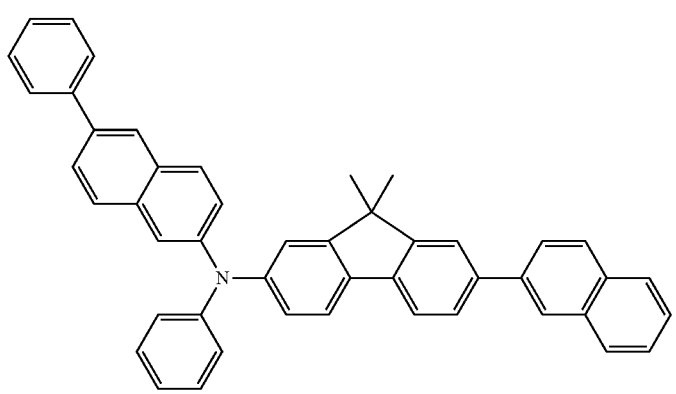

-continued
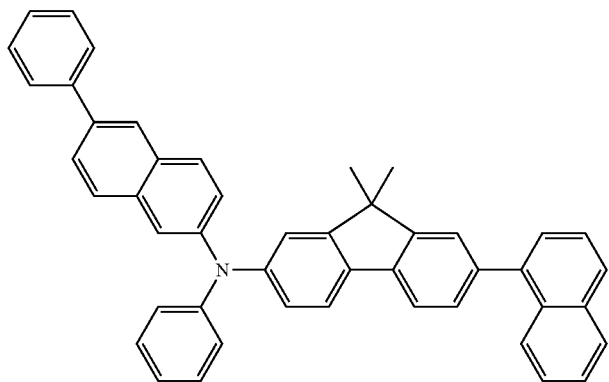
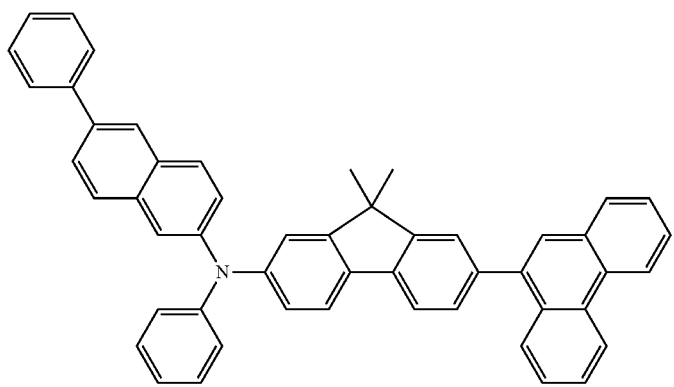
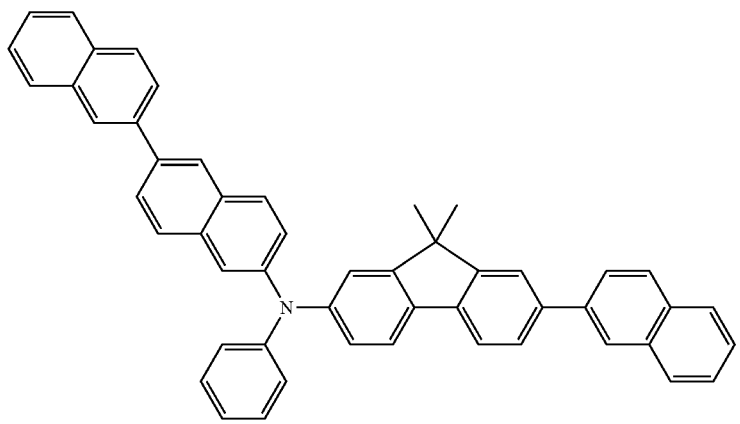
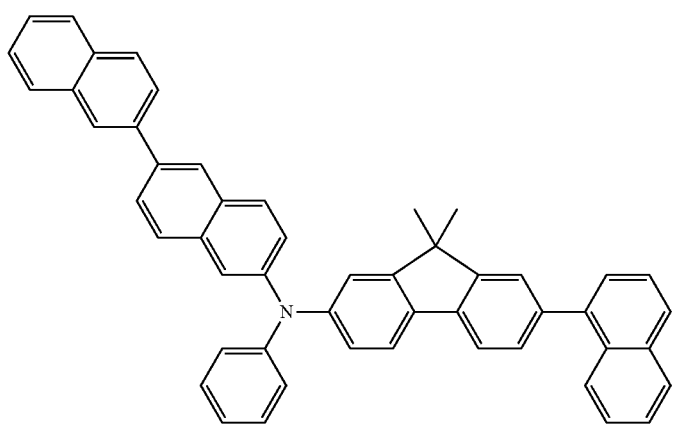

-continued
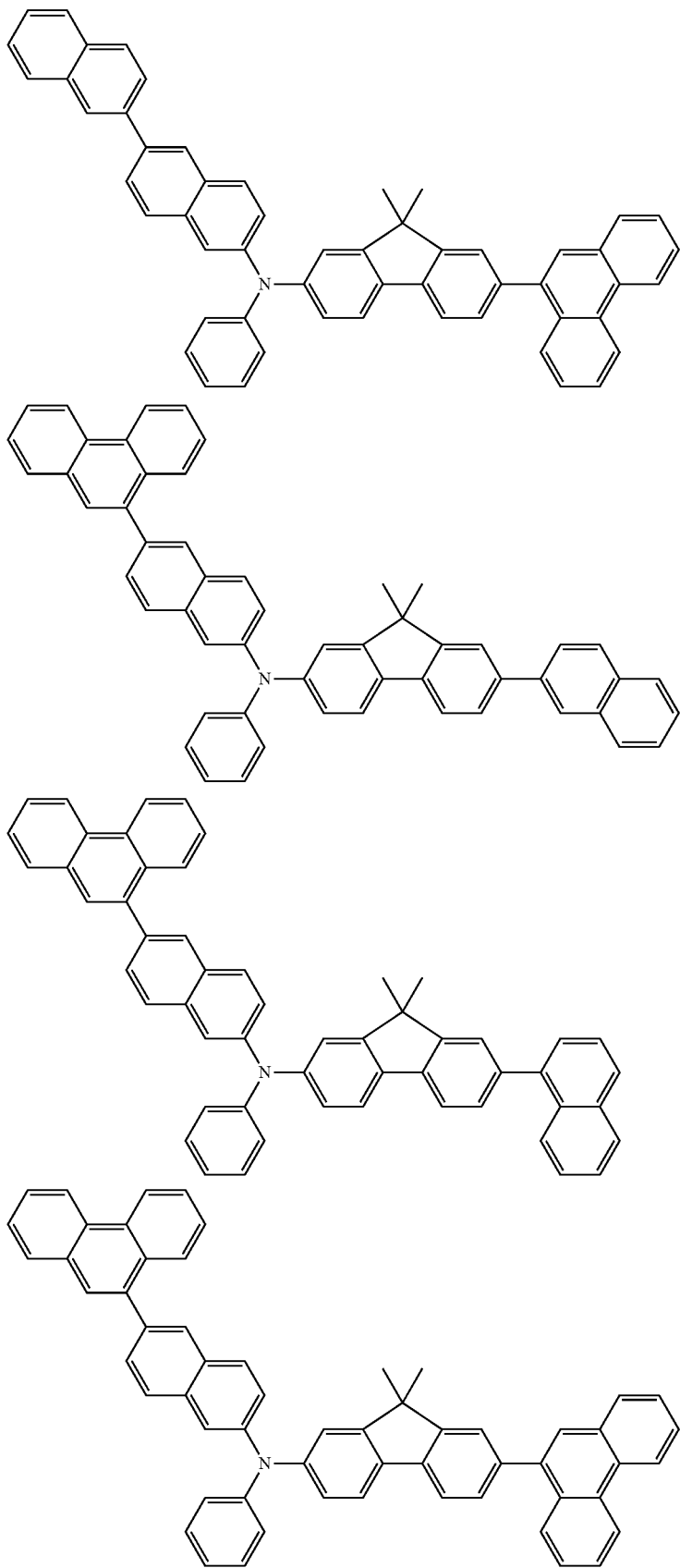

-continued
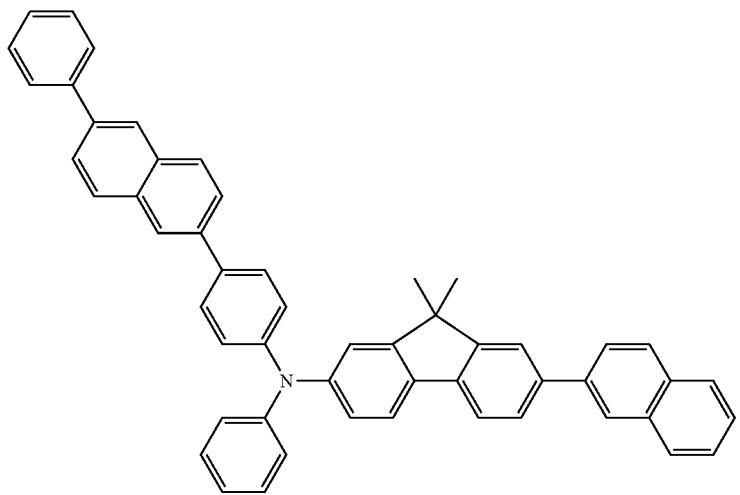
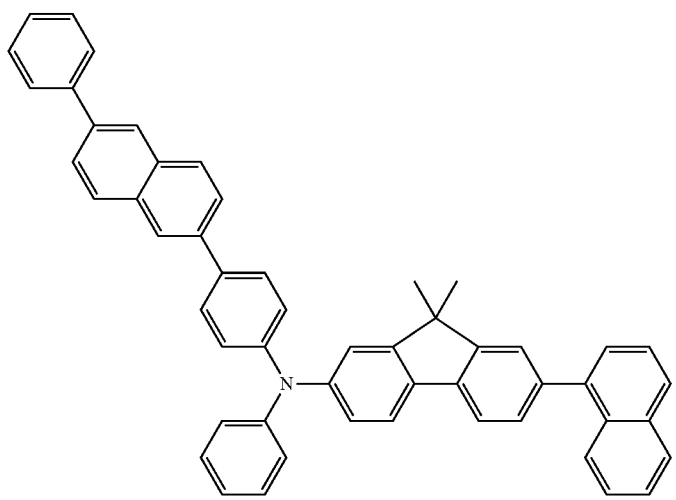
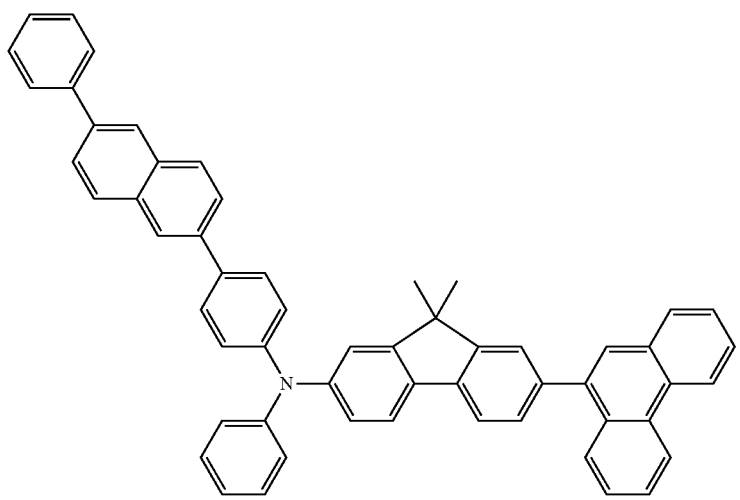

-continued
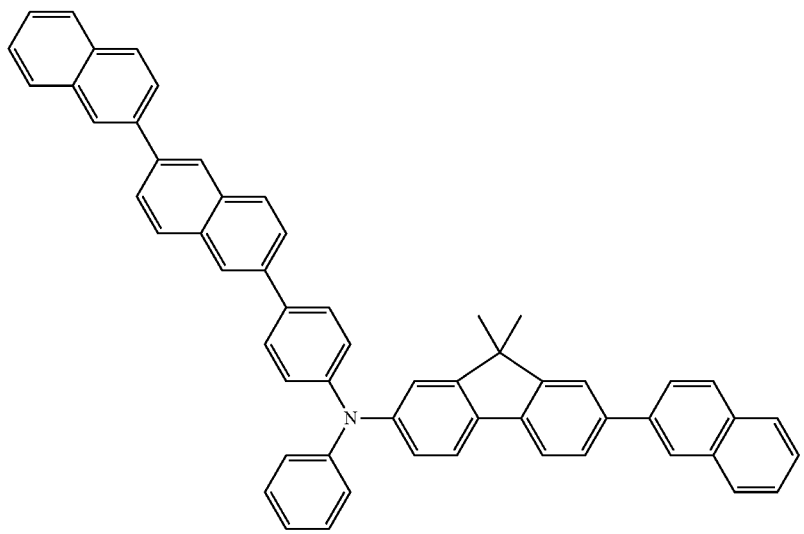
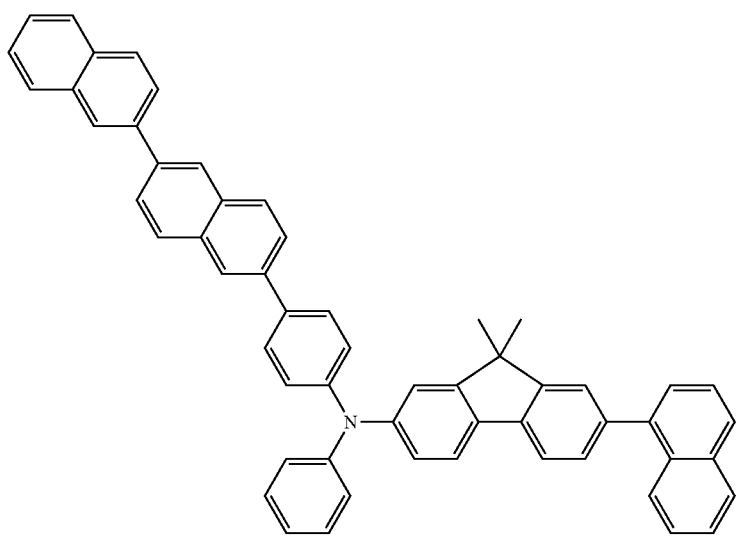
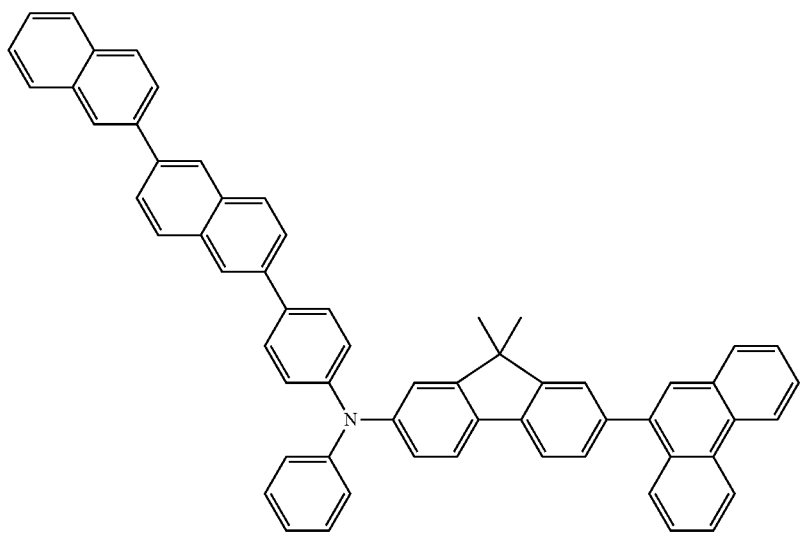

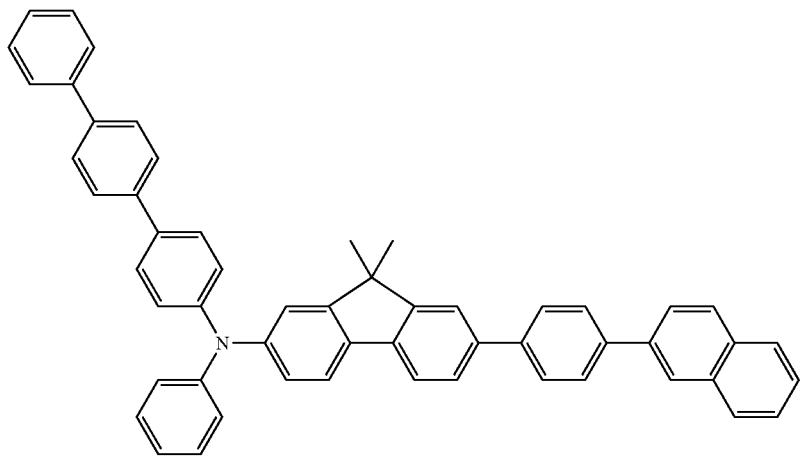
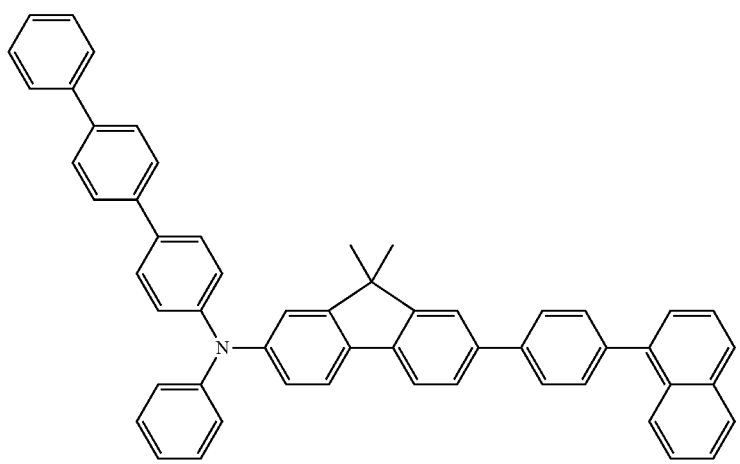
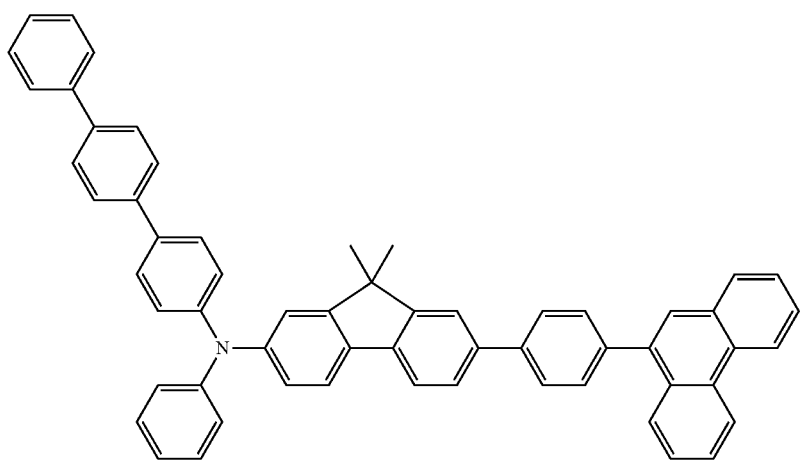

-continued
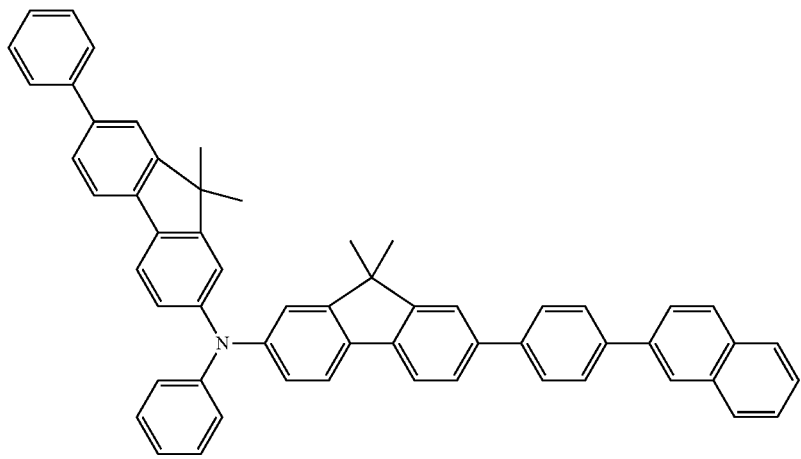
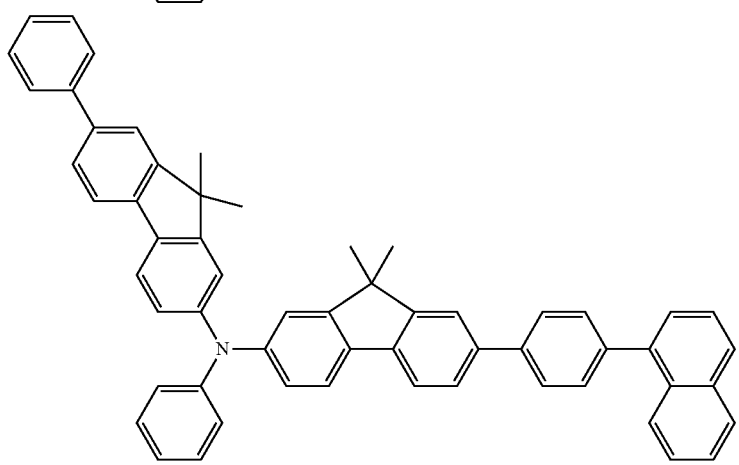
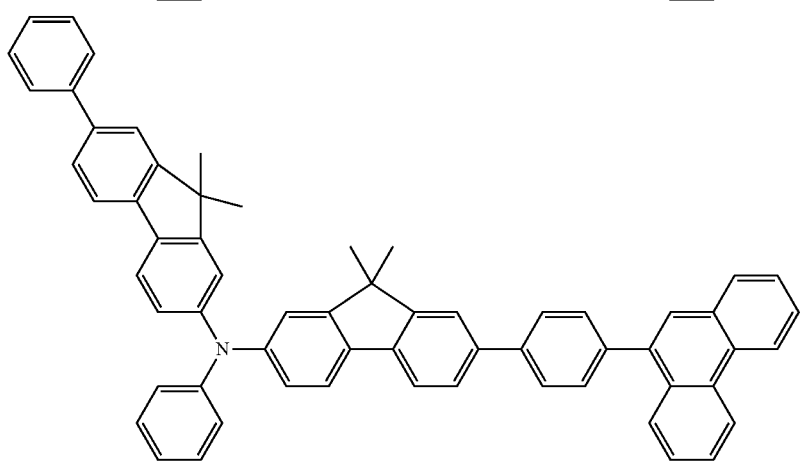
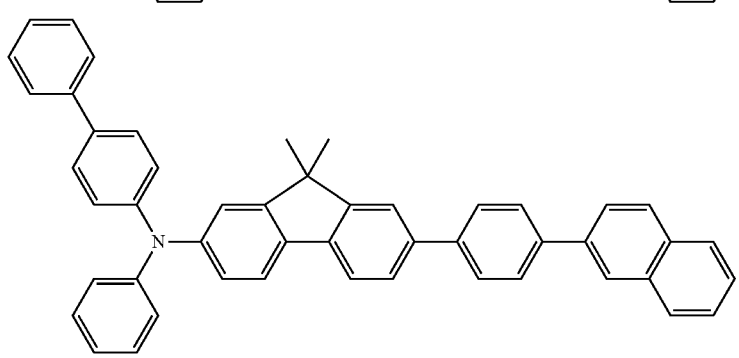

-continued
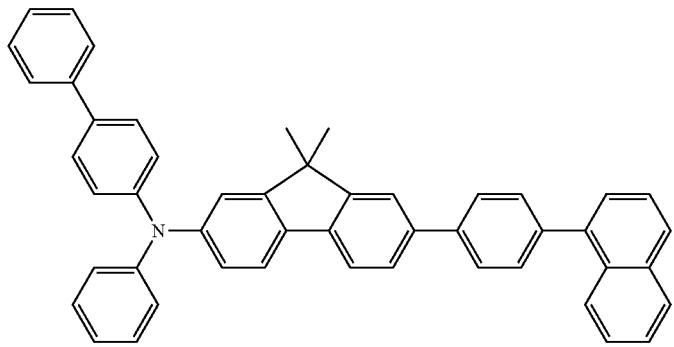
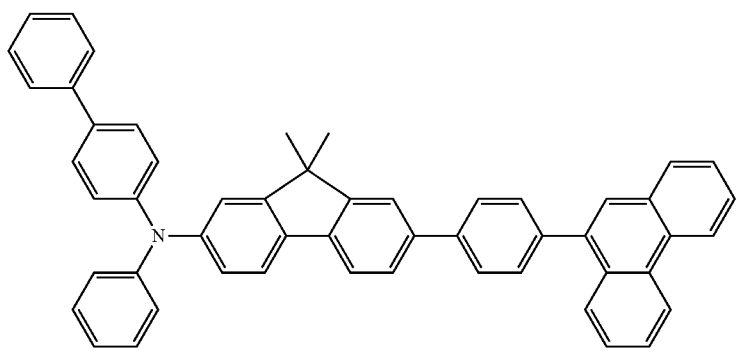
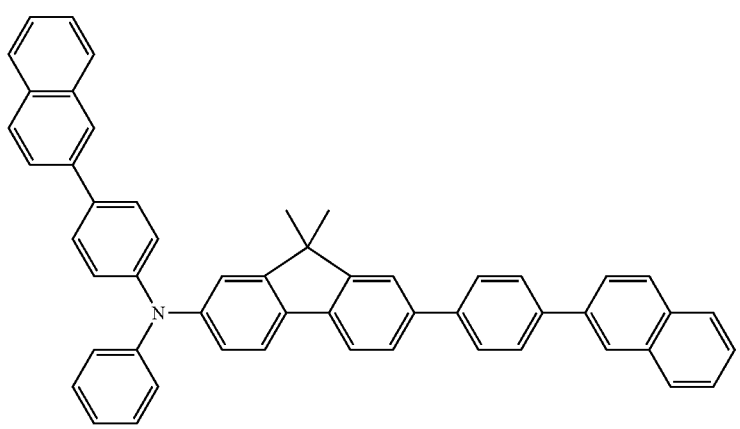
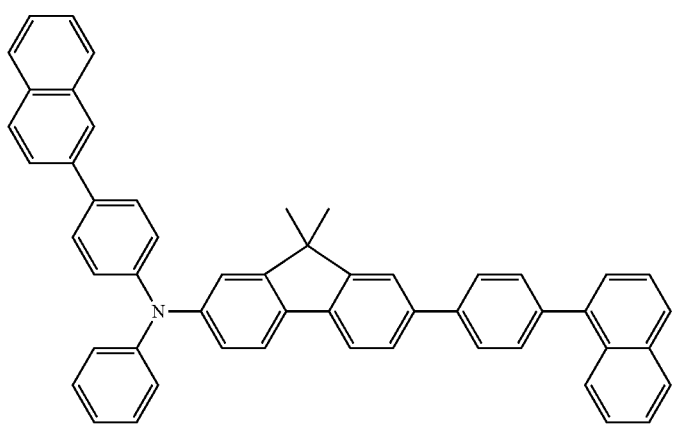

-continued
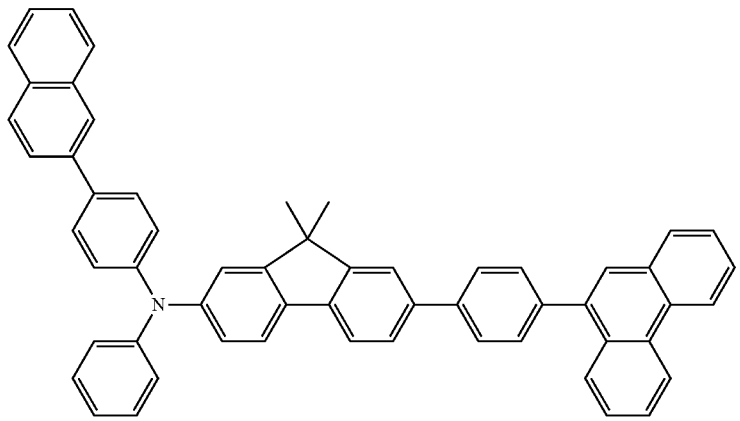
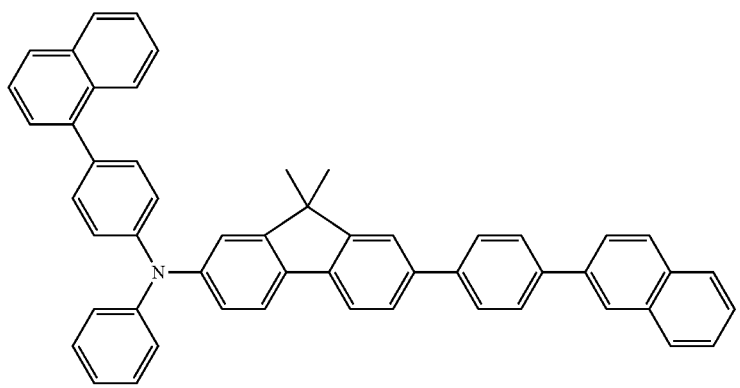
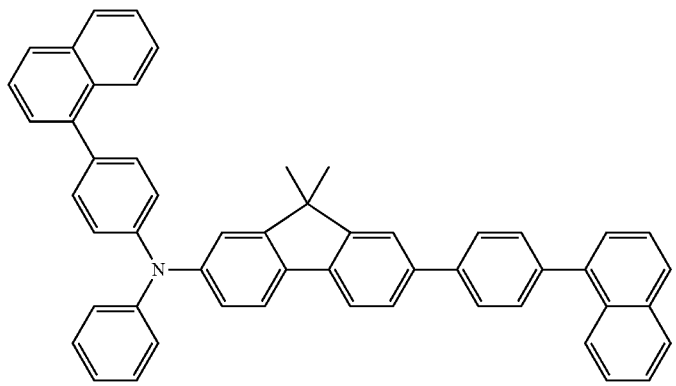
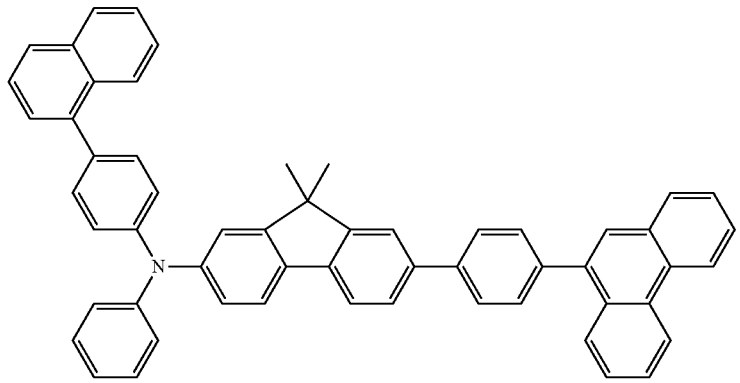

-continued
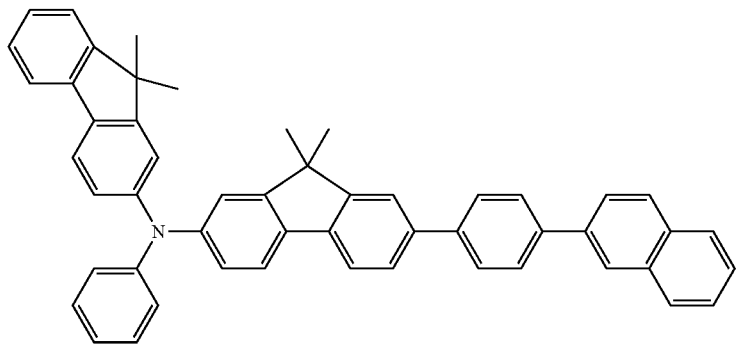
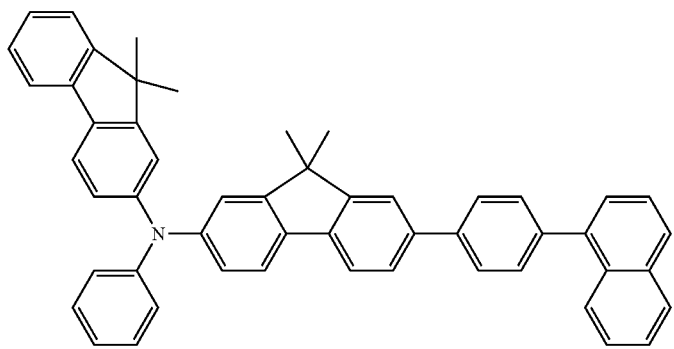
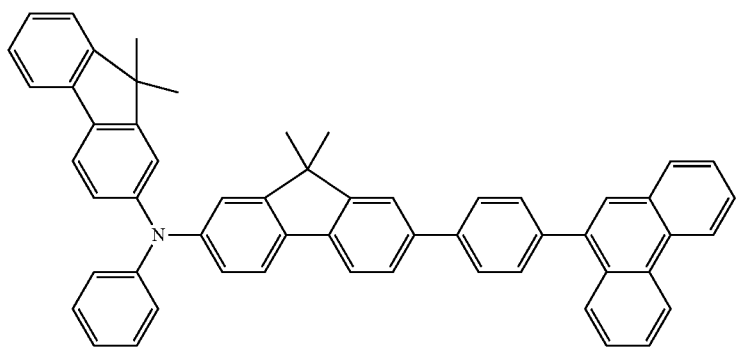
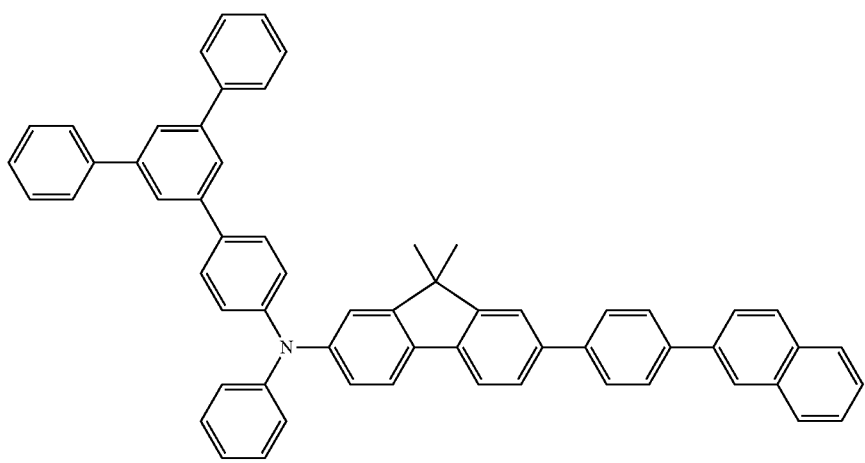

-continued
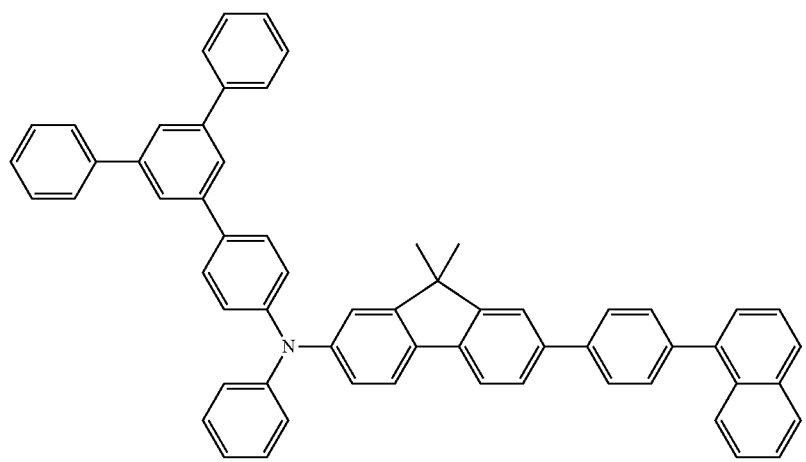
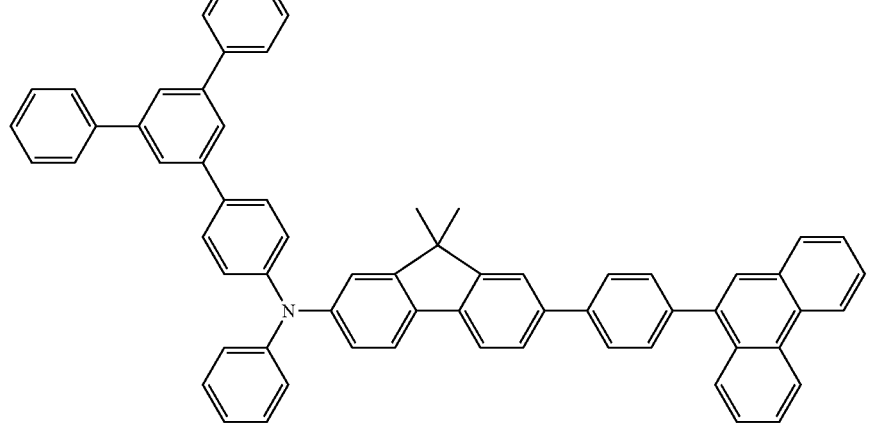
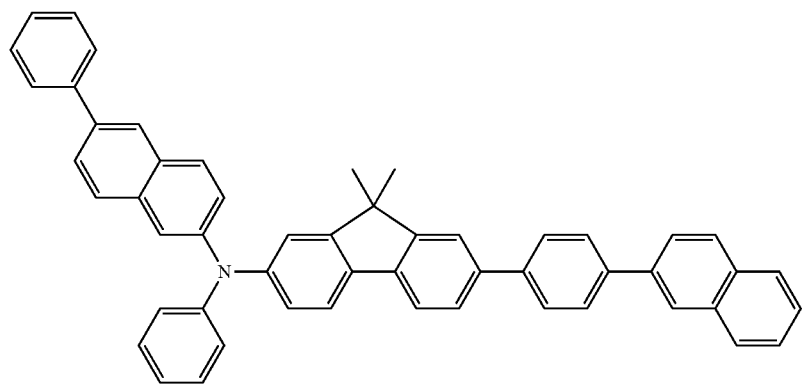
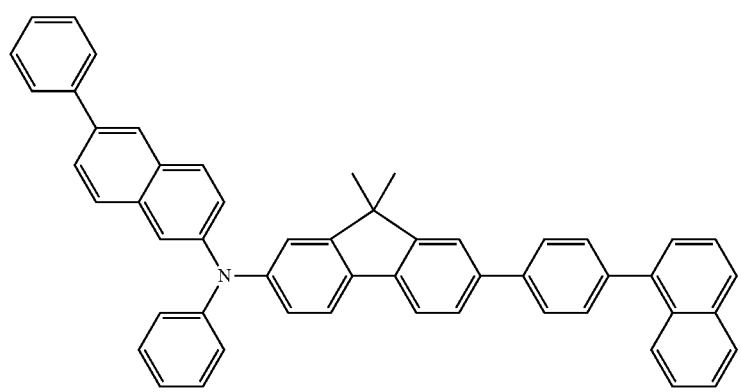

-continued
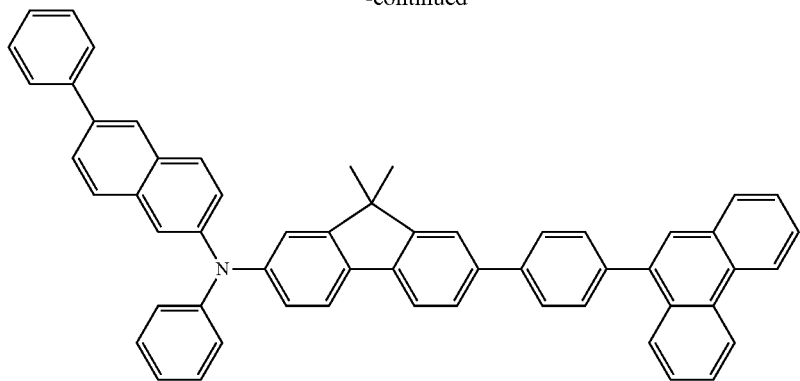
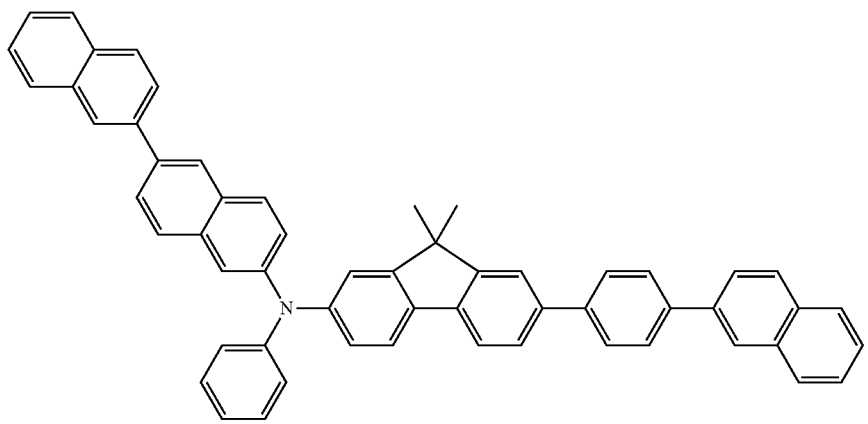
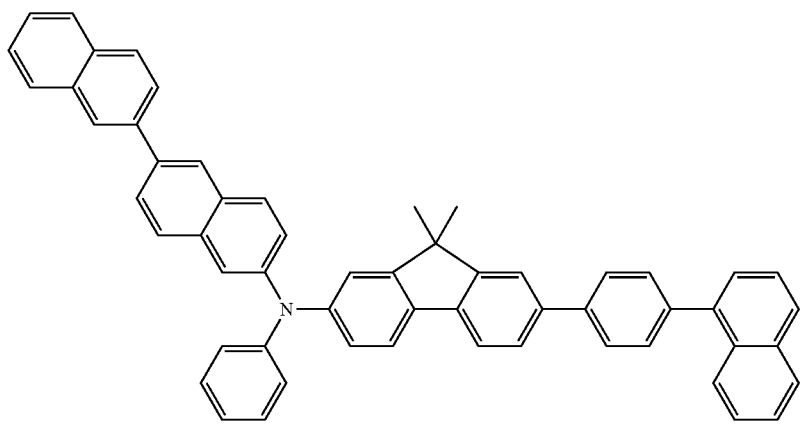
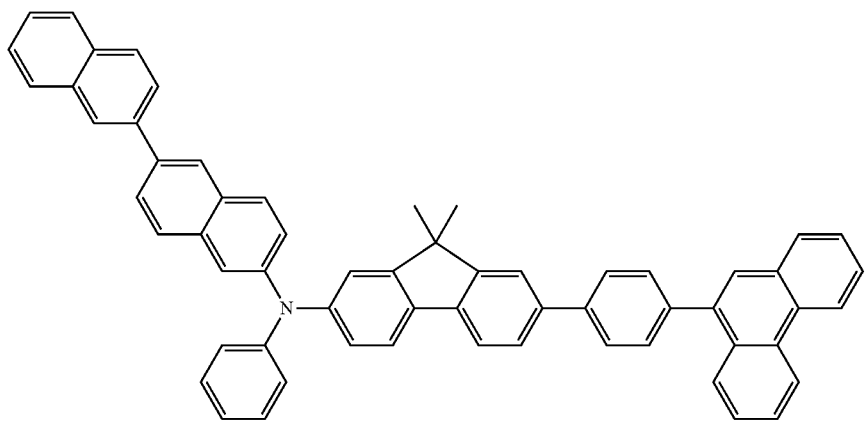

-continued
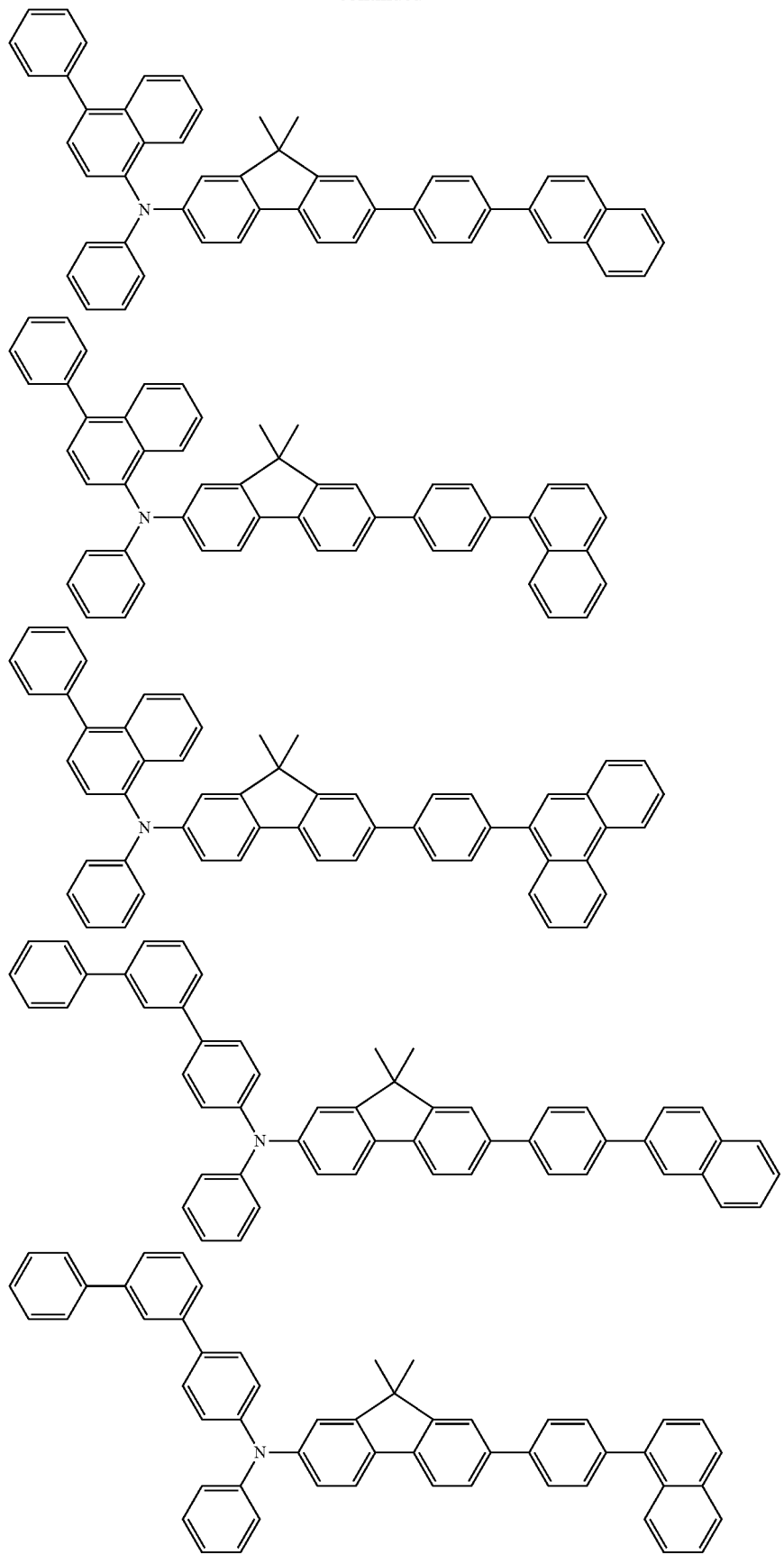

-continued
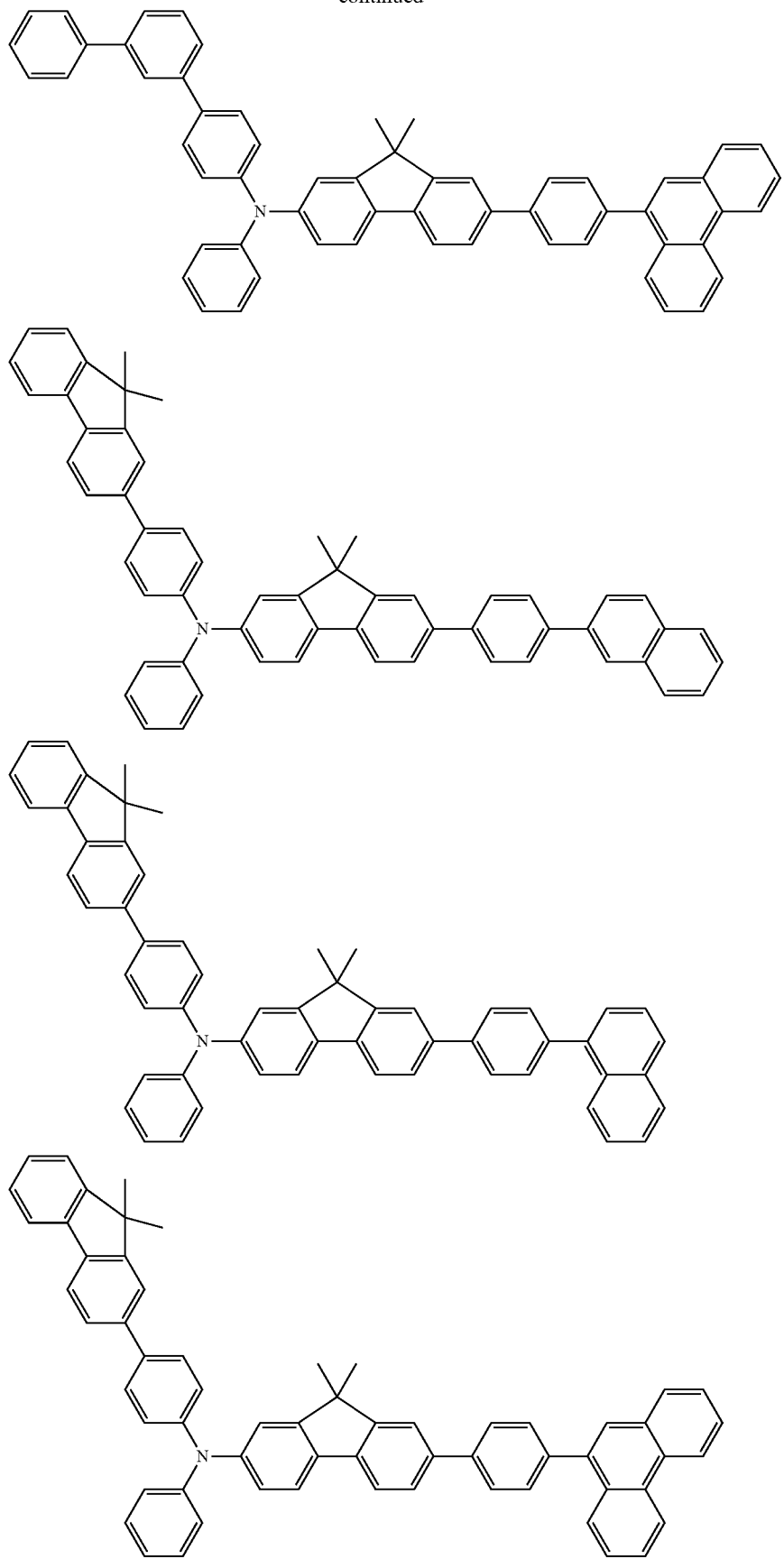

-continued
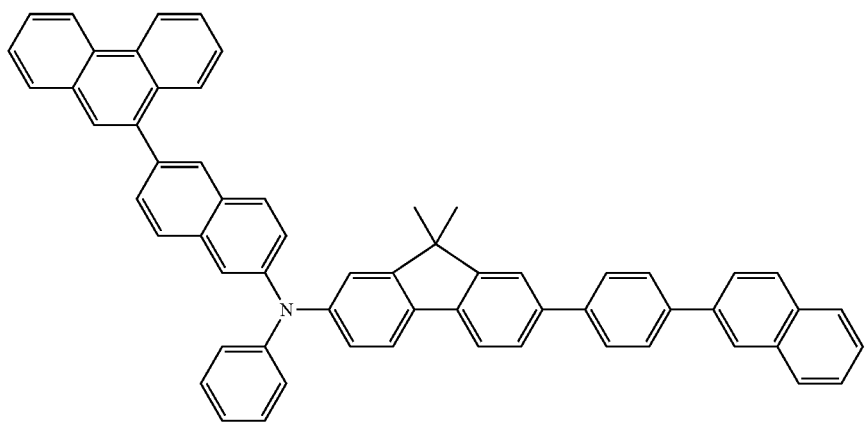
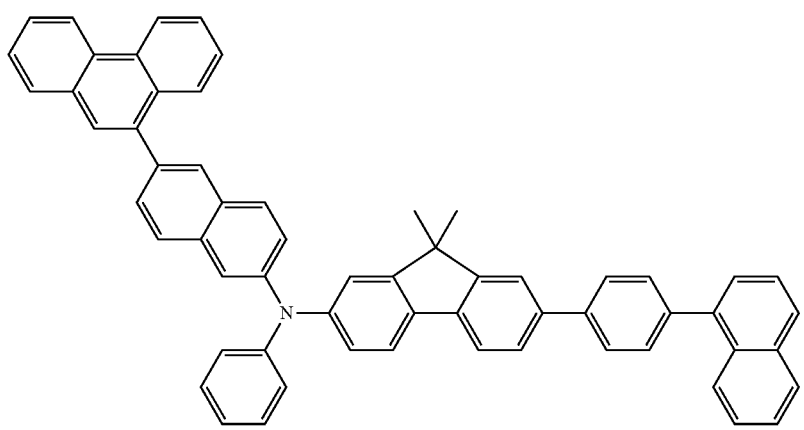
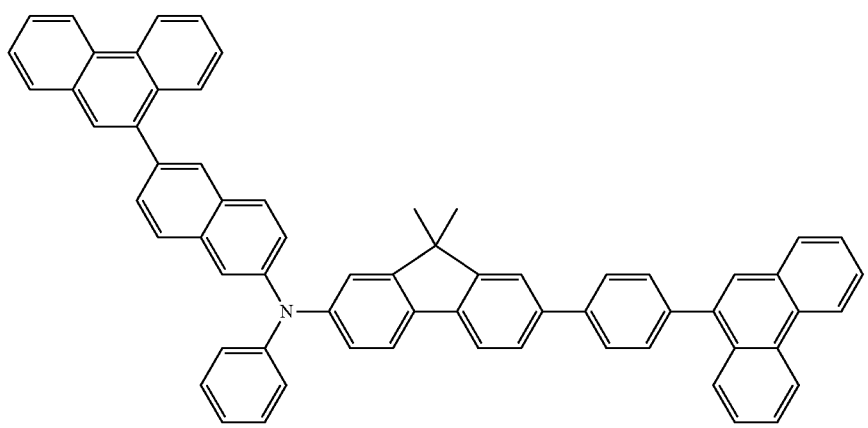
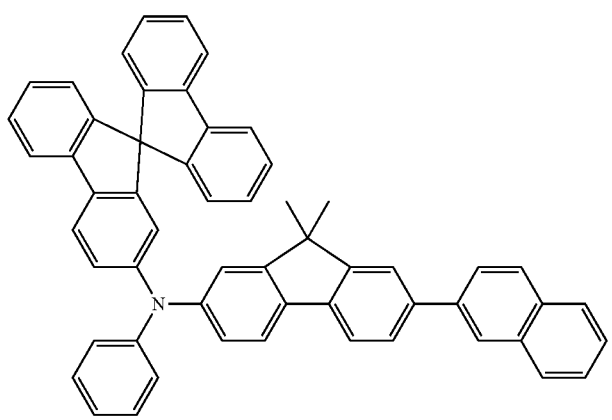

-continued
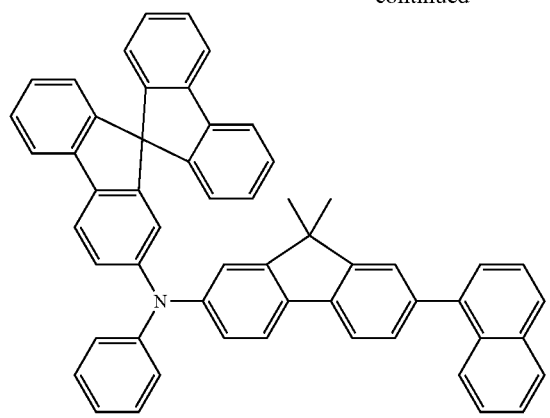
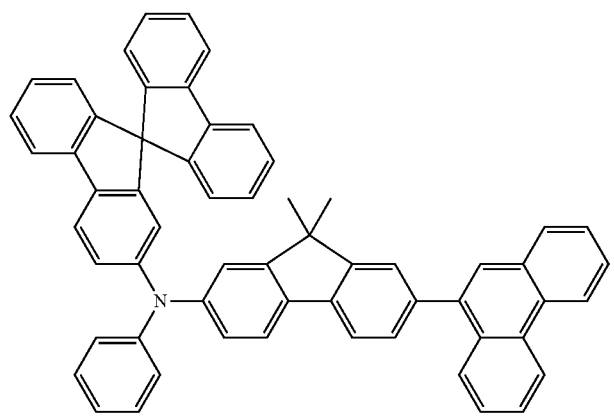
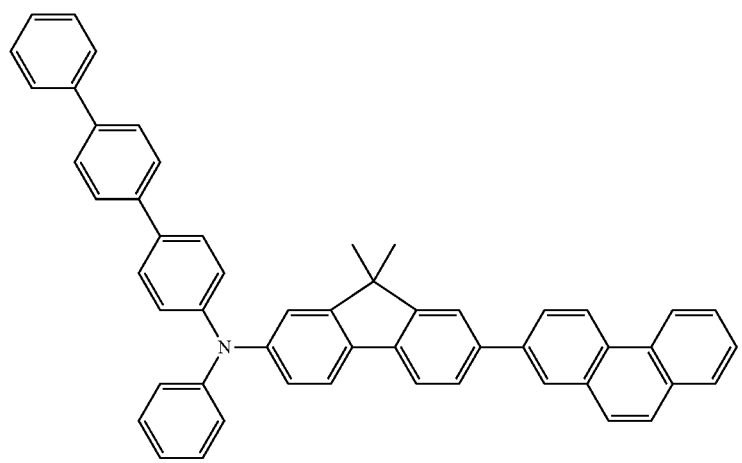
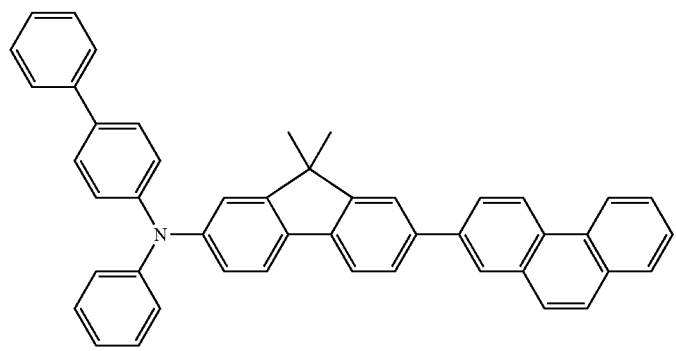

-continued
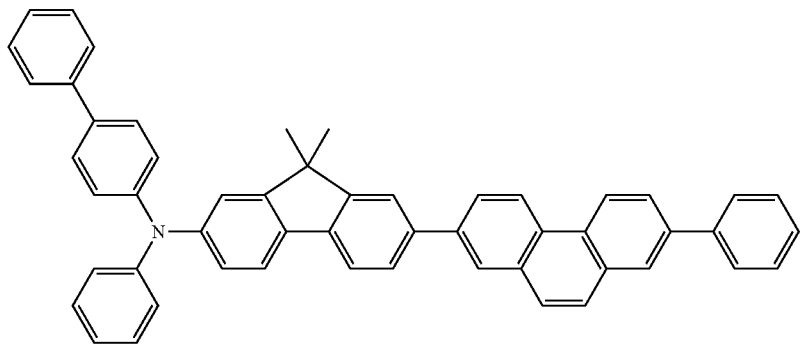
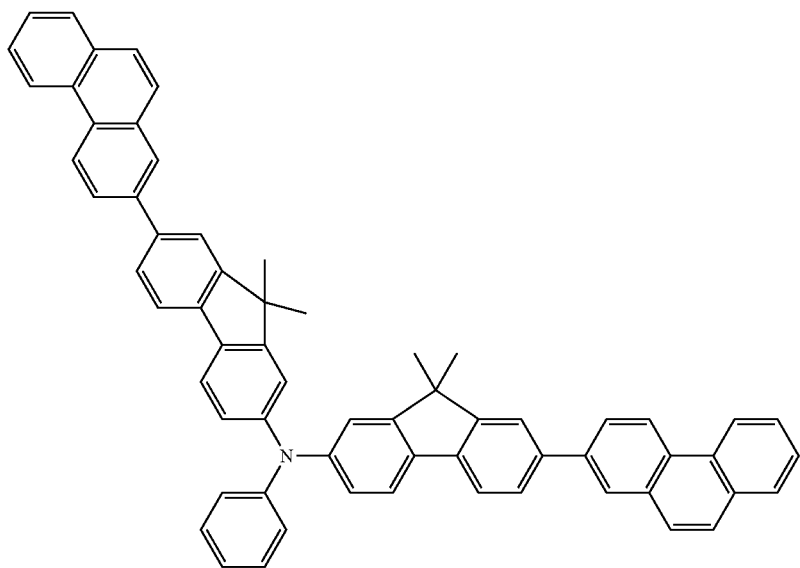
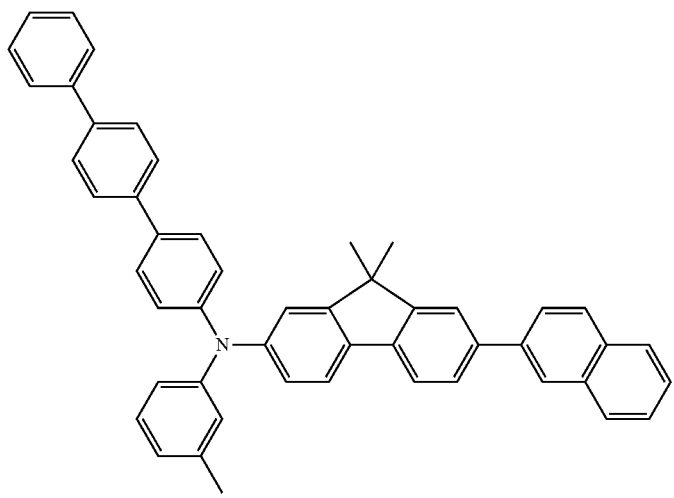

-continued
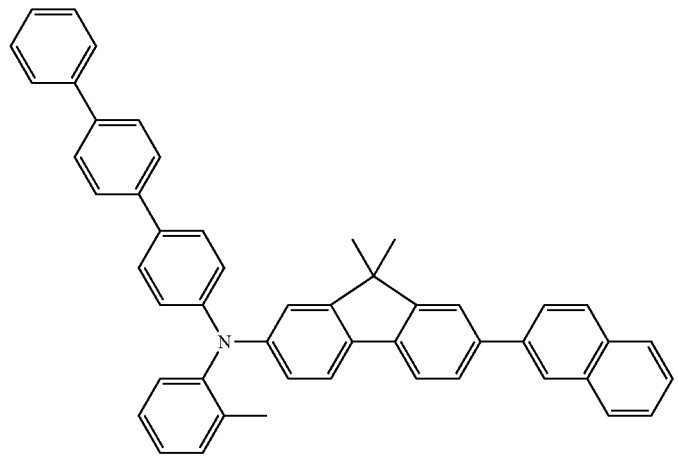
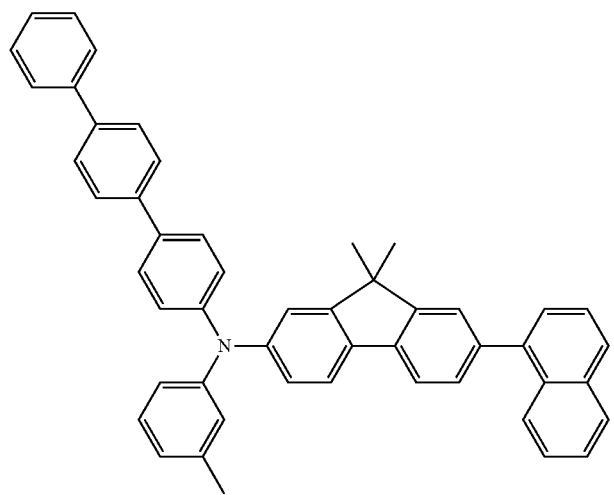
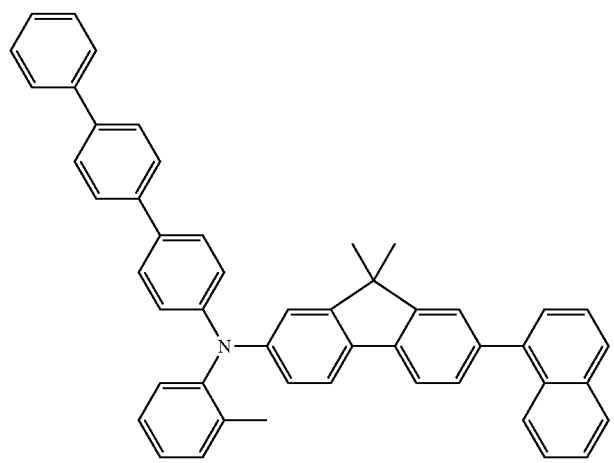

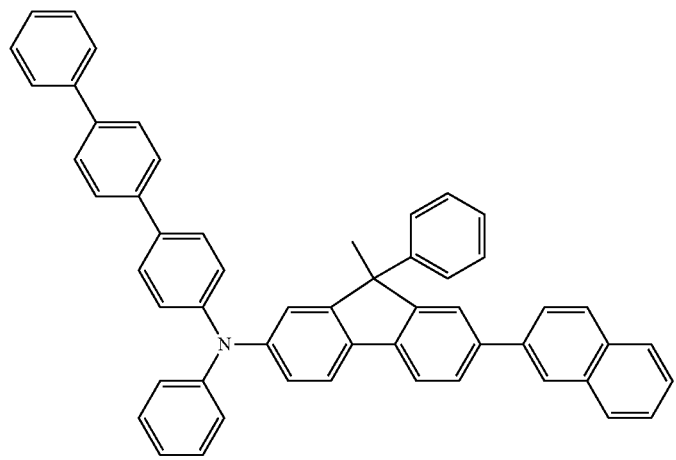
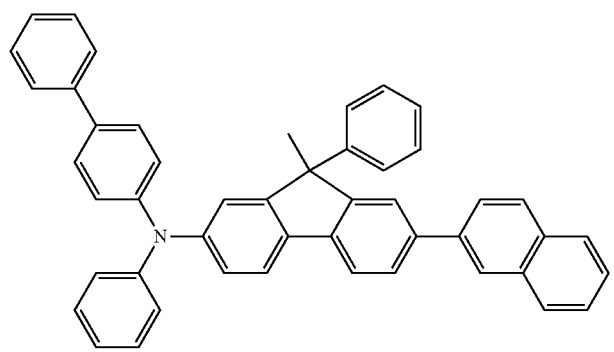
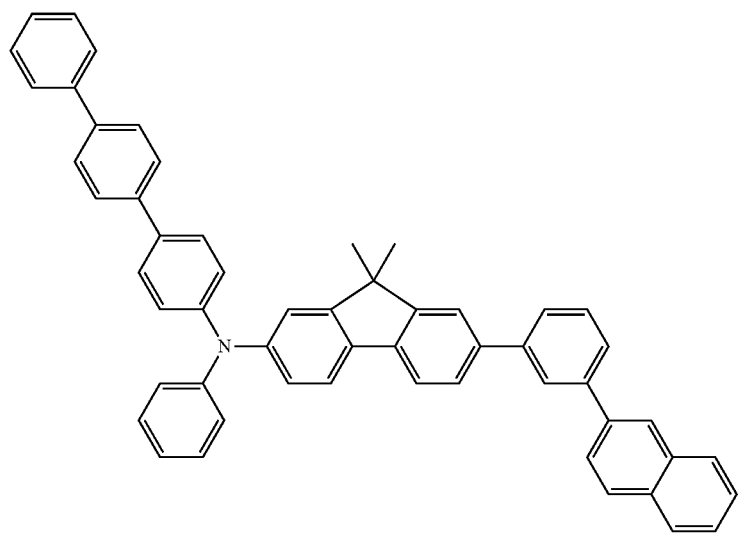

-continued
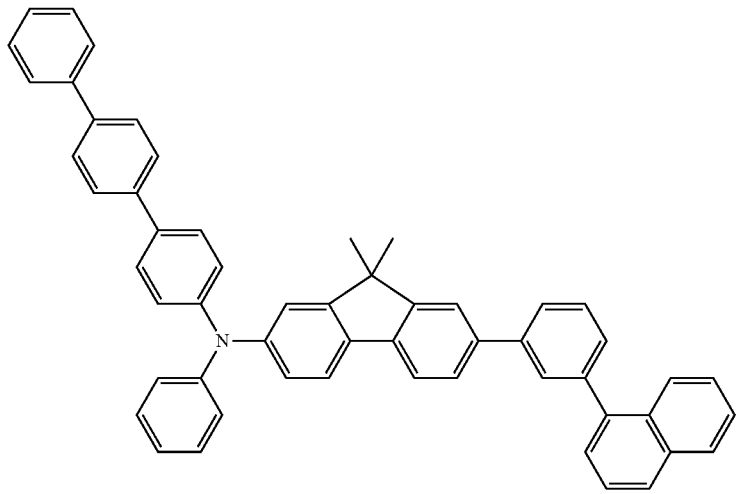
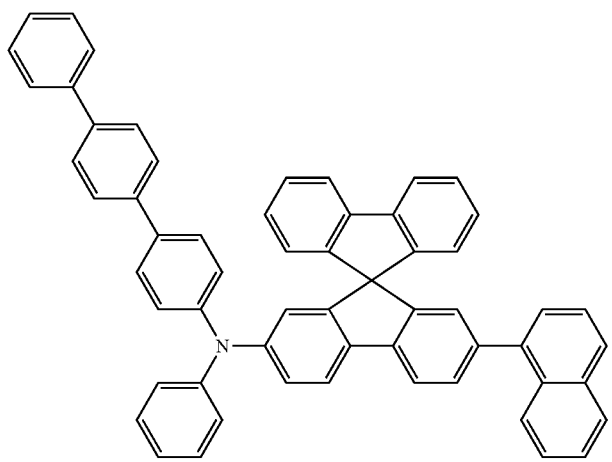
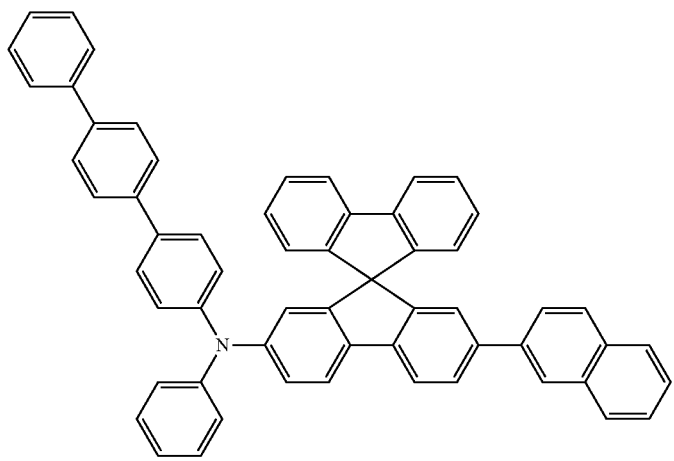

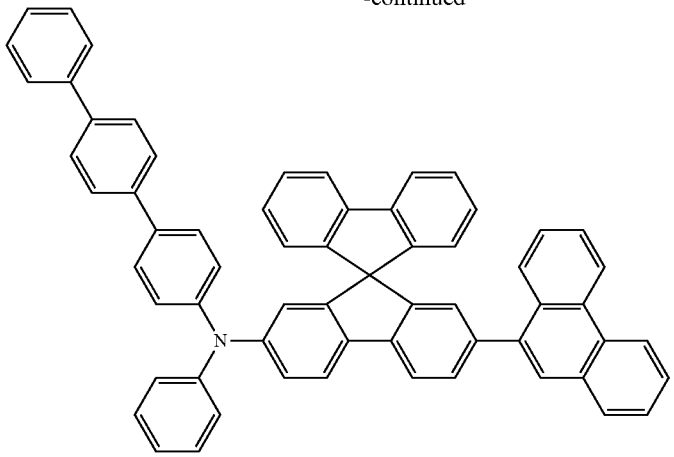

The aromatic amine derivative represented by the general formula (1) of the present invention has a substituted or unsubstituted phenyl group as $Ar^3$, whereby the electron density in the molecule is decreased, and the ionization potential is increased to be close to the ionization potential of the host material used in the light emitting layer of the organic EL element. Accordingly, the use of the aromatic amine derivative as the hole transporting material of the organic EL element reduces the energy barrier between the hole transporting layer and the light emitting layer, and thereby holes are suppressed from being accumulated at the interface between the hole transporting layer and the light emitting layer, thereby accelerating the injection of holes to the light emitting layer. As a result, the recombination probability of electrons and holes in the light emitting layer is increased, whereby as compared to the case where the aromatic amine derivative disclosed in WO 10/106,806, the light emission efficiency of the organic EL element is enhanced, and the load on the hole transporting layer due to electrons is decreased to prolong the lifetime of the organic EL element.

Consequently, the aromatic amine derivative of the present invention is useful as a material for an organic electroluminescent element, and particularly useful as a hole transporting material for an organic electroluminescent element.

The aromatic amine derivative of the present invention is not particularly limited in the production method thereof, and may be produced by utilizing and applying known methods with reference to the examples shown in the present specification. Examples of the production method are shown below, but the production method is not particularly limited.

Production Method of Aromatic Amine Derivative

The following intermediate X, which is a halogen compound, is first synthesized.

For example, 1-naphthylboronic acid and 4-iodo-1-bromo (9,9-dimethyl)fluorene are reacted in the presence of a catalyst (for example, tetrakis(triphenylphosphine)palladium(0)) in an aqueous solution containing a solvent (for example, toluene) and a base (for example, sodium carbonate) at from room temperature (20° C.) to 150° C., and the product is appropriately separated and purified by an ordinary separation and purification method for an organic compound, thereby providing the intermediate X. The reaction is preferably performed in an inert gas atmosphere, such as argon.

Intermediate X $Ar^1$—X

Separately, an intermediate Y, which is an amine compound, is synthesized.

A halogenated compound (for example, 4-bromo-p-terphenyl) and a compound capable of forming an amino group (which may contain a compound capable of forming a substituted or unsubstituted aryl group having from 6 to 30 ring-forming carbon atoms) (for example, aniline) are reacted in the presence of a catalyst (for example, tris(dibenzylideneacetone) and tri-t-butylphosphine) in a solvent (for example, toluene) at from 50 to 150° C. Thereafter, the product is appropriately separated and purified by an ordinary separation and purification method for an organic compound, thereby providing the intermediate Y. The reaction is preferably performed in an inert gas atmosphere, such as argon.

Intermediate Y $Ar^2Ar^3N$—H

Subsequently, the intermediate X and the intermediate Y are reacted in the presence of a catalyst (for example, tetrakis(triphenylphosphine)palladium(0)) in a solvent (for example, dehydrated toluene) at from 0 to 150° C. to synthesize the aromatic amine derivative of the present invention. The reaction is preferably performed in an inert gas atmosphere, such as argon.

After completing the reaction, the reaction mixture is cooled to room temperature, water is added thereto, the reaction product is filtered, and the filtrate is extracted with a solvent, such as toluene, and then dried over a drying agent, such as anhydrous magnesium sulfate. The filtrate is concentrated by removing the solvent under reduced pressure. The crude product thus obtained is purified by column chromatography, recrystallized from a solvent, such as toluene, filtered and dried, thereby providing the purified aromatic amine derivative of the present invention.

Organic Electroluminescent Element

The organic EL element of the present invention will be described below.

Representative examples of the structure of the organic EL element of the present invention are shown below, but the structure is not limited thereto. The structure (4) is preferably used.

(1) anode/hole transporting layer/light emitting layer/cathode
(2) anode/hole injection layer/hole transporting layer/light emitting layer/cathode (3) anode/hole injection layer/hole transporting layer/light emitting layer/electron injection layer/cathode
(4) anode/hole injection layer/hole transporting layer/light emitting layer/electron transporting layer/electron injection layer/cathode An electron barrier layer may be appropriately provided between the hole transporting layer and the light emitting layer. A hole barrier layer may be appropriately provided between the light emitting layer and the electron injection layer and between the light emitting layer and the electron transporting layer. The use of the electron barrier layer and the hole barrier layer confines electrons or holes in the light emitting layer to enhance the recombination probability of charges in the light emitting layer, thereby enhancing the light emission efficiency.

In the plural organic thin film layers, a light emitting material, a doping material, a hole injection material, an electron injection material and the like, which have been known in the art, may be used in addition to the aromatic amine derivative of the present invention.

The hole injection layer, the light emitting layer and the electron injection layer may each be formed to have a layer structure containing two or more layers. In this case, for the hole injection layer, the layer that injects holes from the electrode is referred to as a hole injection layer, and the layer that receives holes from the hole injection layer and transports the holes to the light emitting layer is referred to as a hole transporting layer. Similarly, for the electron injection layer, the layer that injects electrons from the electrode is referred to as an electron injection layer, and the layer that receives electrons from the electron injection layer and transports the electrons to the light emitting layer is referred to as an electron transporting layer.

The layers may be selected and used depending on such factors as the energy level, the heat resistance and the adhesiveness to the organic layer or the metal electrode of the materials.

In the organic EL element of the present invention, the aromatic amine derivative of the present invention may be used in any of the organic thin film layers, and is preferably contained in the hole injection layer or the hole transporting layer, and more preferably contained in the hole transporting layer, from the standpoint of the light emission efficiency and the lifetime of the organic EL element.

The amount of the aromatic amine derivative of the present invention contained in one of the organic thin film layers, preferably in the hole injection layer or the hole transporting layer, is preferably from 30 to 100% by mass, more preferably from 50 to 100% by mass, further preferably from 80 to 100% by mass, and particularly preferably substantially 100% by mass, based on the total components of the organic thin film layer, from the standpoint of the light emission efficiency and the lifetime of the organic EL element.

As a preferred embodiment, the layers of the organic EL element having a structure where the aromatic amine derivative of the present invention is contained in the hole transporting layer are described below.

Substrate

The organic EL element is generally formed on a light transmissive substrate. The light transmissive substrate is a substrate that supports the organic EL element and preferably has a transmittance to light in the visible range of from 400 to 700 nm of 50% or more, and a flat substrate is preferably used.

Examples of the light transmissive substrate include a glass plate and a synthetic resin plate. Examples of the glass plate include particularly plates formed of soda-lime glass, barium-strontium-containing glass, lead glass, aluminosilicate glass, borosilicate glass, barium-borosilicate glass and quartz. Examples of the synthetic resin plate include plates of a polycarbonate resin, an acrylic resin, a polyethylene terephthalate resin, a polyether sulfide resin and a polysulfone resin.

Anode

The anode has a function of injecting holes to the hole transporting layer or the light emitting layer, and may effectively has a work function of 4 eV or more (and preferably 4.5 eV or more). Specific examples of the material of the anode used in the present invention include carbon, aluminum, vanadium, iron, cobalt, nickel, tungsten, silver, gold, platinum, palladium, alloys of these metals, an ITO substrate, a metal oxide used in a NESA substrate, such as tin oxide and indium oxide, and an organic electroconductive resin, such as polythiophene and polypyrrole.

The anode may be produced by forming a thin film of these electrode materials by such a method as a vapor deposition method and a sputtering method.

In the case where light emitted from the light emitting layer is taken out from the anode, the transmittance of the anode to the emitted light is preferably 10% or more. The sheet resistance of the anode is preferably several hundred $\Omega$ per square or less. The thickness of the anode is generally from 10 nm to 1 µm, and preferably from 10 to 200 nm, while depending on the material thereof.

Cathode

The cathode may contain, as an electrode substance, such as a metal, an alloy, an electroconductive compound, and a mixture thereof, which have a small work function (less than 4 eV). Specific examples of the electrode substance include magnesium, calcium, tin, lead, titanium, yttrium, lithium, ruthenium, manganese, aluminum, lithium fluoride, and an alloy thereof, but the electrode substance is not limited thereto. Representative examples of the alloy include magnesium-silver, magnesium-indium and lithium-aluminum, but the alloy is not limited thereto. The ratio of the alloy may be controlled by the temperature of the vapor deposition source, the atmosphere, the vacuum degree and the like, and may be selected to be a suitable ratio. The anode and the cathode each may be formed to have a layer structure containing two or more layers depending on necessity.

The cathode may be produced by forming the electrode substance into a thin film by such a method as vapor deposition or sputtering.

In the case where light emitted from the light emitting layer is taken out, the cathode preferably has a transmittance to the emitted light of 10% or more. The cathode preferably has a sheet resistance of several hundred $\Omega$ per square or less, and generally has a thickness of from 10 nm to 1 µm, and preferably from 50 to 200 nm.

Dielectric Layer

In general, the organic EL element may suffer image defects due to leakage or short circuit since an electric field is applied to the ultrathin film. For preventing the defects, a dielectric layer formed of a dielectric thin film layer may be inserted between the pair of electrodes.

Examples of the material used in the dielectric layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide, and mixtures and laminated products thereof may also be used.

Light Emitting Layer

The light emitting layer of the organic EL element provides a field for recombination of electrons and holes and has a function of leading the recombination to light emission.

The host material and the doping material that can be used in the light emitting layer are not particularly limited, and examples thereof include a polycondensed aromatic compound and a derivative thereof, such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, fluorantene, 9,10-diphenylanthracene, 9,10-bis(phenylethynyl)anthracene and 1,4-bis(9'-ethynylanthracenyl)benzene; an organic metal complex, such as tris(8-quinolinolato)aluminum, bis(2-methyl-8-quinolinolato)-4-(phenylphenolinato)aluminum; an arylamine derivative, a styrylamine derivative, a stilbene derivative, a coumarin derivative, a pyran derivative, an oxazone derivative, a benzothiazole derivative, a benzoxazole derivative, a benzoimidazole derivative, a pyrazine derivative, a cinnamate ester derivative, a diketopyrrolopyrrole derivative, an acridone derivative, and a quinacridone derivative. Among these, an anthracene derivative, a fluorantene derivative, a styrylamine derivative and an arylamine derivative are preferred, and an anthracene derivative and a fluorantene derivative are more preferred, from the standpoint of the driving voltage, the light emission efficiency and the lifetime of the organic EL element. The anthracene derivative preferably has from 30 to 100 ring-forming carbon atoms, more preferably from 35 to 80 ring-forming carbon atoms, and further preferably from 35 to 60 ring-forming carbon atoms. The fluorantene derivative preferably has from 30 to 100 ring-forming carbon atoms, more preferably from 35 to 80 ring-forming carbon atoms, and further preferably from 35 to 60 ring-forming carbon atoms.

Hole Injection Layer and Hole Transporting Layer

The hole injection layer and the hole transporting layer assist injection of holes to the light emitting layer to transport holes to the light emitting region, and has a large hole mobility and small ionization energy, which is generally 5.7 eV or less. The hole injection layer and the hole transporting layer are preferably formed of a material that transports holes to the light emitting layer under a lower electric field intensity, and the material further preferably has a hole mobility, for example, of $10^{-4}$ cm$^2$/V or more on application of an electric field of from $10^4$ to $10^6$ V/cm.

The aromatic amine derivative of the present invention is preferably used in the hole injection layer or the hole transporting layer, and particularly preferably used in the hole transporting layer, as described above. In the case where the aromatic amine derivative of the present invention is used in both the hole injection layer and the hole transporting layer, the aromatic amine derivatives used in these layers may be the same as or different from each other.

On using the aromatic amine derivative of the present invention in the hole injection layer or the hole transporting layer, the hole injection layer or the hole transporting layer may be formed solely with the aromatic amine derivative of the present invention, or may be formed with a mixture with an additional material.

The additional material for forming the hole injection layer or the hole transporting layer after mixing with the aromatic amine derivative of the present invention is not particularly limited, as far as the material has the aforementioned preferred properties, and materials that have been ordinarily used as a hole injection material or a hole transporting material in a photoconductive material and known materials that have been used in a hole injection layer or a hole transporting layer in an organic EL element may be used after appropriate selection. In the present specification, a material that has a hole transporting capability and can be used in the hole transporting region is referred to as a hole transporting material, and a material that has a hole injection capability and can be used in the hole injection region is referred to as a hole injection material.

Specific examples of the additional material other than the aromatic amine derivative of the present invention for the hole injection layer or transporting layer include a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, a polyarylalkane, stilbene, butadiene, a benzidine type triphenylamine, a styrylamine type triphenylamine and a diamine type triphenylamine, derivatives of these compounds, and a polymer material, such as polyvinylcarbazole, polysilane and an electroconductive polymer, but the material is not limited thereto.

Examples of the effective material among the hole injection materials and the hole transporting materials capable of being used in the organic EL element of the present invention include an aromatic tertiary amine derivative and phthalocyanine derivative, preferred examples thereof include an aromatic tertiary amine derivative, and more preferred examples thereof include an aromatic tertiary diamine derivative, while not limited. The material is particularly preferably used as the hole injection material.

Examples of the aromatic tertiary amine derivative include an aromatic tertiary monoamine derivative, such as triphenylamine, tritolylamine and tolyldiphenylamine; an aromatic tertiary diamine derivative, such as N,N'-diphenyl-N,N'-(3-methylphenyl)-1,1'-biphenylyl-4,4'-diamine, N,N,N',N'-(4-methylphenyl)-1,1'-phenyl-4,4'-diamine, N,N,N',N'-(4-methylphenyl)-1,1'-biphenylyl-4,4'-diamine, N,N'-diphenyl-N,N'-dinaphthyl-1,1'-biphenylyl-4,4'-diamine, N,N'-(methylphenyl)-N,N'-(4-n-butylphenyl)-phenanthrene-9,10-diamine and diamine represented by the following formula:

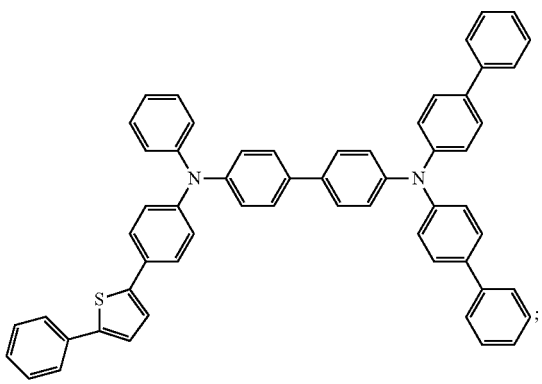 [SMILES: c1ccc(-c2ccc(N(c3ccc(-c4ccccc4)cc3)c3ccc(-c4ccc(N(c5ccccc5)c5ccc(-c6ccc(-c7ccccc7)s6)cc5)cc4)cc3)cc2)cc1]

an aromatic tertiary triamine derivative, such as N,N-bis(4-di-4-tolylaminophenyl)-4-phenylcyclohexane; an aromatic tertiary tetramine derivative, such as N,N'-diphenyl-N,N'-bis(4-diphenylamino)phenyl-1,1'-biphenylyl-4,4'-diamine; and an oligomer and a polymer having the aromatic tertiary amine skeleton, but the aromatic tertiary amine derivative is not limited thereto. Among these, an aromatic tertiary tetramine derivative is preferred from the standpoint of the driving voltage, the light emission efficiency and the lifetime of the organic EL element.

Examples of the phthalocyanine (Pc) derivative as the hole injection material or the hole transporting material include phthalocyanine derivatives and naphthalocyanine derivatives, such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc and GaPc-O—GaPc, but the phthalocyanine derivative is not limited thereto.

The hole injection material and the hole transporting material other than the aromatic tertiary amine derivative and the phthalocyanine derivative are not particularly limited, as far as the material has the aforementioned preferred properties, and materials that have been ordinarily used as a hole injection material or a hole transporting material in a photoconductive material and known materials that have been used in a hole injection layer or a hole transporting layer in an organic EL element may be used after appropriate selection.

In addition, a material that accepts electrons emitted and transports the electrons to the electrode (cathode), i.e., a so-called acceptor material, is preferably used as the hole injection material or the hole transporting material.

Examples of the acceptor material include a compound having two condensed aromatic ring in the molecule thereof, such as 4,4'-bis(N-(1-naphthyl)-N-phenylamino)biphenyl and 4,4',4''-tris(N-(3-methyphenyl)-N-phenylamino)triphenylamine having three triphenylamine units connected in a star burst form.

The acceptor material may be a nitrogen-containing heterocyclic derivative represented by the following formula:

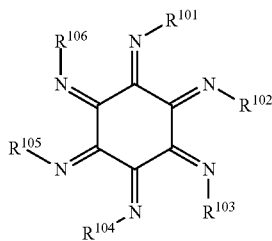

wherein to $R^{101}$ to $R^{106}$ each independently represent a substituted or unsubstituted alkyl group having from 1 to 20 carbon atoms, a substituted or unsubstituted aryl group having from 6 to 20 carbon atoms, a substituted or unsubstituted aralkyl group having from 7 to 20 carbon atoms or a substituted or unsubstituted heterocyclic group having from 5 to 20 ring-forming atoms, provided that $R^{101}$ and $R^{102}$, $R^{103}$ and $R^{104}$, and $R^{105}$ and $R^{106}$ each may be bonded to each other to form a condensed ring.

The acceptor material may be a hexaazatriphenylene compound represented by the following general formula:

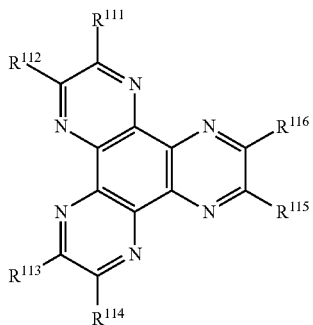

wherein $R^{111}$ to $R^{116}$ each independently represent a cyano group, —CONH$_2$, a carboxyl group or —COOR$^{117}$ (wherein $R^{117}$ represents an alkyl group having from 1 to 20 carbon atoms), or $R^{111}$ and $R^{112}$ and $R^{114}$, or $R^{115}$ and $R^{116}$ each together represent a group represented by —CO—O—CO—.

In the case where $R^{111}$ to $R^{116}$ represent a cyano group, —CONH$_2$, a carboxyl group or —COOR$^{117}$, the groups are preferably the same as each other. In the case where $R^{111}$ and $R^{112}$, $R^{113}$ and $R^{114}$, or $R^{115}$ and $R^{116}$ each together represent a group represented by —CO—O—CO—, all the groups are preferably a group represented by —CO—O—CO—.

Electron Injection Layer and Electron Transporting Layer

The electron injection layer and the electron transporting layer each is a layer that assists injection of electrons to the light emitting layer and transports electrons to the light emitting region, and the layers have a large electron mobility. In the electron injection layer, a layer that is formed of a material having particularly good adhesion to the cathode (i.e., an adhesion improving layer) may be provided.

It is known in the organic EL element that emitted light is reflected by the electrode (i.e., the cathode in this case), and thus light that is taken out directly from the anode and light that is taken out after reflecting by the electrode interfere with each other. For utilizing the interference effectively, the thickness of the electron transporting layer is appropriately selected from a range of from several nm to several μm, and in the case of the layer having a large thickness in particular, the electron mobility is preferably at least $10^{-5}$ cm$^2$/Vs or more on application of an electric field of from 10' to $10^6$ V/cm.

Specific examples of the material used in the electron injection layer include fluorenone, anthraquinodimethane, diphenoquinone, thiopyran dioxide, oxazole, oxadiazole, triazole, imidazole, perylenetetracarboxylic acid, fluorenylidenemethane, anthraquinodimethane and anthrone, and derivatives of these compounds, but the material is not limited thereto. The hole injection material and the electron injection material may be sensitized by adding an electron accepting substance and an electron donating substance, respectively, thereto.

A further effective electron injection material in the organic EL element of the present invention is a metal complex compound and a nitrogen-containing five-membered ring derivative.

Preferred examples of the metal complex compound include 8-hydroxyquinolinatolithium, tris(8-hydroxyquinolinato)aluminum and bis(2-methyl-8-quinolinato) (1-naphtholato)aluminum, but the compound is not limited thereto.

Preferred examples of the nitrogen-containing five-membered ring derivative include derivatives of oxazole, thiazole, oxadiazole, thiadiazole and triazole.

In the organic EL element of the present invention, in particular, the nitrogen-containing five-membered ring derivative is preferably a benzoimidazole derivative represented by one of the following formulae (1) to (3).

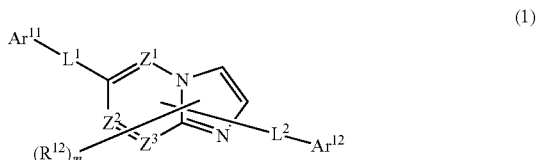

(1)

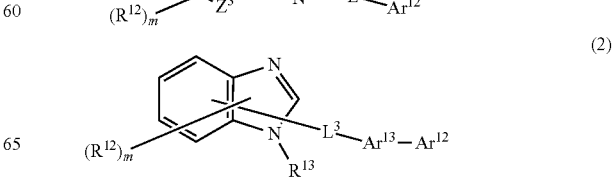

(2)

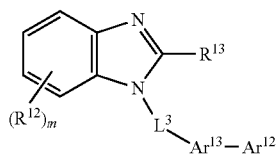
(3)

In the formulae (1) to (3), $Z^1$, $Z^2$ and $Z^3$ each independently represent a nitrogen atom or a carbon atom.

$R^{12}$ represents a substituted or unsubstituted aryl group having from 6 to 60 (preferably from 6 to 40, and more preferably from 6 to 20) ring-forming carbon atoms, a substituted or unsubstituted heteroaryl group having from 5 to 60 (preferably from 5 to 40, and more preferably from 5 to 20) ring-forming atoms, an alkyl group having from 1 to 20 (preferably from 1 to 10, and more preferably from 1 to 5) carbon atoms, an alkyl group having from 1 to 20 (preferably from 1 to 10, and more preferably from 1 to 5) carbon atoms having a halogen atom substituted thereon, or an alkoxy group having from 1 to 20 (preferably from 1 to 10, and more preferably from 1 to 5) carbon atoms.

$R^{13}$ represents a hydrogen atom, a substituted or unsubstituted aryl group having from 6 to 60 (preferably from 6 to 40, and more preferably from 6 to 20) ring-forming carbon atoms, a substituted or unsubstituted heteroaryl group having from 5 to 60 (preferably from 5 to 40, and more preferably from 5 to 20) ring-forming atoms, an alkyl group having from 1 to 20 (preferably from 1 to 10, and more preferably from 1 to 5) carbon atoms, an alkyl group having from 1 to 20 (preferably from 1 to 10, and more preferably from 1 to 5) carbon atoms having a halogen atom substituted thereon, or an alkoxy group having from 1 to 20 (preferably from 1 to 10, and more preferably from 1 to 5) carbon atoms.

m represents an integer of from 0 to 5, and when m is an integer of 2 or more, plural groups of $R^{12}$ may be the same as or different from each other. The plural adjacent groups represented by $R^{12}$ may be bonded to each other to form a substituted or unsubstituted aromatic hydrocarbon ring. Examples of the substituted or unsubstituted aromatic hydrocarbon ring, which is formed by bonding the plural adjacent groups represented by $R^{12}$ when m is an integer of 2 or more, include a benzene ring, a naphthalene ring and an anthracene ring.

$Ar^{11}$ represents a substituted or unsubstituted aryl group having from 6 to 60 (preferably from 6 to 40, and more preferably from 6 to 20) ring-forming carbon atoms or a substituted or unsubstituted heteroaryl group having from 5 to 60 (preferably from 5 to 40, and more preferably from 5 to 20) ring-forming atoms.

$Ar^{12}$ represents a hydrogen atom, an alkyl group having from 1 to 20 (preferably from 1 to 10, and more preferably from 1 to 5) carbon atoms, an alkyl group having from 1 to 20 (preferably from 1 to 10, and more preferably from 1 to 5) carbon atoms having a halogen atom substituted thereon, an alkoxy group having from 1 to 20 (preferably from 1 to 10, and more preferably from 1 to 5) carbon atoms, a substituted or unsubstituted aryl group having from 6 to 60 (preferably from 6 to 40, and more preferably from 6 to 20) ring-forming carbon atoms or a substituted or unsubstituted heteroaryl group having from 5 to 60 (preferably from 5 to 40, and more preferably from 5 to 20) ring-forming atoms.

$Ar^{13}$ represents a substituted or unsubstituted arylene group having from 6 to 60 (preferably from 6 to 40, and more preferably from 6 to 20) ring-forming carbon atoms or a substituted or unsubstituted heteroarylene group having from 5 to 60 (preferably from 5 to 40, and more preferably from 5 to 20) ring-forming atoms.

$L^1$, $L^2$ and $L^3$ each independently represent a single bond, a substituted or unsubstituted arylene group having from 6 to 60 ring-forming carbon atoms, a substituted or unsubstituted hetero condensed ring group having from 9 to ring-forming atoms or a substituted or unsubstituted fluorenylene group.

In the organic EL element of the present invention, a light emitting material, a doping material, a hole injection material or an electron injection material may be contained in the layer that contains the aromatic amine derivative of the present invention.

The organic EL element obtained by the present invention may be provided with a protective layer on the surface of the element, or may be entirely protected with a silicon oil, a resin or the like, from the standpoint of the enhancement of the stability of the element to temperature, humidity, atmosphere and the like.

The layers of the organic EL element of the present invention may be formed by any of a dry film forming method, such as vacuum vapor deposition, sputtering, plasma and ion plating, and a wet film forming method, such as spin coating, dipping and flow coating.

The layers are not particularly limited in thickness, the thickness may be determined to be a suitable thickness as the organic EL element. When the thickness is too large, a large application voltage may be required for providing certain optical output, thereby deteriorating the efficiency. When the thickness is too small, pinholes and the like may occur, thereby failing to provide a sufficient light emission luminance even on application of an electric field. The thickness is generally suitably in a range of from 5 nm to 10 μm and more preferably in a range of from 10 nm to 0.2 μm.

In the wet film forming method, the materials for forming the layers are dissolved or dispersed in a suitable solvent, such as ethanol, chloroform, tetrahydrofuran and dioxane, with which a thin film is formed, and any of the solvents may be used.

As a solution suitable for the wet film forming method, an organic EL material-containing solution containing the aromatic amine derivative of the present invention as an organic EL material and a solvent may be used. In all the organic thin film layers, a resin and an additive may be suitably used for enhancing the film forming property and preventing pinholes from being formed in the film. Examples of the resin include a dielectric resin and a copolymer thereof, such as polystyrene, polycarbonate, polyarylate, polyester, polyamide, polyurethane, polysulfone, polymethyl methacrylate, polymethyl acrylate and cellulose, a photoconductive resin, such as poly-N-vinylcarbazole and polysilane, and an electroconductive resin, such as polythiophene and polypyrrole. Examples of the additive include an antioxidant, an ultraviolet ray absorbent and a plasticizer.

Production Method of Organic Electroluminescent Element

The organic electroluminescent element may be produced by forming the anode, the light emitting layer, the hole injection-transporting layer depending on necessity, and the electron injecting-transporting layer depending on necessity, and then forming the cathode, according to the materials and the formation methods exemplified above. In alternative, the organic electroluminescent element may be produced from the cathode to the anode, i.e., in the reverse order to the above.

An example of production of the organic electroluminescent element having a structure containing a light transmissive substrate having formed thereon an anode, a hole injection layer, a light emitting layer, an electron injection layer and a cathode in this order is shown below. On a suitable light transmissive substrate, a thin film formed of an anode material is formed to have a thickness of 1 μm or less (preferably from 10 to 200 nm) by such a method as vapor deposition or sputtering, thereby producing an anode. On the anode, a hole injection layer is then provided. The hole injection layer may be formed by such a method as a vacuum vapor deposition method, a spin coating method, a casting method and an LB method as described above, and is preferably formed by a vacuum vapor deposition method since a uniform film may be obtained, and pinholes may be prevented from being formed. In the case where the hole injection layer is formed by a vacuum vapor deposition method, the vapor deposition conditions may be preferably selected appropriately from a vapor deposition source temperature of from 50 to 450° C., a vacuum degree of from $10^{-7}$ to $10^{-3}$ Torr, a vapor deposition rate of from 0.01 to 50 nm/sec, a substrate temperature of from −50 to 300° C. and a film thickness of from 5 nm to 5 μm, while the conditions may vary depending on the compounds used (i.e., the material for the hole transporting layer), and the crystal structure, the recombination structure and the like of the target hole injection layer.

The light emitting layer, the electron injection layer and the cathode may be formed by arbitrary methods, which are not particularly limited. Examples of the formation methods include a vacuum vapor deposition method, an ionization vapor deposition method and a solution coating method (such as a spin coating method, a casting method, a dip coating method, a bar coating method, a roll coating method, a Langmuir-Blodgett method and an ink-jet method).

EXAMPLE

The present invention will be described more specifically with reference to examples below, but the present invention is not limited thereto.

The structures of the intermediates synthesized in Synthesis 1 to 6 blow are as follows.

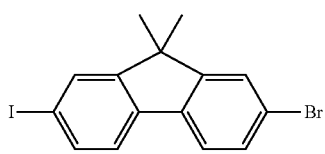

Intermediate 1

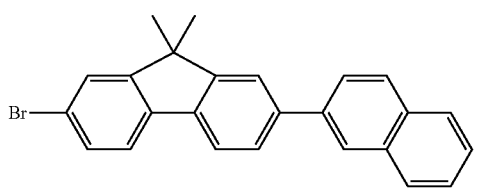

Intermediate 2

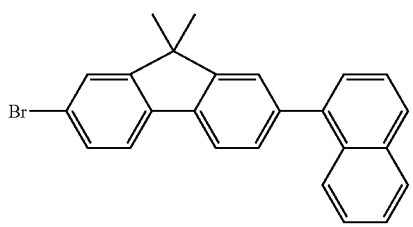

Intermediate 3

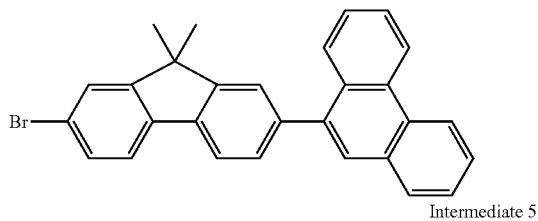

Intermediate 4

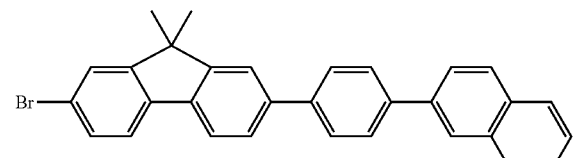

Intermediate 5

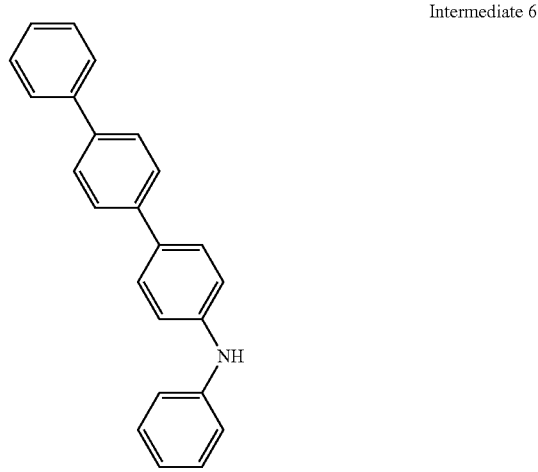

Intermediate 6

Synthesis 1

Synthesis of Intermediate 1

Under an argon atmosphere, 55 g of 2-bromo-9,9-dimethylfluorene, 23 g of iodine, 9.4 g of periodic acid dihydrate, 42 mL of water, 360 mL of acetic acid and 11 mL of sulfuric acid were placed in a 1,000 mL three-neck flask, stirred at 65° C. for 30 minutes, and then reacted at 90° C. for 6 hours.

The reaction product was placed in iced water and filtered. The product was rinsed with water and the rinsed with methanol, thereby providing 67 g of white powder. It was identified as Intermediate 1 by FD-MS (field desorption mass spectroscopy) analysis.

Synthesis 2

Synthesis of Intermediate 2

Under an argon atmosphere, 300 mL of toluene and 150 mL of a 2 M sodium carbonate aqueous solution were added to 39.9 g of Intermediate 1, 18.1 g of 2-naphthylboronic acid and 2.31 g of tetrakis(triphenylphosphine)palladium(0), and the mixture was heated under refluxing for 10 hours.

After completing the reaction, the mixture was immediately filtered, and the aqueous layer was removed. The organic layer was dried over sodium sulfate and then concentrated. The residue was purified by silica gel column chromatography, thereby providing 32.3 g of white powder. It was identified as Intermediate 2 by FD-MS analysis.

Synthesis 3

Synthesis of Intermediate 3

The same reaction was performed as in Synthesis 2 except that 18.1 g of 1-naphthylboronic acid was used instead of 2-naphthylboronic acid, thereby providing 30.2 g of white powder. It was identified as Intermediate 3 by FD-MS analysis.

Synthesis 4

Synthesis of Intermediate 4

The same reaction was performed as in Synthesis 2 except that 23.3 g of 9-phenanthrenylboronic acid was used instead of 2-naphthylboronic acid, thereby providing 34.7 g of white powder. It was identified as Intermediate 4 by FD-MS analysis.

Synthesis 5

Synthesis of Intermediate 5

The same reaction was performed as in Synthesis 2 except that 26.0 g of 4-(2-naphthyl)phenylboronic acid was used instead of 2-naphthylboronic acid, thereby providing 35.2 g of white powder. It was identified as Intermediate 5 by FD-MS analysis.

Synthesis 6

Synthesis of Intermediate 6

Under an argon stream, 30.7 g of 4-bromo-p-terphenyl, 9.3 g of aniline, 13.0 g of t-butoxy sodium, 460 mg of tris(dibenzilideneacetone)dipalladium(0), 210 mg of tri-t-butylphosphine were placed in 500 mL of dehydrated toluene, and reacted at 80° C. for 8 hours. After cooling, 2.5 L of water was added thereto, the mixture was filtered with Celite, and the filtrate was extracted with toluene and dried over anhydrous magnesium sulfate. The solution was concentrated under reduced pressure, and the resulting coarse product was purified by column chromatography, recrystallized from toluene, collected and then dried, thereby providing 22.5 g of pale yellow powder. It was identified as Intermediate 6 by FD-MS analysis.

The structures of the compounds HT1 to HT6, which are the aromatic amine derivatives produced in Synthesis Examples 1 to 6, are as follows.

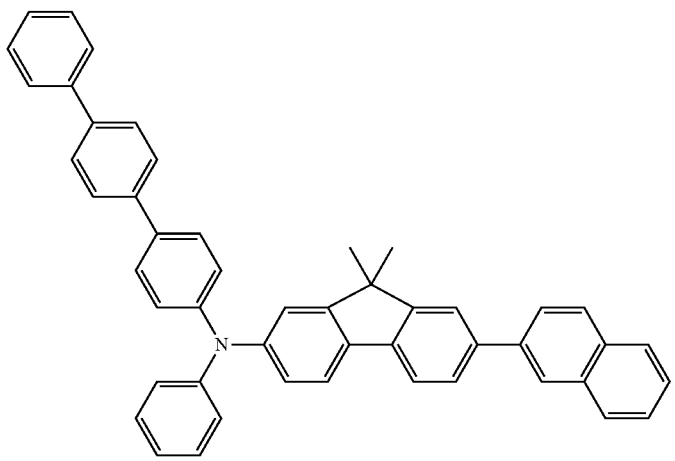

HT1

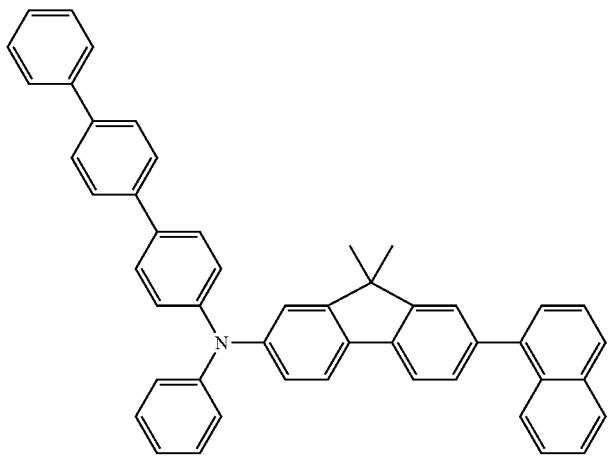

HT2

HT3
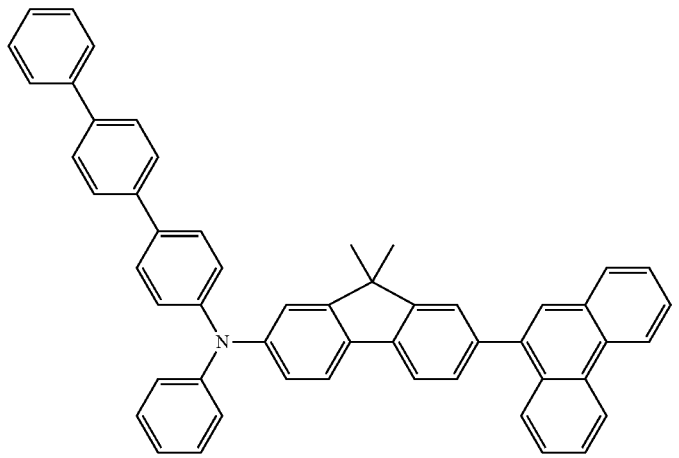
HT4
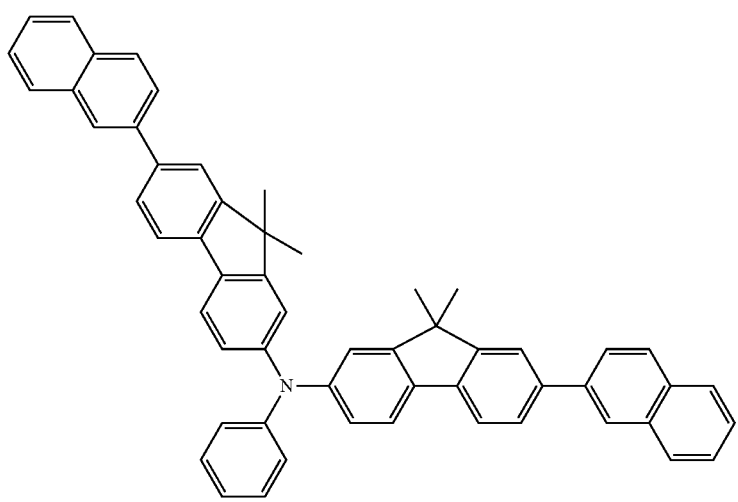
HT5
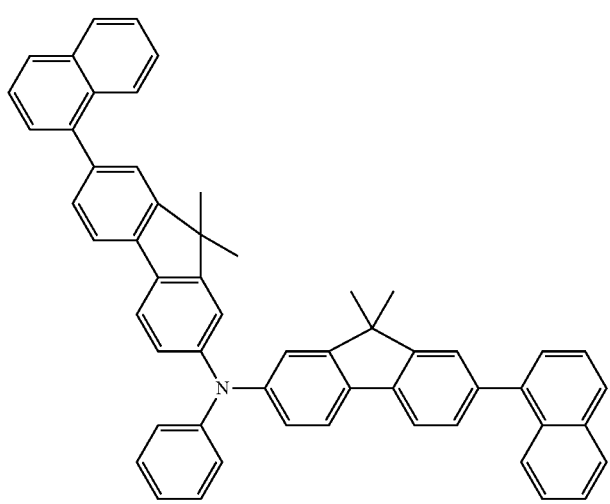

HT6

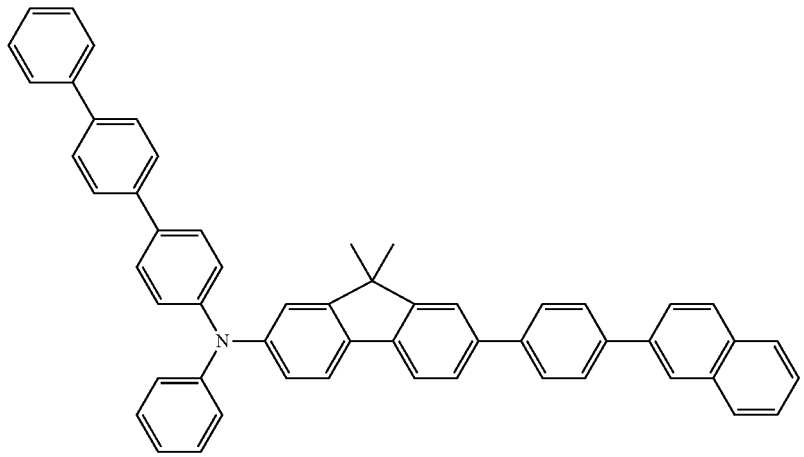

Synthesis Example 1

Synthesis of Aromatic Amine Derivative (HT1)

Under an argon stream, 8.0 g of Intermediate 2, 6.4 g of Intermediate 6, 2.6 g of t-butoxy sodium, 92 mg of tris(dibenzilideneacetone)dipalladium(0) and 42 mg of tri-t-butylphosphine were placed in 100 mL of dehydrated toluene, and reacted at 80° C. for 8 hours. After cooling, 500 mL of water was added thereto, the mixture was filtered with Celite, and the filtrate was extracted with toluene and dried over anhydrous magnesium sulfate. The solution was concentrated under reduced pressure, and the resulting coarse product was purified by column chromatography, recrystallized from toluene, collected and then dried, thereby providing 7.7 g of pale yellow powder. It was identified as the aromatic amine derivative (HT1) by FD-MS analysis.

Synthesis Example 2

Synthesis of Aromatic Amine Derivative (HT2)

The same reaction was performed as in Synthesis Example 1 except that 8.0 g of Intermediate 3 was used instead of Intermediate 2, thereby providing 7.5 g of pale yellow powder. It was identified as the aromatic amine derivative (HT2) by FD-MS analysis.

Synthesis Example 3

Synthesis of Aromatic Amine Derivative (HT3)

The same reaction was performed as in Synthesis Example 1 except that 9.0 g of Intermediate 4 was used instead of Intermediate 2, thereby providing 8.2 g of pale yellow powder. It was identified as the aromatic amine derivative (HT3) by FD-MS analysis.

Synthesis Example 4

Synthesis of Aromatic Amine Derivative (HT4)

The same reaction was performed as in Synthesis Example 1 except that 16.0 g of Intermediate 2 was used, and 1.9 g of aniline was used instead of Intermediate 6, thereby providing 6.5 g of pale yellow powder. It was identified as the aromatic amine derivative (HT4) by FD-MS analysis.

Synthesis Example 5

Synthesis of Aromatic Amine Derivative (HT5)

The same reaction was performed as in Synthesis Example 1 except that 16.0 g of Intermediate 3 was used instead of Intermediate 2, and 1.9 g of aniline was used instead of Intermediate 6, thereby providing 6.5 g of pale yellow powder. It was identified as the aromatic amine derivative (HT5) by FD-MS analysis.

Synthesis Example 6

Synthesis of Aromatic Amine Derivative (HT6)

The same reaction was performed as in Synthesis Example 1 except that 9.5 g of Intermediate 5 was used instead of Intermediate 2, thereby providing 8.3 g of pale yellow powder. It was identified as the aromatic amine derivative (HT6) by FD-MS analysis.

Example 1

Production and Evaluation of Organic EL Element

A glass substrate having a dimension of 25 mm×75 mm×1.1 mm in thickness equipped with an ITO transparent electrode (produced by Geomatec Co., Ltd.) was rinsed with isopropyl alcohol under application of ultrasonic wave for minutes, and then cleaned with UV and ozone for 30 minutes. The glass substrate having a transparent electrode having been rinsed and cleaned was mounted on a substrate holder of a vacuum vapor deposition equipment, and the following compound (HT1) as a hole injection material was vapor-deposited so as to cover the transparent electrode to form a hole injection layer having a thickness of 50 nm on a surface of a side in which the transparent electrode is formed. Subsequent to the formation of the hole injection layer, the aromatic amine derivative (HT1) obtained in Synthesis Example 1 as a hole transporting material was vapor-deposited to form a hole transporting layer having a thickness of 45 nm.

On the hole transporting layer, the following compound (BH1) was vapor-deposited to form a film having a thickness of 25 nm. Simultaneously, the following compound (BD1) as a light emitting molecule was vapor-deposited to provide a mass ratio of the compound (BH1) and the compound (BD1) of 40/2. The resulting film functions as a light emitting layer.

Subsequently, the following compound (ET1) and the following compound (ET2) were vapor-deposited to form films having thicknesses of 5 nm and 20 nm, respectively, to form an electron transporting layer and an electron injecting layer, and furthermore LiF and metallic AL were laminated sequentially to thicknesses of 1 nm and 80 nm, respectively, to form a cathode, thereby producing an organic electroluminescent element.

The resulting organic EL element was driven for light emission with a direct electric current, and the luminance (L) and the electric current density were measured, from which the light emission efficiency (cd/A) at an electric current density of 10 mA/cm² and the driving voltage (V) were obtained. The half decay lifetime of the element at an electric current density of 50 mA/cm² was obtained. The results are shown in Table 1.

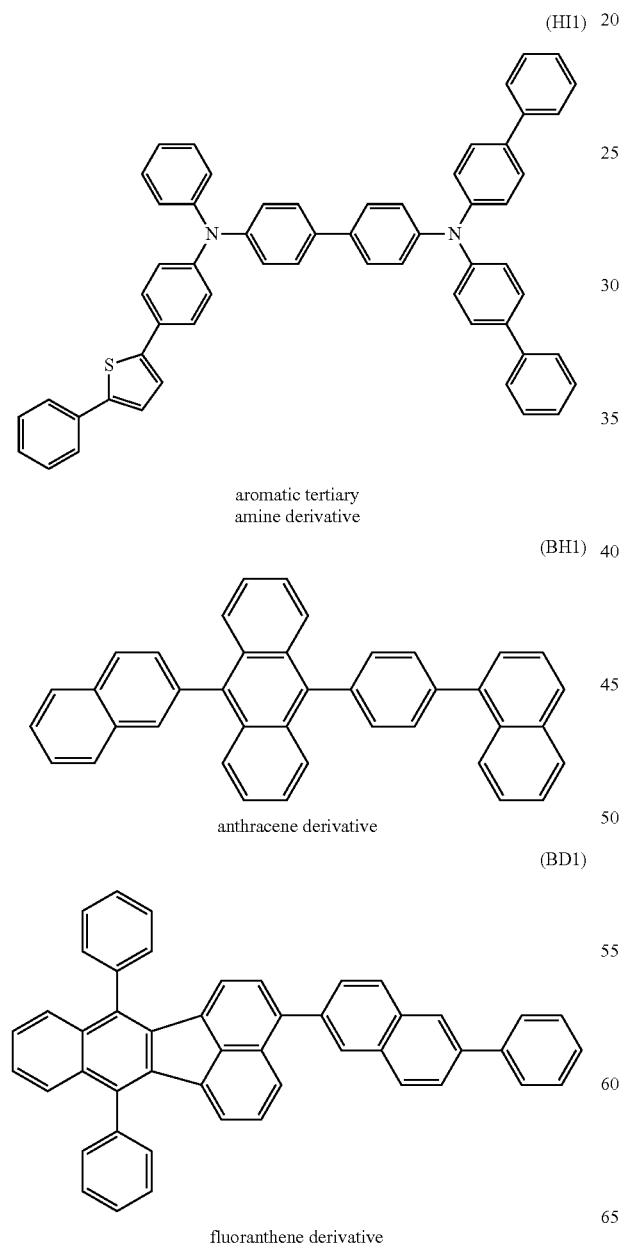

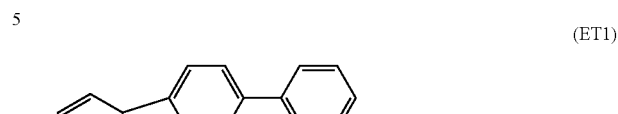

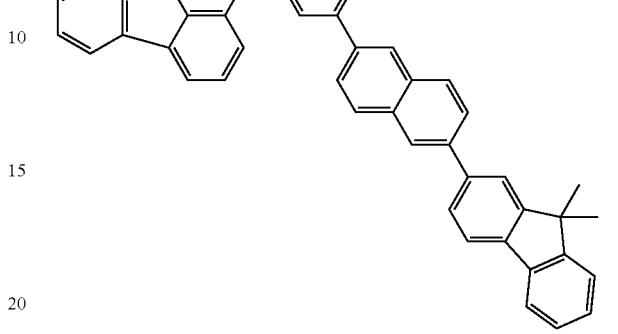

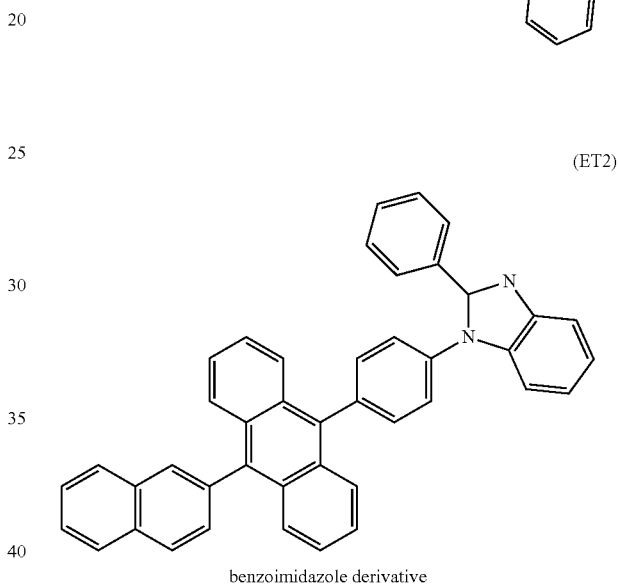

Examples 2 and 3

Production and Evaluation of Organic EL Elements

An organic EL element was produced in the same manner as in Example 1 except that the aromatic amine derivative (HT2) or the aromatic amine derivative (HT3) was used as the hole transporting material instead of the aromatic amine derivative (HT1), and evaluated. The results are shown in Table 1.

Comparative Examples 1 and 2

Production and Evaluation of Organic EL Elements

An organic EL element was produced in the same manner as in Example 1 except that the comparative compound 1 or the comparative compound 2 was used as the hole transporting material instead of the aromatic amine derivative (HT1), and evaluated. The results are shown in Table 1.

comparative compound 1

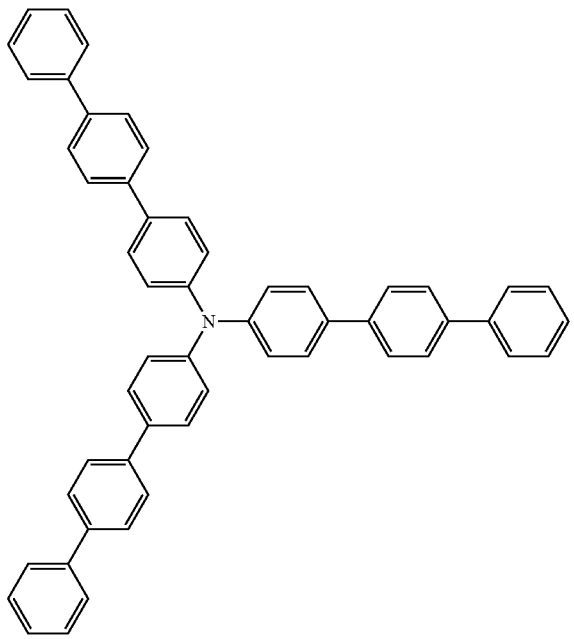

comparative compound 2

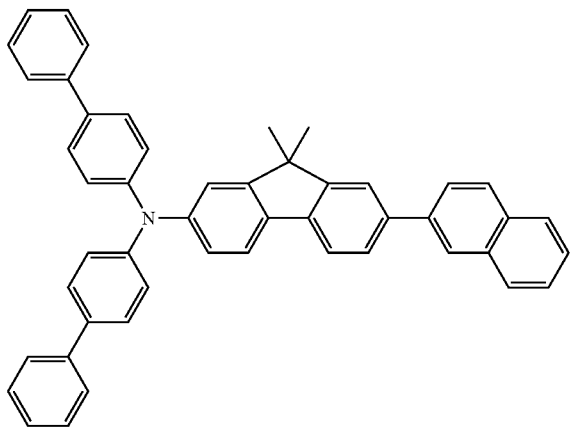

TABLE 1

|  |  | Hole transporting material | Measurement results | | |
|---|---|---|---|---|---|
|  |  |  | Light emission efficiency (cd/A) | Driving voltage (V) | half decay lifetime (hour) |
| Example | 1 | HT1 | 10.0 | 3.7 | 1,100 |
|  | 2 | HT2 | 10.6 | 3.8 | 1,300 |
|  | 3 | HT3 | 10.2 | 3.8 | 1,100 |
| Comparative Example | 1 | comparative compound 1 | 6.9 | 4.3 | 700 |
|  | 2 | comparative compound 2 | 7.4 | 3.8 | 1,300 |

It is understood from Table 1 that the organic EL elements using the aromatic amine derivative of the present invention in the hole transporting layer provide a high light emission efficiency and a prolonged lifetime, as compared to the organic EL elements using the known aromatic amine derivative in the hole transporting layer. Furthermore, the organic EL elements using the aromatic amine derivative of the present invention in the hole transporting layer can be operated at a low voltage.

INDUSTRIAL APPLICABILITY

The utilization of the aromatic amine derivative of the present invention as an organic EL element material (particularly as a hole transporting material) provides an organic EL element that may be driven at a low voltage and has a high light emission efficiency and a prolonged lifetime. Accordingly, the organic EL element of the present invention may be utilized as a flat light emission device, such as a flat panel display of a wall-mounted television, a duplicator, a printer, a backlight of a liquid crystal display, a light source of a measuring instrument or the like, a sign board, a marker light, and the like.

The aromatic amine derivative of the present invention is useful not only for an organic EL element but also in such fields as an electrophotographic photoreceptor, a photoelectric conversion element, a solar cell and an image sensor.

The invention claimed is:

1. An aromatic amine derivative of formula (1):

wherein:

Ar$^1$ is an organic group A of formula (A-1) or (A-2):

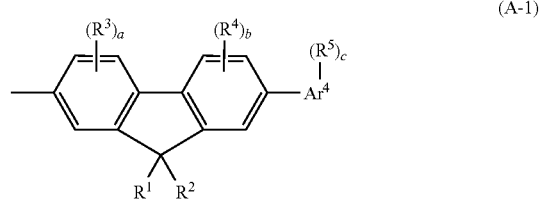

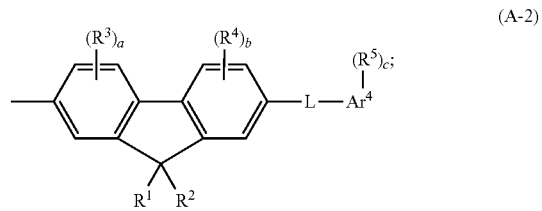

Ar$^4$ is a substituted or unsubstituted condensed ring group having from 10 to 14 ring-forming carbon atoms;

R$^1$ and R$^2$ are each independently a hydrogen atom, an alkyl group having from 1 to 10 carbon atoms, a cycloalkyl group having from 3 to 10 ring-forming carbon atoms or an aryl group having from 6 to 12 ring-forming carbon atoms, provided that R$^1$ and R$^2$ may be bonded to each other to form a hydrocarbon ring;

R$^3$, R$^4$, and R$^5$ are each independently an alkyl group having from 1 to 10 carbon atoms, a cycloalkyl group having from 3 to 10 ring-forming carbon atoms, or an aryl group having from 6 to 12 ring-forming carbon atoms, or two or more of R$^3$, R$^4$, and R$^5$ are bonded to each other to form a hydrocarbon ring;

L is a substituted or unsubstituted arylene group having from 6 to 10 ring-forming carbon atoms;

a, b, and c are each independently an integer of from 0 to 2, provided that when a, b, or c is 2, the hydrocarbon ring includes a ring formed by bonding plural groups of $R^3$, plural groups of $R^4$, or plural groups of $R^5$;

$Ar^2$ is an organic group B of formula (B-1):

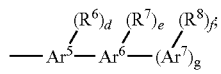
(B-1)

$Ar^5$ and $Ar^6$ are each independently a substituted or unsubstituted arylene group having from 6 to 14 ring-forming carbon atoms;

$Ar^7$ is a substituted or unsubstituted aryl group having from 6 to 14 ring-forming carbon atoms;

$R^6$, $R^7$, and $R^8$ are each independently an alkyl group having from 1 to 10 carbon atoms, a cycloalkyl group having from 3 to 10 carbon atoms or an aryl group having from 6 to 12 ring-forming carbon atoms;

d, e, and f are each independently an integer of from 0 to 2;

g is 0 or 1;

$Ar^3$ is an organic group C of formula (C-1):

(C-1)

$R^{11}$ is an alkyl group having from 1 to 10 carbon atoms or a cycloalkyl group having from 3 to 10 carbon atoms; and h is an integer of from 0 to 2, provided that when h is 2, plural groups of $R^{11}$ are not bonded to each other to form a ring.

2. The aromatic amine derivative according to claim 1, wherein the organic group B is of formula (B-2):

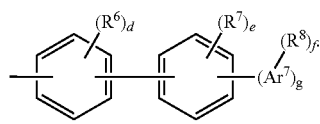
(B-2)

3. The aromatic amine derivative according to claim 2, wherein the organic group B is of formula (B-3), formula (B-4), or formula (B-5):

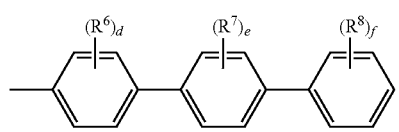
(B-3)

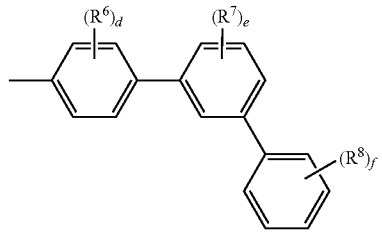
(B-4)

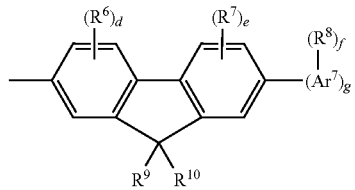
(B-5)

wherein $R^9$ and $R^{10}$ are each independently a hydrogen atom, an alkyl group having from 1 to 10 carbon atoms, a cycloalkyl group having from 3 to 10 ring-forming carbon atoms or an aryl group having from 6 to 12 ring-forming carbon atoms.

4. The aromatic amine derivative according to claim 1, wherein $Ar^1$ is an organic group A of formula (A-1).

5. The aromatic amine derivative according to claim 1, wherein in formulae (A-1) and (A-2), $R^1$ and $R^2$ are not bonded to each other to form a hydrocarbon ring.

6. An organic electroluminescent element material comprising the aromatic amine derivative according to claim 1.

7. A hole transporting material, wherein the hole transporting material is suitable for an organic electroluminescent element comprising the aromatic amine derivative according to claim 1.

8. An organic electroluminescent element comprising an anode, a cathode, a light emitting layer between the anode and cathode, and an organic thin film layer comprising the aromatic amine derivative according to claim 1.

9. The organic electroluminescent element according to claim 8, wherein the organic thin film layer comprises a hole transporting layer comprising the aromatic amine derivative.

10. The organic electroluminescent element according to claim 8, wherein the organic thin film layer comprises a hole injection layer and a hole transporting layer, and the hole transporting layer comprises the aromatic amine derivative.

11. The organic electroluminescent element according to claim 8, wherein the light emitting layer comprises at least one selected from the group consisting of an anthracene derivative, a fluoranthene derivative, a styrylamine derivative and an arylamine derivative.

12. The organic electroluminescent element according to claim 8, wherein the organic thin film layer comprises a hole injection layer and a hole transporting layer, and the hole injection layer, the hole transporting layer, or both, comprise an acceptor material.

* * * * *